US012790305B2

(12) United States Patent
Brantis et al.

(10) Patent No.: US 12,790,305 B2
(45) Date of Patent: Nov. 10, 2026

(54) SUCCINATE SALTS OF N-(3-(4-(3-(DIISOBUTYLAMINO)PROPYL) PIPERAZIN-1-YL)PROPYL)-1H-BENZO[D]IMIDAZOL-2-AMINE, PREPARATION THEREOF AND USE OF THE SAME

(71) Applicant: ALZPROTECT, Loos (FR)

(72) Inventors: Cyrille Brantis, Marcq en Baroeul (FR); Stéphane Burlet, Croix (FR); Jonathan Loughrey, Edinburgh (GB); Saurabh Chitre, Bonnyrigg (GB); Gavin Pringle, Scotland (GB)

(73) Assignee: ALZPROTECT, Loos (FR)

( * ) Notice: Subject to any disclaimer, the term of this patent is extended or adjusted under 35 U.S.C. 154(b) by 694 days.

(21) Appl. No.: 18/044,682

(22) PCT Filed: Sep. 30, 2021

(86) PCT No.: PCT/EP2021/076980
§ 371 (c)(1),
(2) Date: Mar. 9, 2023

(87) PCT Pub. No.: WO2022/069654
PCT Pub. Date: Apr. 7, 2022

(65) Prior Publication Data

US 2023/0391729 A1 Dec. 7, 2023

(30) Foreign Application Priority Data

Oct. 1, 2020 (EP) .................................... 20306141

(51) Int. Cl.
*C07D 235/30* (2006.01)
*A61P 25/28* (2006.01)

(52) U.S. Cl.
CPC ........... *C07D 235/30* (2013.01); *A61P 25/28* (2018.01); *C07B 2200/13* (2013.01)

(58) Field of Classification Search
CPC .... C07D 235/30; A61P 25/28; C07B 2200/13
See application file for complete search history.

(56) References Cited

U.S. PATENT DOCUMENTS

| | | | | |
|---|---|---|---|---|
| 8,993,576 B2 * | 3/2015 | Hamblin | A61P 11/02 | 514/254.02 |
| 9,044,478 B2 * | 6/2015 | Sergeant | A61P 35/00 | |
| 2008/0262008 A1 * | 10/2008 | Mirmehrabi | C07D 239/42 | 544/332 |

FOREIGN PATENT DOCUMENTS

| | | | |
|---|---|---|---|
| CN | 110049976 A | 7/2019 | |
| RU | 2655454 | 5/2018 | |
| WO | 2006/051489 | 5/2006 | |
| WO | 2014/102339 | 7/2014 | |
| WO | WO-2014102339 A1 * | 7/2014 | A61P 25/28 |
| WO | 2018/017153 | 1/2018 | |

OTHER PUBLICATIONS

Lee, Daniel C. et al. "LPS- induced inflammation exacerbates phosphotau pathology in rTg4510 mice" Journal of Neuroinflammation (2010) vol. 7(56), 16 pages.
Sarma, Bipul et al. "Solid forms of pharmaceuticals: Polymorphs, salts and cocrystals" Korean J. Chem. Eng.(2011) vol. 28(2), pp. 315-322.
Variankaval, Narayan et al. "From Form to Function: Crystallization of Active Pharmaceutical Ingredients" AlChE Journal (2008) vol. 54(7), pp. 1682-1688.
United States Food and Drug Administration Guidance for Industry with regards to the Chemistry, Manufacturing and Controls (CMC) requirements for the submission of Abbreviated New Drug Applications when a drug substance exists in polymorphic forms (Jul. 2007).
Chitramuthu, Babydumari P. et al. "Progranulin: a new avenue towards the understanding and treatment of neurodegenerative disease" Brain A journal of Neurology (2017) pp. 1-24.
Petkau, Terri L. et al. "Progranulin in neurodegenerative disease" Trends in Neurosciences (2014) vol. 37(7), p. 388-398.
Matsuwaki, Takashi et al. "Age-Dependent Changes in Progranulin Expression in the Mouse Brain" Journal of Reproduction and Development (2011) vol. 57(1), pp. 113-119.
Naphade, Swati B. "Progranulin expression is upregulated after spinal contusion in mice" Acta Neuropathol. (2010) vol. 119(1), pp. 123-133.
Tanaka, Y. et al. "Increased Lysosomal Biogenesis in Activated Microglia and Exacerbated Neuronal Damage After Traumatic Brain Injury in Progranulin-Deficient Mice" Neuroscience 250 (2013), pp. 8-19.
Iosokawa, Masato et al. "Progranulin Reduction is Associated With Increased Tau Phosphorylation in P301L Tau Transgenic Mice" J Neuropathol Exp Neurol (2015) vol. 74(2), pp. 158-165.
Townley, Ryan A. et al. "Progranulin: Functions and neurologic correlations" American Academy of Neurology (2018) vol. 90 (3), pp. 118-125.

(Continued)

*Primary Examiner* — Samantha L Shterengarts
*Assistant Examiner* — Ernesto Valle
(74) *Attorney, Agent, or Firm* — McDonnell Boehnen Hulbert & Berghoff LLP

(57) ABSTRACT

The present invention relates to succinate salts of N-(3-(4-(3-(diisobutylamino)propyl)piperazin-1-yl)propyl)-1H-benzo[d]imidazol-2-amine and pharmaceutically acceptable solvates thereof, preparation thereof, pharmaceutical compositions containing them and use of the same in the treatment and/or prevention of neurodegenerative diseases.

3 Claims, 28 Drawing Sheets

(56) References Cited

OTHER PUBLICATIONS

Wang, Wenzhang et al. "The ALS disease-associated mutant TDP-43 impairs mitochondrial dynamics and function in motor neurons" Human Molecular Genetics (213) vol. 22*(33), pp. 4709-4719.
Van Kampen, Jackalina M. et al. "Progranulin Gene Delivery Protects Dopaminergic Neurons in a Mouse Model of Parkinson's Disease" PLOS One (2014) vol. 9(5), e97032.
Yao, Yi-Na et al. "Reduced plasma progranulin levels are associated with the severity of Parkinson's disease" Neuroscience Letters 725 (2020). 134873.
International Search Report mailed Nov. 5, 2021 for International Application No. PCT/EP2021/076980, 3 pages.
Stahl and Wermuth, Handbook of pharmaceutical salts: properties, selection, and use ED, Jan. 1, 2002, pp. 212-217.
Kazuhide Ashizawa, Pharmaceutical Polymorphism and Crystallization Science, Maruzen Planet Co., Ltd., 2002, pp. 305-311.
C. G. Wermuth, editor, "Latest Drug Development Chemistry Part 2", Technomic Co., Ltd., Sep. 25, 1999, pp. 347-365.
International Search Report (ISR) and Written Opinion for PCT/EP2021/076980 dated Oct. 18, 2021, pp. 1-8.
"Handbook of pharmaceutical salts: properties, selection, and use ED—Stahl Peter Heinrich; Wermuth Camille G" Jan. 1, 2002 (Jan. 1, 2002), Handbook of Pharmaceutical Salts : Properties Selection, and Use, Zurich : Verl. Helvetica Chimica Acta•—Weinheim [U .A.] Wiley-VCH, DE, pp. 212-217, XP003024996.
Berge, Stephen M. et al. " Pharmaceutical Salts" Journal of Pharmaceutical Sciences (1977) vol. 66(1), pp. 1-19.
Russian Search Report of RU 2023107625 dated Sep. 25, 2023, pp. 1-3.
Bastin, Richard J. et al. "Salt Selection and Optimisation Procedures for Pharmaceutical New Chemical Entities" Organic Process Research & Development (2000) vol. 4, pp. 427-435.
Caira, Mino R. et al. "Crystalline Polymorphism of Organic Compounds" Topics in Current Chemistry (1998) vol. 198, pp. 163-208.
Thackaberry, Evan A. "Non-clinical toxicological consideration for pharmaceutical salt selection" Expert Opinion on Drug Metabolism & Toxicology (2012) vol. 8(11), pp. 1419-1433.
Morissette, Sherry L. et al. "High-through put crystallization: polymorphs, salts, co-crystals and solvates of pharmaceutical solids" Advanced Drug Delivery Reviews (2004) vol. 56, pp. 275-300.
Tian, Fang et al. "Factors affecting crystallization of hydrates" Journal of Pharmacy and Pharmacology (2010) vol. 62, pp. 1534-1546.

* cited by examiner

| No. | Peak Name | Retention Time | Rel. Ret.Time. | Area | Height | Rel.Area |
|---|---|---|---|---|---|---|
| | | min | | mAU*min | mAU | % |
| UV_VIS_1 | UV_VIS_1 | UV_VIS_1 | UV_VIS_1 | UV_VIS_1 | UV_VIS_1 | UV_VIS_1 |
| 1 | Unknown | 8.421 | 0.79 | 0.109 | 2.653 | 0.05 |
| 2 | Unknown | 10.18 | 0.96 | 0.441 | 10.894 | 0.21 |
| 3 | Form 1 | 10.651 | 1 | 204.615 | 1204.862 | 99.23 |
| 4 | Unknown | 11.171 | 1.05 | 0.689 | 10.508 | 0.33 |
| 5 | Unknown | 11.335 | 1.06 | 0.35 | 6.184 | 0.17 |
| Total: | | | | 206.204 | 1235.102 | 100 |

SUCCINATE SALTS OF N-(3-(4-(3-(DIISOBUTYLAMINO)PROPYL) PIPERAZIN-1-YL)PROPYL)-1H-BENZO[D]IMIDAZOL-2-AMINE, PREPARATION THEREOF AND USE OF THE SAME

CROSS-REFERENCE TO RELATED APPLICATIONS

This application is a U.S. national phase of International Application No. PCT/EP2021/076980, filed Sep. 30, 2021, which claims priority from European Patent Application no. EP20306141.1, filed Oct. 1, 2020, the disclosure of each of which is incorporated herein by reference in its entirety.

The present invention relates to novel succinate salts of N-(3-(4-(3-(diisobutylamino)propyl)piperazin-1-yl)propyl)-1H-benzo[d]imidazol-2-amine and pharmaceutically acceptable solvates thereof, their preparation, pharmaceutical compositions containing them and use of the same in the treatment and/or prevention of neurodegenerative diseases.

BACKGROUND OF THE INVENTION

N-(3-(4-(3-(diisobutylamino)propyl)piperazin-1-yl)propyl)-1H-benzo[d]imidazol-2-amine which has the structure of Formula I Formula I

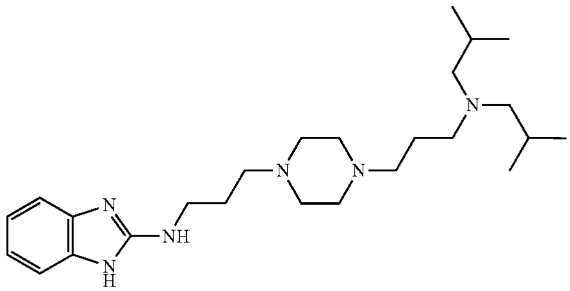

is a pharmaceutically active molecule (PAM) belonging to a family of 1,4-bis(3-aminopropyl)piperazine derivatives previously disclosed in WO 2006/051489 and useful for the treatment and/or prevention of neurodegenerative diseases.

The free base form of this compound presents long term stability issues due to oxidative degradation. Therefore, the Applicant searched for a salt form that overcomes these stability issues and discovered the sulphate salts of N-(3-(4-(3-(diisobutylamino)propyl)piperazin-1-yl)propyl)-1H-benzo[d]imidazol-2-amine which are described in WO 2014/102339. The sulphate salts are devoid of oxidative degradation and are obtained as stable powders which have a crystalline phase with good crystallinity; they are not hygroscopic based on commonly used criteria (i.e. less than 2% by weight water uptake at 25 °C/60% relative humidity (RH)). In particular, the Applicant found that N-(3-(4-(3-(diisobutylamino)propyl)piperazin-1-yl)propyl)-1H-benzo[d]imidazol-2-amine di-sulphate is stable to regular storage conditions (15-25 °C) for at least 5 years and has a remarkable water solubility greater than 100 mg/mL. Therefore, the sulphate salts of N-(3-(4-(3-(diisobutylamino)propyl)piperazin-1-yl)propyl)-1H-benzo[d]imidazol-2-amine are suitable active pharmaceutical ingredients (API).

The N-(3-(4-(3-(diisobutylamino)propyl)piperazin-1-yl)propyl)-1H-benzo[d]imidazol-2-amine di-sulphate API is being developed for the treatment of neurodegenerative diseases and successfully completed phase 1 clinical trials with healthy volunteers. This di-sulphate salt API was orally administered to healthy volunteers in liquid formulation: a solution in water. These aqueous solutions are easy to prepare and remarkably stable (up to 18 months at 5 °C, up to 18 months at 25 °C/60% RH, up to 6 months at 40 °C/75% RH, in glass vials) without the need for any preservative. The same formulation is used in the ongoing phase 2A clinical trial with patients suffering from progressive supranuclear palsy (PSP).

The Applicant wished to develop a solid formulation (e.g. capsule) of the N-(3-(4-(3-(diisobutylamino)propyl)piperazin-1-yl)propyl)-1H-benzo[d]imidazol-2-amine PAM under a salt form, the free base being excluded for its instability issue and lower solubility. Indeed, solid formulations present numerous advantages over liquid ones: stability, packaging, supply, storage, handling and logistics are easier and more cost-effective. Unlike liquid formulations, the development of solid formulation (regulatory compliance) entails the API to be a unique well-defined polymorphic form. Polymorphic forms or polymorphs of a molecule refer to different solid states of the molecule which have different and unique physico-chemical properties such as crystallinity, melting point, solubility and stability. The properties of an API and solid formulations thereof are dependent on the polymorphic form of the API; polymorphs may exhibit different stability, solubility, dissolution rates which could dramatically impact the bioavailability of a drug. Therefore, drug approval and regulatory authorities require solid formulations of drugs to be a unique stable polymorph of the API; as an example reference is made to the United States Food and Drug Administration Guidance for Industry with regards to the Chemistry, Manufacturing and Controls (CMC) requirements for the submission of Abbreviated New Drug Applications when a drug substance exists in polymorphic forms (docket n° FDA-2004-D-0182). Selecting the right polymorphic form of the right salt is thus crucial for API development and implementing a highly reproducible chemical process for its synthesis is equally detrimental. In the instant case, the last step of the API synthetic process is the salt formation which needs to be optimized in order to obtain the chosen polymorphic form directly. In other words, the process would be more efficient and cost-effective in selecting a salt/polymorphic form which is compatible with a one-pot salt formation—direct crystallisation final step.

The Applicant first investigated the N-(3-(4-(3-(diisobutylamino)propyl)piperazin-1-yl)propyl)-1H-benzo[d]imidazol-2-amine di-sulphate salt and carried out a comprehensive polymorph screening which led to the identification of numerous polymorphic forms. The polymorphic form named "Form A", which XRPD diffractogram is shown in FIG. 1, was identified as the most suitable, stable form to take forward for preparing a solid formulation. The Applicant then sought to develop a reproducible chemical process synthesis of Form A, i.e. to identify the suitable conditions (solvents, anti-solvents, concentrations, durations, temperatures, nucleation conditions, filtration, drying conditions) for the one-pot di-sulphate salt formation/direct crystallisation under this polymorphic form from the free base starting material. Despite extensive research, the Applicant was not able to achieve this result and could only obtain the desired Form A polymorphic form in 2 distinct steps from the free base: 1) di-sulphate salt formation under polymorphic form named "Form B", followed by 2) conversion of Form B to the targeted Form A. The Applicant further identified that the targeted Form A is sensitive to drying conditions as it converts back to polymorphic Form B upon drying at 50 °C. Such sensitivity would further limit the process on an industrial scale and the Applicant investigated Form B instead since this form is amenable to the more efficient one-pot salt formation/crystallisation final step.

Form B, which XRPD diffractogram is disclosed in FIG. 2, is the most prominent polymorphic form of N-(3-(4-(3-(diisobutylamino)propyl)piperazin-1-yl)propyl)-1H-benzo[d]imidazol-2-amine di-sulphate identified from the polymorph screening studies. However, there is a risk of crystalline form conversion in several various solvents or under high humidity conditions, and it may be prone to salt disproportionation (formation of tris-sulphate salt) in alcoholic solvents. Additionally, Form B partially loses its crystallinity upon long drying periods at 50 °C. Therefore, the Applicant disregarded Form B as a suitable polymorphic form for developing a solid formulation.

N-(3-(4-(3-(diisobutylamino)propyl)piperazin-1-yl)propyl)-1H-benzo[d]imidazol-2-amine di-sulphate, despite being a stable, crystalline, non-hygroscopic powder API, presents a complicated polymorphism landscape with regards to crystalline form stability and synthetic process efficiency. A robust, cost-effective synthetic process with a one-pot salt formation/direct crystallisation final step could not be envisaged to guarantee the obtention of a specific stable polymorphic form. The polymorphs of N-(3-(4-(3-(diisobutylamino)propyl)piperazin-1-yl)propyl)-1H-benzo[d]imidazol-2-amine which passed the polymorphism screening criteria being unstable upon conventional drying at 50 °C to boot, the Applicant came to the conclusion that the di-sulphate salt could not be suitable to obtain a solid formulation of the N-(3-(4-(3-(diisobutylamino)propyl)piperazin-1-yl)propyl)-1H-benzo[d]imidazol-2-amine PAM.

WO 2014/102339 discusses other salts of N-(3-(4-(3-(diisobutylamino)propyl)piperazin-1-yl)propyl)-1H-benzo[d]imidazol-2-amine. The oxalate salt originally reported in WO 2006/051489 was not suitable due to the nephrotoxicity oxalate ions can trigger. The hydrochloride salt was straightforwardly found very hygroscopic while acetate salts were not obtained in solid form. Tartrate and fumarate salts were obtained as amorphous solids. The malate salt was discarded due to its chirality which considerably complicate clinical development since each stereoisomer needs to be equally characterized as the active stereoisomer.

There is thus still a need in the art for stable polymorphic forms of new salts of N-(3-(4-(3-(diisobutylamino)propyl)piperazin-1-yl)propyl)-1H-benzo[d]imidazol-2-amine that are especially suitable for solid formulation and obtainable from a robust chemical process.

SUMMARY OF THE INVENTION

The present invention is based on the unexpected findings that succinate salts of N-(3-(4-(3-(diisobutylamino)propyl)piperazin-1-yl)propyl)-1H-benzo[d]imidazol-2-amine provide stable powders, which polymorphs have a high degree of crystallinity, are very stable, non-hygroscopic and obtainable in a good yield in a one-pot salt formation/direct crystallisation from the free base. The succinate salts satisfy to the demanding criteria set forth above and are especially suitable for use as an API in solid formulations like capsules.

The invention thus concerns succinate salts of N-(3-(4-(3-(diisobutylamino)propyl)piperazin-1-yl)propyl)-1H-benzo[d]imidazol-2-amine and pharmaceutically acceptable solvates thereof.

Succinate salts of N-(3-(4-(3-(diisobutylamino)propyl)piperazin-1-yl)propyl)-1H-benzo[d]imidazol-2-amine and solvates thereof are obtained as powders which have a crystalline phase with a high degree of crystallinity and a defined morphology. The succinate salts of the invention are moreover especially suitable for the preparation of pharmaceutical compositions containing them. The succinate salt is pharmaceutically acceptable and up to the Applicant's knowledge is not associated with any inherent toxicity of any kind.

Moreover, when compared to other salts, such as sulphate salts, the succinate salt has a simpler polymorphic landscape, the polymorphic forms are of higher crystallinity, more stable (i.e. no alteration of crystalline form) during the synthetic process, in particular to regular 50 °C drying, and does not disproportionate (i.e. stoichiometry change) in the solvents used in the process.

The use of succinate salts would consequently strengthen and ease the production of pharmaceutical compositions containing the N-(3-(4-(3-(diisobutylamino)propyl)piperazin-1-yl)propyl)-1H-benzo[d]imidazol-2-amine PAM while decreasing the associated costs.

DETAILED DESCRIPTION OF THE INVENTION

The compounds of the invention are succinate salts of N-(3-(4-(3-(diisobutylamino)propyl)piperazin-1-yl)propyl)-1H-benzo[d]imidazol-2-amine and pharmaceutically acceptable solvates thereof. More particularly, the succinate salts of the invention and solvates thereof are those of Formula II Formula II

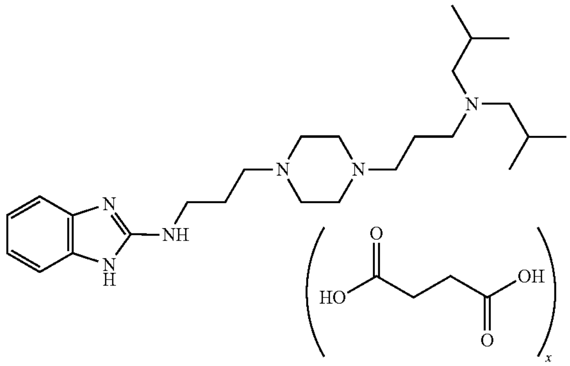

wherein x is 1 to 4, preferably x is 1.4 to 3.1, more preferably x is 1.4 to 1.6, still more preferably x is about 1.5, even more preferably x is 1.5.

In other words, the succinate salt of N-(3-(4-(3-(diisobutylamino)propyl)piperazin-1-yl)propyl)-1H-benzo[d]imidazol-2-amine contains 1 to 4 equivalents, preferably 1.4 to 3.1 equivalents, more preferably 1.4 to 1.6 equivalents, still more preferably about 1.5 equivalents and even more preferably 1.5 equivalents of succinate for one molecule of N-(3-(4-(3-(diisobutylamino)propyl)piperazin-1-yl)propyl)-1H-benzo[d]imidazol-2-amine.

In one preferred embodiment, the succinate salt of the invention is the sesqui-succinate salt of N-(3-(4-(3-(diisobutylamino)propyl)piperazin-1-yl)propyl)-1H-benzo[d]imidazol-2-amine.

In one embodiment, preferred succinate salts of the invention are the compounds of Formula II wherein x is 2.9 to 3.1, preferably wherein x is about 3, more preferably x is 3.

In another preferred embodiment, the succinate salt of the invention is the tris-succinate salt of N-(3-(4-(3-(diisobutylamino)propyl)piperazin-1-yl)propyl)-1H-benzo[d]imidazol-2-amine.

In a particular embodiment, the succinate salt of Formula II is in the form of a pharmaceutically acceptable solvate, preferably a hydrate. The solvate stoichiometry is between 0.4 to 2, preferably between 0.4 to 1.2, more preferably between 0.5 to 1.1, still more preferably about 0.5 or about 1.1, even more preferably 0.5 or 1.1 molecules of solvate for 1 molecule of succinate salt of Formula II.

In one embodiment, the compound of the invention is N-(3-(4-(3-(diisobutylamino)propyl)piperazin-1-yl)propyl)-1H-benzo[d]imidazol-2-amine sesqui-succinate salt hemihydrate.

In another embodiment, the compound of the invention is the N-(3-(4-(3-(diisobutylamino)propyl)piperazin-1-yl)propyl)-1H-benzo[d]imidazol-2-amine sesqui-succinate salt mono-hydrate.

The Applicant has identified several polymorphic forms of the compounds of the invention which are particularly stable to 1) chemical degradation such as salt disproportionation and 2) polymorphic change. These polymorphs have a high degree of crystallinity, are stable under regular storage and stressed conditions, are not hygroscopic. The Applicant has found experimental conditions for the specific preparation of these polymorphic forms using a one-pot salt formation/crystallization final step from the free base. The compounds of the invention are thus useful as API for use in solid formulations.

In one embodiment, one particularly preferred compound of the invention is the compound of Formula II wherein x is 1.5 under the crystalline form having an X-ray powder diffraction (XRPD) pattern comprising peaks at diffraction angles of 2θ=3.8°±0.2°, 10.3°±0.2°, 12.4°±0.2°, 16.2°±0.2°, 17.9°±0.2°, 19.8°±0.2°, 20.4°±0.2°, 23.8°±0.2° and 26.7°±0.2° when irradiated with a CuKα light source. This specific crystalline form is referred to as "Form 1" throughout the application and its XRPD diffractogram recorded on a PANalytical X'pert pro with PIXcel detector (128 channels) is shown in FIG. 3.

Another preferred compound of the invention is the compound of Formula II wherein x is 3 under the crystalline form having an X-ray powder diffraction (XRPD) pattern comprising peaks at diffraction angles of 2θ=5.3°±0.2°, 15.0°±0.2°, 15.3°±0.2°, 16.8°±0.2°, 17.9°±0.2°, 20.5°±0.2°, 21.2°±0.2°, 23.9°±0.2°, 24.3°±0.2° and 26.6°±0.2° when irradiated with a CuKα light source. This specific crystalline form is referred to as "Form 2" throughout the application and its XRPD diffractogram recorded on a PANalytical X'pert pro with PIXcel detector (128 channels) is shown in FIG. 4.

Another preferred compound of the invention is the compound of Formula II wherein x is 1.5, y is 0.5 and under the crystalline form having an X-ray powder diffraction (XRPD) pattern comprising peaks at diffraction angles of 2θ=3.8°±0.2°, 4.4°±0.2°, 9.2°±0.2°, 10.6°±0.2°, 13.8°±0.2°, 17.7°±0.2°, 19.9°±0.2°, 21.6°±0.2° and 23.6°±0.2° when irradiated with a CuKα light source. Its XRPD diffractogram recorded on a PANalytical X'pert pro with PIXcel detector (128 channels) is shown in FIG. 5.

Another preferred compound of the invention is the compound of Formula II wherein x is 1.5, y is 1.1 and under the crystalline form having an X-ray powder diffraction (XRPD) pattern comprising peaks at diffraction angles of 2θ=4.2±0.2°, 4.4°±0.2°, 9.6°±0.2°, 10.6°±0.2°, 15.0°±0.2°, 16.3°±0.2°, 17.4°±0.2°, 19.7°±0.2°, 22.8°±0.2°, 29.1 and 29.7°±0.2° when irradiated with a CuKα light source. Its XRPD diffractogram recorded on a PANalytical X'pert pro with PIXcel detector (128 channels) is shown in FIG. 6.

Crystalline forms of N-(3-(4-(3-(diisobutylamino)propyl)piperazin-1-yl)propyl)-1H-benzo[d]imidazol-2-amine sesqui-succinate salt can be obtained by a chemical synthesis process. Such a process is another object of the invention.

The invention also concerns a process for making crystalline forms of N-(3-(4-(3-(diisobutylamino)propyl)piperazin-1-yl)propyl)-1H-benzo[d]imidazol-2-amine sesqui-succinate salt comprising the steps of:

step 1: dissolving N-(3-(4-(3-(diisobutylamino)propyl)piperazin-1-yl)propyl)-1H-benzo[d]imidazol-2-amine in an organic solvent;

step 2: heating the reaction medium to temperature B, wherein temperature B is defined as a temperature comprised between 30 and 50 °C;

step 3: adding a substantially equimolar amount of succinic acid;

step 4: stirring the reaction medium at temperature B for 0.25 to 4 hours;

step 5: temperature cycling the reaction medium between temperature A and temperature B in 2 to 4-hour cycles for 10 to 30 hours wherein temperature A is defined as a temperature comprised between 0 and 10 °C;

step 6: cooling down the reaction medium to temperature A;

step 7: filtering the reaction medium at temperature A;

step 8: washing the filter cake with said organic solvent at temperature A;

step 9: drying the filter cake at a temperature between 30 and 50 °C.

In the first step, a solution of N-(3-(4-(3-(diisobutylamino)propyl)piperazin-1-yl)propyl)-1H-benzo[d]imidazol-2-amine is provided. The N-(3-(4-(3-(diisobutylamino)propyl)piperazin-1-yl)propyl)-1H-benzo[d]imidazol-2-amine starting material useful for making the solution can be in any physical form of the free base including the solvated forms, in degrees of purity ≥95%. In one embodiment, the organic solvent is selected from the group consisting of acetone, 97.5% acetone/2.5% water (% v/v), methyl ethyl ketone, acetonitrile, tert-butylmethyl ether. In one particularly preferred embodiment, the organic solvent used is methyl ethyl ketone which is especially suitable for preparing crystalline Form 1. The volume of organic solvent used is important to achieve dissolution of the free base and allow a successful salt formation and crystallization thereof. In one preferred embodiment, the amount of organic solvent added is between 20 and 40 mL/g of free base, preferably between 25 and 35 mL/g of free base, more preferably about 30 mL/g of free base.

In one preferred embodiment, the heating step 2 is carried out at a temperature B comprised between 35 and 45 °C, more preferably between 40 and 45 °C, still more preferably at a temperature about 40 °C, even more preferably at 40 °C.

An optional filtration step at temperature B can be realized between step 2 and following succinic acid addition step 3. The succinic acid is added in a substantially equimolar amount with respect to the N-(3-(4-(3-(diisobutylamino)propyl)piperazin-1-yl)propyl)-1H-benzo[d]imidazol-2-amine free base. In other terms, between 0.95 equivalents (eq.) and 1.05 equivalents (eq.) in relation to the free base of succinic acid are added. In one preferred embodiment, 1.0 equivalent of succinic acid is used.

In step 3, the succinic acid addition is done by portions using succinic acid in powder form or by the slow addition of a suspension or solution of concentrated succinic acid in the organic solvent used to dissolve the base. In one preferred embodiment, the succinic acid is added in powder form. In another preferred embodiment, the succinic acid is added as a concentrated solution in the organic solvent.

In step 4, the salt formation begins while reaction medium is then stirred at temperature B for 0.5 to 4 hours. In one preferred embodiment, the medium is stirred between 20 and 40 minutes, preferably for about 30 minutes. In another preferred embodiment, the medium is stirred between 2 and 4 hours, preferably for about 3 hours.

Subsequent temperature cycling step 5 allows the sesqui-succinate salt to crystallize under a specific crystalline form. Temperature cycling is performed between temperature A and temperature B in 2 to 4-hour cycles for 10 to 30 hours wherein temperature A is defined as a temperature comprised between 0 and 10 °C. In a particularly preferred embodiment, the temperature cycling is performed between about 5 °C and about 40 °C in about 3-hour cycles for about 20 hours thus allowing the sesqui-succinate to crystallize under crystalline Form 1, especially when methylethyl ketone is used as the organic solvent.

At this point, the crystalline salt generally precipitated and the reaction medium is cooled down to a temperature comprised between 0 and 10 °C, preferably about 5 °C (step 6) before recovery of the desired material by filtration at the same temperature (step 7). The desired crystalline salt is recovered in the filter cake which is washed once with the same organic solvent as the one used in the reaction (step 8). In one preferred embodiment, a volume of about 5 mL of organic solvent per g of material is used in the filter cake washing.

The filtered and washed material is then dried (step 9), preferably under reduced pressure, at a temperature between 30 and 50 °C, preferably about 40 °C.

A particularly preferred process of the invention that enables to obtain N-(3-(4-(3-(diisobutylamino)propyl)piperazin-1-yl)propyl)-1H-benzo[d]imidazol-2-amine sesqui-succinate salt Form 1, is

- step 1: dissolving N-(3-(4-(3-(diisobutylamino)propyl)piperazin-1-yl)propyl)-1H-benzo[d]imidazol-2-amine in methyl ethyl ketone;
- step 2: heating the reaction medium to 45 °C;
- step 3: adding an equimolar amount of succinic acid;
- step 4: stirring the reaction medium at 45 °C for 3 to 4 hours;
- step 5: temperature cycling the reaction medium between 5 °C and 40 °C in 3-hour cycles for 20 hours;
- step 6: cooling down the reaction medium to 5 °C;
- step 7: filtering the reaction medium at 5 °C;
- step 8: washing the filter cake with said organic solvent at 5 °C;
- step 9: drying the filter cake under reduced pressure at 40 °C.

The process according to the invention, allows the direct one-pot salt formation/crystallization of N-(3-(4-(3-(diisobutylamino)propyl)piperazin-1-yl)propyl)-1H-benzo[d]imidazol-2-amine sesqui-succinate salt.

When adapted by 1) using ethanol as the organic solvent and 2) changing the stoichiometry of succinic acid to about 2 equivalents in step 3, the process according to the invention allows the direct one-pot salt formation/crystallization of N-(3-(4-(3-(diisobutylamino)propyl)piperazin-1-yl)propyl)-1H-benzo[d]imidazol-2-amine tris-succinate salt.

Applicant has shown that succinate salts of N-(3-(4-(3-(diisobutylamino)propyl)piperazin-1-yl)propyl)-1H-benzo[d]imidazol-2-amine and pharmaceutically acceptable solvates thereof are useful in rectifying the metabolism of the Tau protein in particular by inhibiting pathological Tau protein phosphorylation. Tau protein (a.k.a. Microtubule Associated Protein Tau—MAPT) interacts with tubulin to stabilize microtubules and promote tubulin assembly into microtubules, microtubule stability being controlled by isoforms and phosphorylation. Tau pathologies comprise mechanisms leading to abnormal modifications of microtubule-associated Tau protein such as its hyperphosphorylation, progressive aggregation and accumulation into fibrillar material inside degenerating neurons to form the so-called neurofibrillary tangles (NFT). The compounds of the invention are efficient at preserving neurite network of neurons and promoting neurite outgrowth. Neurites are projections from the cell body of a neuron, their preservation and growth are detrimental to inter-neuronal connections. Moreover, the compounds of the invention are able to reduce neuroinflammation and microglial activation while increasing levels of progranulin (PGRN) neurotrophic factor. Neuroinflammation is a secondary response in chronic progressive neurodegenerative diseases, including but not limited to tauopathies and Parkinson's disease, which can be triggered by activated microglial cells which release neurotoxic pro-inflammatory cytokines that contribute to neuronal loss. PGRN is a secreted glycoprotein primarily expressed in mature neurons and microglia that maintains cerebrocortical viability (*Brain J. Neurol.* 140, 3081-3104 (2017)). PGRN expression in brain is low in early development and increases with age (*Trends Neurosci.* 37, 388-398 (2014), *J. Reprod. Dev.* 57, 113-119 (2011)). However, in response to injury, activated microglia upregulates PGRN expression (*Acta Neuropathol.* (*Berl.*) 119, 123-133 (2010), *Neuroscience* 250, 8-19 (2013)). With regards to Tau pathology, PGRN deficiency accelerates Tau deposition and phosphorylation in human tau-expressing mice (*J. Neuropathol. Exp. Neurol.* 74, 158-165 (2015)). PGRN can be processed into granulin by several proteases including elastases released from activated microglia (*Neurology* 90, 118-125 (2018)). Human and rodent data have shown that PGRN reduction is associated with increased Tau pathology. PGRN haploinsufficiency increases Tau phosphorylation in P301L-Tau transgenic mice, strongly supporting the notion that the reduction in PGRN protein could contribute to hyperphosphorylation and intraneuronal accumulation of Tau (*J. Neuropathol. Exp. Neurol.* 74, 158-165 (2015)). Additionally, inflammatory stimuli in the brain have also been reported to be relevant to exacerbating Tau phosphorylation (*J. Neuroinflammation* 7, 56 (2010)). Since PGRN could act as an anti-inflammatory factor in neuroinflammation (*Neuroscience* 250, 8-19 (2013)), it is hypothesized that Tau phosphorylation would be accelerated in the inflammatory status resulting from reduced PGRN levels. PGRN is a neurotrophic factor which role in Parkinson's disease has been well investigated. Van Kampen et al. have used the 1-methyl-4-phenyl-1,2,3,6-tetrahydropyridine (MPTP) model of PD to investigate the possible use of PGRN gene delivery as a therapy for the prevention or treatment of PD (*PLOS one* 2014, 9, 5, e97032). Viral vector delivery of the PGRN gene was an effective mean of elevating PGRN expression in nigrostriatal neurons. When PGRN expression was elevated in the SNc, nigrostriatal neurons were protected from MPTP toxicity in mice, along with a preservation of striatal dopamine content and turnover. Further, protection of nigrostriatal neurons by PGRN gene therapy was accompanied by reductions in markers of MPTP-induced inflammation and apoptosis as well as a complete preservation of locomotor function. Moreover, blood levels of progranulin could reflect Parkinson's disease severity and progression in humans (*Neuroscience Letters volume* 725, 23 Apr. 2020, 134873). Progranulin plasma levels were significantly lower in Parkinson's patients compared to controls and were also found to negatively correlate with motor symptoms, disease severity and duration, thus suggesting neuroprotective effects of PGRN in PD. All these findings support that increasing PGRN levels could be an effective therapy to improve neurodegenerative diseases like tauopathies and Parkinson's disease. In particular, the succinate salts of the invention were found neuroprotective and able to considerably reduce aggregation of $\alpha$-synuclein in dopaminergic neurons injured with mitochondrial toxins $MPP^+$ or rotenone; two well-known in vitro models of PD.

Tauopathies include, but are not limited to, Alzheimer's disease, Amyotrophic lateral sclerosis and parkinsonism-dementia complex of Guam, Argyrophilic grain disease, Chronic traumatic encephalopathy, Corticobasal degeneration, Dementia pugilistica, Diffuse neurofibrillary tangles with calcification, Familial British Dementia, Familial Danish Dementia, Frontotemporal dementia (FTD), Frontotemporal dementia with Parkinsonism linked to chromosome 17 (FTDP-17), Frontotemporal lobar degeneration (FTLD), Frontotemporal dementia-granulin subtype (FTD-GRN), Gerstmann-Striussler-Scheinker disease, Guadeloupean parkinsonism, Hallervorden-Spatz disease, inclusion body myositis, multiple system atrophy, Steinert Myotonic dystrophy, Myotonic dystrophy type II, Neurodegeneration with brain iron accumulation, Niemann-Pick disease of type C, Non-Guamanian motor neuron disease with neurofibrillary tangles, Paget's disease, Pick's disease, Postencephalitic parkinsonism, Progressive subcortical gliosis, Progressive supranuclear palsy (PSP), SLC9A6-related mental retardation, Subacute sclerosing panencephalitis, Tangle-only dementia, multi-infarct dementia, ischemic stroke, chronic traumatic encephalopathy (CTE), traumatic brain injury (TBI), stroke and White matter Tauopathy with globular glial inclusions.

In addition, the physico-chemical properties of the succinate salts of the invention and solvates thereof such as crystallinity, stability, solubility, are especially useful with regards to solid and liquid drug formulation.

Therefore, due to their abilities to rectify the metabolism of the Tau protein, to increase levels of PGRN neurotrophic factor and to reduce neuroinflammation as described above, the succinate salts of the invention and solvates thereof are useful as a medicament, in particular for treating or preventing neurodegenerative diseases, including tauopathies and Parkinson's disease.

The succinate salts of the invention are thus useful as a medicament, in particular for treating or preventing neurodegenerative diseases and all diseases wherein a dysfunction of the Tau protein phosphorylation is observed, including but not limited to tauopathies.

In one embodiment, the invention concerns a succinate salt of the invention for use in treating or preventing of a disease selected from neurodegenerative diseases and diseases wherein a dysfunction of the Tau protein phosphorylation is observed, including but not limited to tauopathies Hence, the invention also concerns a succinate salt of N-(3-(4-(3-(diisobutylamino)propyl)piperazin-1-yl)propyl)-1H-benzo[d]imidazol-2-amine or a pharmaceutically acceptable solvate thereof as defined herein for use in treating and/or preventing a disease selected from Alzheimer's disease, Amyotrophic lateral sclerosis and parkinsonism-dementia complex of Guam, Argyrophilic grain disease, Chronic traumatic encephalopathy, Corticobasal degeneration, Dementia pugilistica, Diffuse neurofibrillary tangles with calcification, Familial British Dementia, Familial Danish Dementia, Frontotemporal dementia (FTD), Frontotemporal dementia with Parkinsonism linked to chromosome 17 (FTDP-17), Frontotemporal lobar degeneration (FTLD), Frontotemporal dementia-granulin subtype (FTD-GRN), Gerstmann-Straussler-Scheinker disease, Guadeloupean parkinsonism, Hallervorden-Spatz disease, inclusion body myositis, multiple system atrophy, Steinert Myotonic dystrophy, Myotonic dystrophy type II, Neurodegeneration with brain iron accumulation, Niemann-Pick disease of type C, Non-Guamanian motor neuron disease with neurofibrillary tangles, Paget's disease, Pick's disease, Postencephalitic parkinsonism, Progressive subcortical gliosis, Progressive supranuclear palsy (PSP), SLC9A6-related mental retardation, Subacute sclerosing panencephalitis, Tangle-only dementia, multi-infarct dementia, ischemic stroke, chronic traumatic encephalopathy (CTE), traumatic brain injury (TBI), stroke and White matter Tauopathy with globular glial inclusions. Preferably, the disease is selected from Alzheimer's disease, Argyrophilic grain disease, Corticobasal degeneration, Diffuse neurofibrillary tangles with calcification, Frontotemporal dementia (FTD), Frontotemporal dementia with Parkinsonism linked to chromosome 17 (FTDP-17), Frontotemporal lobar degeneration (FTLD), Frontotemporal dementia-granulin subtype (FTD-GRN), Pick's disease, Progressive subcortical gliosis, Progressive supranuclear palsy (PSP), Tangle-only dementia, and White matter Tauopathy with globular glial inclusions. More preferably, the disease is selected from Alzheimer's disease, Frontotemporal dementia (FTD), Frontotemporal dementia with Parkinsonism linked to chromosome 17 (FTDP-17), Frontotemporal lobar degeneration (FTLD), Frontotemporal dementia-granulin subtype (FTD-GRN), Progressive supranuclear palsy (PSP), Tangle-only dementia, and White matter Tauopathy with globular glial inclusions. Even more preferably, the disease is selected from Alzheimer's disease and Progressive supranuclear palsy (PSP).

In other terms, the invention also provides for a method of treating and/or preventing a disease selected from tauopathies, in particular those cited above as well as embodiments thereof, comprising administering to a patient in need thereof a pharmaceutically effective amount of a succinate salt of N-(3-(4-(3-(diisobutylamino)propyl)piperazin-1-yl)propyl)-1H-benzo[d]imidazol-2-amine or a pharmaceutically acceptable solvate thereof as described herein. In a particular embodiment, the disease is selected from Alzheimer's disease and Progressive supranuclear palsy (PSP).

In other terms, the invention also provides the use of a succinate salt of N-(3-(4-(3-(diisobutylamino)propyl)piperazin-1-yl)propyl)-1H-benzo[d]imidazol-2-amine or a pharmaceutically acceptable solvate thereof as described herein, in the manufacture of a medicament for treating and/or preventing a disease selected from tauopathies, in particular those cited above as well as embodiments thereof. In a particular embodiment, the disease is selected from Alzheimer's disease and Progressive supranuclear palsy (PSP).

In another embodiment, the invention also concerns a succinate salt of the invention for use in delaying in a patient the onset of a disease selected from neurodegenerative diseases and diseases wherein a dysfunction of the Tau protein phosphorylation is observed, including but not limited to tauopathies.

In one particular embodiment, the invention also concerns a succinate salt of N-(3-(4-(3-(diisobutylamino)propyl)piperazin-1-yl)propyl)-1H-benzo[d]imidazol-2-amine or a pharmaceutically acceptable solvate thereof as defined herein for use in delaying in a patient the onset of a disease selected from Alzheimer's disease, Amyotrophic lateral sclerosis and parkinsonism-dementia complex of Guam, Argyrophilic grain disease, Chronic traumatic encephalopathy, Corticobasal degeneration, Dementia pugilistica, Diffuse neurofibrillary tangles with calcification, Familial British Dementia, Familial Danish Dementia, Frontotemporal dementia (FTD), Frontotemporal dementia with Parkinsonism linked to chromosome 17 (FTDP-17), Frontotemporal lobar degeneration (FTLD), Frontotemporal dementia-granulin subtype (FTD-GRN), Gerstmann-Striussler-Scheinker disease, Guadeloupean parkinsonism, Hallervorden-Spatz disease, inclusion body myositis, multiple system atrophy, Steinert Myotonic dystrophy, Myotonic dystrophy type II, Neurodegeneration with brain iron accumulation, Niemann-Pick disease of type C, Non-Guamanian motor neuron disease with neurofibrillary tangles, Paget's disease, Pick's disease, Postencephalitic parkinsonism, Progressive subcortical gliosis, Progressive supranuclear palsy (PSP), SLC9A6-related mental retardation, Subacute sclerosing panencephalitis, Tangle-only dementia, multi-infarct dementia, ischemic stroke, chronic traumatic encephalopathy (CTE), traumatic brain injury (TBI), stroke and White matter Tauopathy with globular glial inclusions. Preferably, the disease is selected from Alzheimer's disease, Argyrophilic grain disease, Corticobasal degeneration, Diffuse neurofibrillary tangles with calcification, Frontotemporal dementia (FTD), Frontotemporal dementia with Parkinsonism linked to chromosome 17 (FTDP-17), Frontotemporal lobar degeneration (FTLD), Frontotemporal dementia-granulin subtype (FTD-GRN), Pick's disease, Progressive subcortical gliosis, Progressive supranuclear palsy (PSP), Tangle-only dementia, and White matter Tauopathy with globular glial inclusions. More preferably, the disease is selected from Alzheimer's disease, Frontotemporal dementia (FTD), Frontotemporal dementia with Parkinsonism linked to chromosome 17 (FTDP-17), Frontotemporal lobar degeneration (FTLD), Frontotemporal dementia-granulin subtype (FTD-GRN), Progressive supranuclear palsy (PSP), Tangle-only dementia, and White matter Tauopathy with globular glial inclusions. Even more preferably, the disease is selected from Alzheimer's disease and Progressive supranuclear palsy (PSP).

In other terms, the invention provides a method for delaying in a patient the onset of a disease selected from tauopathies, in particular those cited above as well as embodiments thereof, comprising administering to a patient in need thereof a pharmaceutically effective amount of a succinate salt of the invention or a pharmaceutically acceptable solvate thereof. In a particular embodiment, the disease is selected from Alzheimer's disease and Progressive supranuclear palsy (PSP).

In other terms, the invention also provides the use of a succinate salt of N-(3-(4-(3-(diisobutylamino)propyl)piperazin-1-yl)propyl)-1H-benzo[d]imidazol-2-amine or a pharmaceutically acceptable solvate thereof as described herein, in the manufacture of a medicament for delaying in a patient the onset of a disease selected from tauopathies, in particular those cited above as well as embodiments thereof. In a particular embodiment, the disease is selected from Alzheimer's disease and Progressive supranuclear palsy (PSP).

The invention also concerns a succinate salt of N-(3-(4-(3-(diisobutylamino)propyl)piperazin-1-yl)propyl)-1H-benzo[d]imidazol-2-amine or a pharmaceutically acceptable solvate thereof as defined herein for use in treating and/or preventing Parkinson's disease.

In other terms, the invention also provides a method of treating and/or preventing Parkinson's disease, comprising administering to a patient in need thereof a pharmaceutically effective amount of a succinate salt of N-(3-(4-(3-(diisobutylamino)propyl)piperazin-1-yl)propyl)-1H-benzo[d]imidazol-2-amine or a pharmaceutically acceptable solvate thereof as described herein.

In other terms, the invention also provides the use of a succinate salt of N-(3-(4-(3-(diisobutylamino)propyl)piperazin-1-yl)propyl)-1H-benzo[d]imidazol-2-amine or a pharmaceutically acceptable solvate thereof as described herein, in the manufacture of a medicament for treating and/or preventing Parkinson's disease.

In one particular embodiment, the invention also concerns a succinate salt of N-(3-(4-(3-(diisobutylamino)propyl)piperazin-1-yl)propyl)-1H-benzo[d]imidazol-2-amine or a pharmaceutically acceptable solvate thereof as defined herein for use in delaying in a patient the onset of Parkinson's disease.

In other terms, the invention provides a method for delaying in a patient the onset of Parkinson's disease, comprising administering to a patient in need thereof a pharmaceutically effective amount of a succinate salt of the invention or a pharmaceutically acceptable solvate thereof.

In other terms, the invention also provides the use of a succinate salt of N-(3-(4-(3-(diisobutylamino)propyl)piperazin-1-yl)propyl)-1H-benzo[d]imidazol-2-amine or a pharmaceutically acceptable solvate thereof as described herein, in the manufacture of a medicament for delaying in a patient the onset of Parkinson's disease.

According to a further feature of the present invention there is provided a method for inhibiting pathological Tau protein phosphorylation, in a patient, preferably a warm blooded animal, and even more preferably a human, in need of such treatment, which comprises administering to said patient an effective amount of a succinate salt of N-(3-(4-(3-(diisobutylamino)propyl)piperazin-1-yl)propyl)-1H-benzo[d]imidazol-2-amine of the present invention, or a pharmaceutically acceptable solvate thereof.

According to still a further feature of the present invention there is provided a method for inhibiting pathological Tau protein phosphorylation while increasing levels of neurotrophic factor progranulin (PGRN) in a patient, preferably a warm blooded animal, and even more preferably a human, in need of such treatment, which comprises administering to said patient an effective amount of succinate salt of N-(3-(4-(3-(diisobutylamino)propyl)piperazin-1-yl)propyl)-1H-benzo[d]imidazol-2-amine of the present invention or a pharmaceutically acceptable solvate thereof.

The invention also provides pharmaceutical compositions comprising a succinate salt of N-(3-(4-(3-(diisobutylamino)propyl)piperazin-1-yl)propyl)-1H-benzo[d]imidazol-2-amine or a pharmaceutically acceptable solvate thereof as described herein and at least one pharmaceutically acceptable carrier, diluent, excipient and/or adjuvant. In one embodiment, the invention also covers pharmaceutical compositions which contain, in addition to a succinate salt of N-(3-(4-(3-(diisobutylamino)propyl)piperazin-1-yl)propyl)-1H-benzo[d]imidazol-2-amine or a pharmaceutically acceptable solvate thereof as active ingredient, additional therapeutic agents and/or active ingredients.

According to one embodiment, the succinate salts of N-(3-(4-(3-(diisobutylamino)propyl)piperazin-1-yl)propyl)-1H-benzo[d]imidazol-2-amine of the invention, as well as their pharmaceutical acceptable solvates may be administered as part of a combination therapy. Thus, are included within the scope of the present invention embodiments comprising co-administration of compositions and medicaments which contain, in addition to a succinate salt of the present invention or a pharmaceutically acceptable solvate thereof as active ingredient, additional therapeutic agents and/or active ingredients. Such multiple drug regimens, often referred to as "combination therapy", may be used in the treatment and/or prevention of any neurodegenerative disease, in particular a tauopathy or Parkinson's disease. The use of such combinations of therapeutic agents is especially pertinent with respect to the treatment of the above-mentioned neurodegenerative diseases within a patient in need of treatment or one at risk of becoming such a patient.

In addition to the requirement of therapeutic efficacy, which may necessitate the use of active agents in addition to the succinate salts of N-(3-(4-(3-(diisobutylamino)propyl)piperazin-1-yl)propyl)-1H-benzo[d]imidazol-2-amine or pharmaceutically acceptable solvates thereof, there may be additional rationales which compel or highly recommend the use of combinations of drugs involving active ingredients which represent adjunct therapy, i.e., which complement and supplement the function performed by the succinate salts of N-(3-(4-(3-(diisobutylamino)propyl)piperazin-1-yl)propyl)-1H-benzo[d]imidazol-2-amine of the present invention or pharmaceutically acceptable solvates thereof. Suitable supplementary therapeutic agents used for the purpose of auxiliary treatment include drugs which, instead of directly treating and/or preventing a disease or condition mediated by or associated with pathological protein Tau phosphorylation and/or neuroinflammation, treat diseases or conditions which directly result from or indirectly accompany the basic or underlying pathological protein Tau phosphorylation and/or neuroinflammation modulated disease or condition.

According to a further feature of the present invention, a succinate salt of N-(3-(4-(3-(diisobutylamino)propyl)piperazin-1-yl)propyl)-1H-benzo[d]imidazol-2-amine, a pharmaceutically acceptable solvate thereof may be used in combination therapy with other drugs used for treating neurodegenerative diseases such as Alzheimer's disease, Progressive Supranuclear Palsy (PSP) and Parkinson's disease. More particularly, the compound of Formula II, as well as pharmaceutically acceptable solvate thereof, may be used as an adjunct therapy in combination with acetylcholinesterase inhibitors, including but not limited to donepezil (CAS n° 120014-06-4) and salts and solvates thereof, galantamine (CAS n° 357-70-0) and salts and solvates thereof, rivastigmine (CAS n° 123441-03-2) and salts and solvates thereof, tacrine (CAS n° 321-64-2) and salts and solvates thereof, or in combination with NMDA glutamate receptor antagonists, including but not limited to memantine (CAS n° 19982-08-2) and salts and solvates thereof, or in combination with dual acetylcholinesterase inhibitor and NMDA glutamate receptor antagonist, including but not limited to huperzine A (CAS n° 102518-79-6) and salts and solvates thereof, or in combination with glucagon-like peptide 1 (GLP-1) agonists, including but not limited to liraglutide (CAS n° 204656-20-2) and salts and solvates thereof, exenatide (CAS n° 141732-76-5) and salts and solvates thereof, or in combination with retinoids, including but not limited to acitretin (CAS n° 55079-83-9) and salts and solvates thereof, or in combination with calcium channel blockers (CCB), including but not limited to nilvadipine (CAS n° 75530-68-6) and salts and solvates thereof, nitrendipine (CAS n° 39562-70-4) and salts and solvates thereof, nimodipine (CAS n° 66085-59-4) and salts and solvates thereof, or in combination with angiotensin receptor blockers, including but not limited to valsartan (CAS n° 137862-53-4) and salts and solvates thereof, or in combination with tetracycline antibiotics, including but not limited to minocycline (CAS n° 10118-90-8) and salts and solvates thereof, or in combination with monoclonal antibodies selected from the group consisting of aducanumab, bapineuzumab, solanezumab, gantenerumab, crenezumab, BAN2401, GSK933776, AAB-003, SAR228810, BIIB037/BART, ABBV-8E12, BIIB092 and UCB0107, or in combination with glycosidase (0-GlcNAcase) inhibitors, or in combination with dopamine prodrugs including but not limited to levodopa optionally combined with carbodopa, or in combination with dopamine receptors agonist including but not limited to pramipexole, rotigotine, ropinirole, amantadine, or in combination with anticholinergics such as benztropine, trihexyphenidyl, or in combination with MAO-B inhibitors including but not limited to safmamide, selegiline and rasagiline, or in combination with COMT inhibitors including but not limited to entacapone, opicapone and tolcapone.

Thus, the methods of treatment and pharmaceutical compositions of the present invention may employ a succinate salt of N-(3-(4-(3-(diisobutylamino)propyl)piperazin-1-yl)propyl)-1H-benzo[d]imidazol-2-amine or a pharmaceutically acceptable solvate thereof in monotherapy. However, said methods and compositions may also be used in multiple therapy in which one or more succinate salts of N-(3-(4-(3-(diisobutylamino)propyl)piperazin-1-yl)propyl)-1H-benzo[d]imidazol-2-amine or their pharmaceutically acceptable solvates are co-administered in combination with one or more other therapeutic agents.

In the above-described embodiment, combinations of succinate salts of N-(3-(4-(3-(diisobutylamino)propyl)piperazin-1-yl)propyl)-1H-benzo[d]imidazol-2-amine or a pharmaceutically acceptable solvate thereof and other therapeutic active agents may be administered, in terms of dosage forms, either separately or in conjunction with each other, and in terms of their time of administration, either serially or simultaneously. Thus, the administration of one component agent may be prior to, concurrent with, or subsequent to the administration of the other component agent(s).

Generally, for pharmaceutical use, the succinate salts of N-(3-(4-(3-(diisobutylamino)propyl)piperazin-1-yl)propyl)-1H-benzo[d]imidazol-2-amine or pharmaceutically acceptable solvates thereof may be formulated as a pharmaceutical composition comprising at least one succinate salt of the invention or a pharmaceutically acceptable solvate thereof and at least one pharmaceutically acceptable carrier, diluent, excipient and/or adjuvant, and optionally one or more further therapeutic agents and/or active ingredients.

By means of non-limiting examples, pharmaceutical composition may be in a dosage form suitable for oral administration, for parenteral administration (such as by intravenous, intramuscular or subcutaneous injection or intravenous infusion), for topical administration, for administration by inhalation, by a skin patch, by an implant, by a suppository, etc. Such suitable administration forms—which may be solid, semi-solid or liquid, depending on the manner of administration—as well as methods and carriers, diluents and excipients for use in the preparation thereof, will be clear to the skilled person; reference is made to the latest edition of Remington's Pharmaceutical Sciences. The pharmaceutical compositions may be formulated in solid form and re-dissolved or suspended prior to use. Preferred pharmaceutical compositions of the succinate salts of the invention or solvates thereof are in a solid dosage form suitable for oral administration.

Some preferred, but non-limiting examples of dosage forms include tablets, pills, powders, lozenges, sachets, cachets, elixirs, suspensions, emulsions, solutions, syrups, aerosols, ointments, cremes, lotions, soft and hard gelatin capsules, suppositories, drops, sterile injectable solutions and sterile packaged powders (which are usually reconstituted prior to use) for administration as a bolus and/or for continuous administration, which may be formulated with carriers, excipients, and diluents that are suitable per se for such formulations, such as lactose, dextrose, sucrose, sorbitol, mannitol, starches, agar, gum acacia, calcium phosphate, alginates, tragacanth, gelatin, calcium silicate, microcrystalline cellulose, polyvinylpyrrolidone, polyethylene glycol, cellulose, (sterile) water, methylcellulose, methyl- and propylhydroxybenzoates, talc, magnesium stearate, edible oils, vegetable oils and mineral oils or suitable mixtures thereof. Particularly preferred dosage forms of the succinate salts of the invention and solvates thereof are soft and hard capsules, in particular soft and hard gelatin capsules, preferably hard gelatin capsules, which are formulated with at least one microcrystalline cellulose excipient, especially Avicel® PH101. The pharmaceutical compositions can optionally contain other substances that are commonly used in pharmaceutical formulations, such as lubricating agents, wetting agents, emulsifying and suspending agents, dispersing agents, disintegrating agents, stabilizing agents, isotonic agents, bulking agents, fillers, preserving agents, sweetening agents, flavouring agents, perfuming agents, colouring agents, antibacterial agents and/or antifungal agents such as parabens, chlorobutanol, phenol, sorbic acid, dispensing agents, flow regulators, release agents, etc. The compositions may also be formulated so as to provide rapid, sustained or delayed release of the active compound(s) contained therein.

The pharmaceutical compositions of the invention are preferably in a unit dosage form, and may be suitably packaged, for example in a box, blister, vial, bottle, sachet, ampoule or in any other suitable single-dose or multi-dose holder or container (which may be properly labelled); optionally with one or more leaflets containing product information and/or instructions for use. Generally, such unit dosages will contain between 0.05 and 1000 mg, and usually between 1 and 500 mg, of the at least one compound of the invention, e.g. about 10, 25, 50, 100, 200, 300 or 400 mg per unit dosage.

Usually, depending on the condition to be prevented or treated and the route of administration, the active compound of the invention will usually be administered between 0.01 to 100 mg per kilogram, more often between 0.1 and 50 mg, such as between 1 and 25 mg, for example about 0.5, 1, 2, 5, 10, 15, 20 or 25 mg, per kilogram body weight of the patient per day, which may be administered as a single daily dose, divided over one or more daily doses, or essentially continuously, e.g. using a drip infusion.

All references to compounds of Formula II include references to solvates, in particular hydrates, multi-component complexes and liquid crystals thereof.

The compounds disclosed throughout the present application were named using ChemDraw® Ultra version 11.0 (CambridgeSoft, Cambridge, MA, USA).

N-(3-(4-(3-(diisobutylainino)propyl)piperazin-1-yl)propyl)-1H-benzo[d]imidazol-2-amine free base can be obtained as disclosed in WO 2006/051489. The succinate salts and solvates thereof can be prepared according to techniques known in the art such as those involving precipitation, crystallization, recrystallization, lyophilisation, phase transfer or ion exchange resins.

DEFINITIONS

The definitions and explanations below are for the terms as used throughout the entire application, including both the specification, the figures and the claims.

When describing the compounds of the invention, the terms used are to be construed in accordance with the following definitions, unless indicated otherwise.

Unless otherwise stated any reference to compounds of the invention herein, means the compound of Formula II as such as well as its pharmaceutically acceptable solvates. All references to compounds of Formula II include references to pharmaceutically acceptable solvates thereof and all crystalline forms thereof.

The term "administration", or a variant thereof (e.g., "administering"), means providing the active agent or active ingredient (e.g. N-(3-(4-(3-(diisobutylamino)propyl)piperazin-1-yl)propyl)-1H-benzo[d]imidazol-2-amine), alone or as part of a pharmaceutically acceptable composition, to the patient in whom/which the condition, symptom, or disease is to be treated or prevented.

The term "Alzheimer's disease" as used herein, designates all types of Alzheimer's disease, including but not limited to the sporadic and familial types.

The expression "inhibiting" as used herein refers to a partial inhibition or reduction and to a complete inhibition.

The term "human" refers to a subject of both genders and at any stage of development (i.e. neonate, infant, juvenile, adolescent, adult).

The term "patient" refers to a warm-blooded animal, more preferably a human, who/which is awaiting the receipt of, or is receiving medical care or is/will be the object of a medical procedure.

By "pharmaceutically acceptable" is meant that the ingredients of a pharmaceutical composition are compatible with each other and not deleterious to the patient thereof.

The terms "prevent", "preventing" and "prevention", as used herein, refer to a method of delaying or precluding the onset of a condition or disease and/or its attendant symptoms, barring a patient from acquiring a condition or disease, or reducing a patient's risk of acquiring a condition or disease.

The term "sesqui" as used herein, refers to one and a half equivalent, a sesqui-succinate salt of a compound means its succinic acid addition salt wherein the succinic acid is present in a ratio of 3:2 compared with the compound in its free base form.

The term "solvate" is used herein to describe a compound in this invention that contains stoichiometric or sub-stoichiometric amounts of one or more pharmaceutically acceptable solvent molecule such as ethanol. The term "hydrate" is employed when said solvent is water. The pharmaceutically acceptable solvent molecules may be co-crystallized with the compound of the invention, and/or be present in crystalline and/or amorphous phases of solids thereof, and/or be adsorbed thereto.

The compounds of the invention include compounds of Formula II as hereinbefore defined, including all polymorphs and crystal habits thereof, prodrugs thereof and isotopically labeled compounds of Formula II.

The term "tauopathy", as used herein, refers to a disorder characterized by an abnormal metabolism of Tau protein, in particular by an abnormal phosphorylation and/or hyperphosphorylation of Tau protein and/or the presence of elevated (higher than a normal control level, e.g. higher than a normal, control level for an individual or population of individuals of the same age group) levels of Tau or Tau isoform or Tau polypeptides and/or pathological forms of Tau in a cell, a tissue, or a fluid, preferably in brain tissue and/or cerebrospinal fluid. More specifically, a Tauopathy refers to a disorder wherein intracellular aggregates of abnormally modified Tau proteins are observed such as neurofibrillary tangles (NFT), Pick bodies, astrocytic tufted and/or muscle inclusion bodies, preferably at least neurofibrillary tangles (NFT).

The term "therapeutically effective amount" (or more simply an "effective amount") as used herein means the amount of active agent or active ingredient (e.g. N-(3-(4-(3-(diisobutylamino)propyl)piperazin-1-yl)propyl)-1H-benzo[d]imidazol-2-amine) that is sufficient to achieve the desired therapeutic or prophylactic effect in the patient to which/whom it is administered.

The terms "treat", "treating" and "treatment, as used herein, are meant to include alleviating, attenuating or abrogating a condition or disease and/or its attendant symptoms.

The present invention will be better understood with reference to the following examples. These examples are intended to be representative of specific embodiments of the invention, and are not intended as limiting the scope of the invention.

Figure 26:
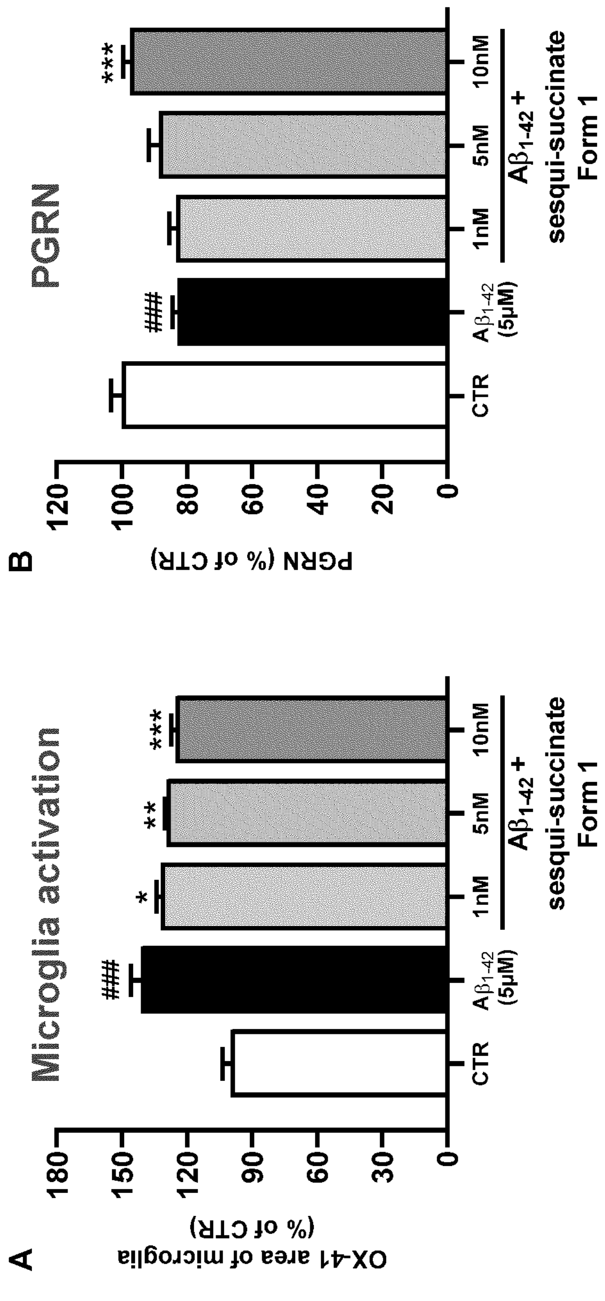

FIG. 26 shows the effects of N-(3-(4-(3-(diisobutylamino) propyl)piperazin-1-yl)propyl)-1H-benzo[d]imidazol-2-amine sesqui-succinate salt Form 1 on the activation of microglial cells (A) and PGRN release (B) in cortical neurons cultured with microglia after an Api-42 injury for 72 h. Results are expressed in percentage of control (CTR) condition as mean±SEM (n=4-6). One-way ANOVA followed by Fisher's test. *;  or * indicate p<0.05; p<0.01 or p<0.001 vs $A\beta_{1-42}$ or ###vs CTR, p<0.05 was considered significant.

Figure 27:
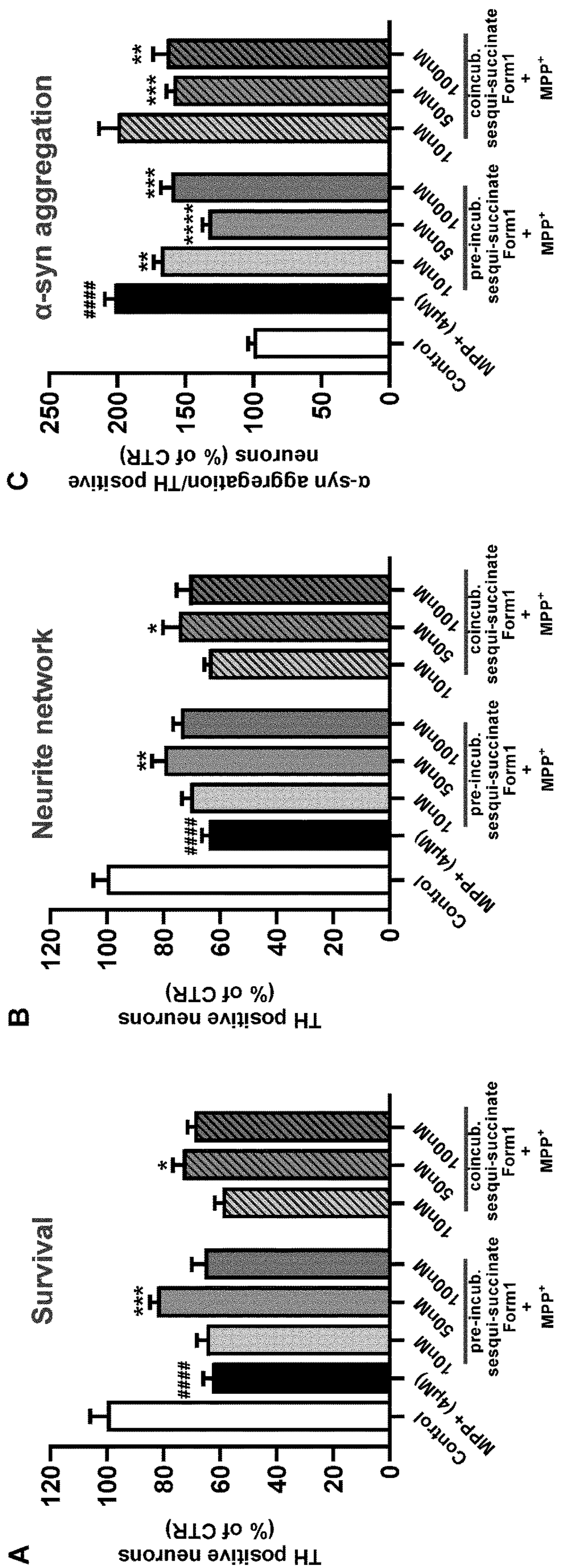

FIG. 27 shows the effects of pre or co-incubation of N-(3-(4-(3-(diisobutylamino)propyl)piperazin-1-yl)propyl)-1H-benzo[d]imidazol-2-amine sesqui-succinate salt Form 1 on the survival (A), the neurite network (B) and on α-synuclein aggregation (C) in primary mesencephalic neurons TH (+) after $MPP^+$ injury for 48 h. Results are expressed in percentage of control condition as mean±SEM (n=4-6). One-way ANOVA followed by Fisher's test. ####p<0.0001 vs control; *<0.05; p<0.01; *p<0.001 or ****p<0.0001 vs MPP*.

Figure 28:
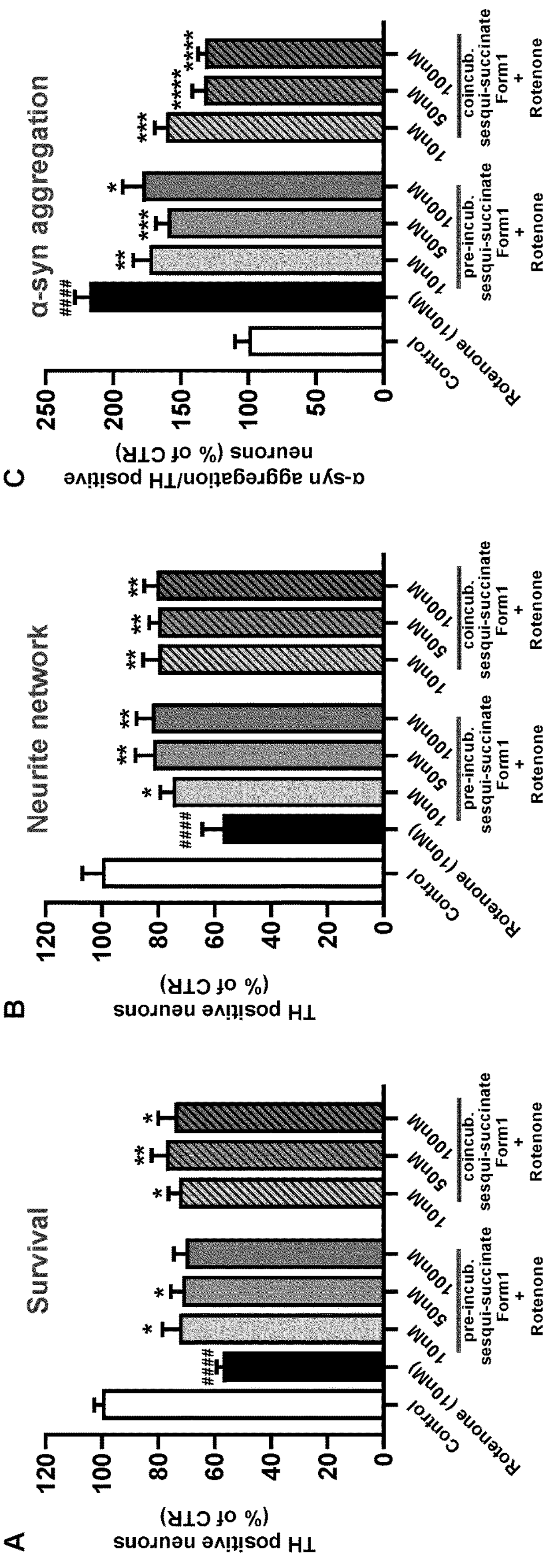

FIG. 28 shows the effects of pre or co-incubation of N-(3-(4-(3-(diisobutylamino)propyl)piperazin-1-yl)propyl)-1H-benzo[d]imidazol-2-amine sesqui-succinate salt Form 1 on the survival (A), the neurite network (B) and on α-synuclein aggregation (C) in primary mesencephalic neurons TH (+) after rotenone injury for 24 h. Results are expressed in percentage of control condition as mean±SEM (n=4-6). One-way ANOVA followed by Fisher's test. ####p<0.0001 vs control; *<0.05; p<0.01; *p<0.001 or ****p<0.0001 vs rotenone.

CHEMISTRY EXAMPLES

The following abbreviations are used throughout the present application: °C: Celsius degrees, $a_w$: water activity, DMSO: dimethylsulfoxyde, DSC: differential scanning calorimetry, GVS: gravimetric vapour sorption, δ: NMR chemical shifts expressed in ppm, eq: equivalent(s), EDTA: ethylenediamine tetra-acetic acid, eq.: equivalent(s), g: gram(s), h: hour(s), HDPE: high density polyethylene, HPLC: high performance liquid chromatography, Hz: Hertz, FT-IR: Fourier-transform infrared, L: liter(s), M: mol/L, mM: mmol/L, μM: mol/L, Me: methyl, MEK: methyl ethyl ketone, mg: milligram(s), MHz: megahertz, min: minute(s), mL: milliliter(s), mm: millimeter(s), mol: mole(s), mmol: millimole(s), pmol: micromole(s), $MPP^+$: 1-methyl-4-phenylpyridin-1-ium, nm: nanometer(s), NMR: nuclear magnetic resonance, PBS: phosphate-buffered saline, PLM: polarized light microscopy, PGRN: progranulin, ppm: party per million, RH: relative humidity, RPM: round(s) per minute, rt: retention time, RT: room temperature (ca 15-25 °C), s: second(s), TFA: trifluoroacetic acid, TG/DTA: thermogravimetric/differential thermal analysis, UV: ultraviolet, v: volume, VH-XRPD: Variable Humidity X-Ray Powder Diffraction, WB: western blot, XRPD: X-ray powder diffraction.

All reported temperatures are expressed in degrees Celsius (°C); all reactions were carried out at room temperature (RT) unless otherwise stated.

Experimental set-up or purification procedures that were used in this invention, when not described in specific details, are assumed to be known to those conversant in the art and are described in such standard reference manuals such as: i) Gordon, A. J.; Ford, R. A. "The Chemist's Companion—A Handbook of Practical Data, Techniques, and References", Wiley: New York, 1972; ii) Vogel's Textbook of Practical Organic Chemistry, Pearson Prentice Hall: London, 1989; iii) P. Heinrich Stahl and Camille G. Wernuth 'Handbook of Pharmaceutical Salts', Wiley VCH.

HPLC Analysis.

Method A:

Instrument: Dionex Ultimate 3000

Column: Supelco Ascentis Express C18 15×4.6 mm 2.7 m

Column Temperature: 50 °C

Autosampler Temperature: Ambient

UV wavelength: 275 nm

Injection Volume: 20 μL

Flow Rate: 1 mL/min

Mobile Phase A: 0.1% TFA in Water

Mobile Phase B: 0.1% TFA in Acetonitrile

Gradient program:

| Time (minutes) | Solvent B [%] |
|---|---|
| 0.0 | 5 |
| 30.0 | 60 |
| 33.0 | 60 |
| 33.1 | 5 |
| 40.0 | 5 |

Method B:

In a variant, HPLC analyses were carried out with the same parameters as above using a Zorbax Extend C18 150×4.6 mm 3.5 μm column.

NMR Analysis

NMR experiments were performed on a Bruker AVIIIHD spectrometer equipped with a DCH cryoprobe operating at 500.12 MHz for protons and carbons. Experiments were performed in deuterated DMSO and each sample was prepared to ca. 10 mM concentration. Further analysis was optionally performed in $D_2O$ and/or methanol-$d_4$. Chemical shifts are expressed in parts per million, (ppm, δ units). Coupling constants are expressed in Hz. Abbreviations for multiplicities observed in NMR spectra are as follows: s (singlet), d (doublet), t (triplet), q (quadruplet), m (multiplet), br (broad).

UV Analysis (For Capsule Blend Uniformity Only)

| | |
|---|---|
| Instrument | Thermo Scientific, Evolution 160 Uv-Visible Spectrophotometer |
| Scan | Wavelengths: 190 nm to 400 nm<br>Rate: 600 nm/min<br>Data integration: 1.0 nm |
| Fixed Wavelength | 280 nm |

Samples were measured using a quartz cuvette with a pathlength of 10 mm. Initially a UV scan was performed over the range 190 nm to 400 nm of solutions of salt with a concentration ca. 20 μg/mL prepared in water. The same solvent was used for a baseline correction. The fixed 280 nm wavelength was primarily used to confirm blend uniformity of the salt formulations.

X-ray Powder Diffraction (XRPD)

XRPD analysis was carried out on a PANalytical X'pert pro with PIXcel detector (128 channels), scanning the samples between 3 and 35° 2θ. The material was gently ground to release any agglomerates and loaded onto a multi-well plate with Mylar polymer film to support the sample. The multi-well plate was then placed into the diffractometer and analysed using Cu Kα radiation ($\alpha_1$ λ=1.54060 Å; $\alpha_2$=1.54443 Å; β=1.39225 Å; $\alpha_1$: $\alpha_2$ ratio=0.5) running in transmission mode (step size 0.0130° 2θ, step time 18.87s) using 40 kV/40 mA generator settings. Data were visualized and images generated using the HighScore Plus 4.7 desktop application (PANalytical, 2017).

Thermogravimetric/Differential Thermal Analysis (TG/DTA)

Approximately, 5 mg of material was weighed into an open aluminium pan and loaded into a simultaneous thermogravimetric/differential thermal analyzer (TG/DTA) and held at room temperature. The sample was then heated at a rate of 10 °C/min from 20 °C to 300 °C during which time the change in sample weight was recorded along with any differential thermal events (DTA). Nitrogen was used as the purge gas, at a flow rate of 300 $cm^3$/min.

Differential Scanning Calorimetry (DSC)

Approximately, 5 mg of material was weighed into an aluminium DSC pan and sealed non-hermetically with a pierced aluminium lid. The sample pan was then loaded into a Seiko DSC6200 (equipped with a cooler) cooled and held at 20 °C. Once a stable heat-flow response was obtained, the sample and reference were heated up to 180 °C at a rate of 10 °C/min and the resulting heat flow response monitored. Nitrogen was used as the purge gas, at a flow rate of 50 $cm^3$/min.

Infrared Spectroscopy (IR)

Infrared spectroscopy was carried out on a Bruker ALPHA P spectrometer. Sufficient material was placed onto the center of the plate of the spectrometer and the spectra were obtained using the following parameters:

Resolution: 4 $cm^{-1}$
Background Scan Time: 16 scans
Sample Scan Time: 16 scans
Data Collection: 4000 to 400 $cm^{-1}$
Result Spectrum: Transmittance
Software: OPUS version 6

Gravimetric Vapour Sorption (GVS)

Approximately 10-20 mg of sample was placed into a mesh vapour sorption balance pan and loaded into an IGASorp Moisture Sorption Analyser balance by Hiden Analytical. The sample was subjected to a ramping profile from 40-90% relative humidity (RH) at 10% increments, maintaining the sample at each step until a stable weight had been achieved (98% step completion, minimum step length 30 minutes, maximum step length 60 minutes) at 25 °C. After completion of the sorption cycle, the sample was dried using the same procedure to 0% RH, and finally taken back to the starting point of 40% RH. Two cycles were performed. The weight change during the sorption/desorption cycles were plotted, allowing for the hygroscopic nature of the sample to be determined.

Dynamic Vapour Sorption (DVS)

Approximately 10-20 mg of sample was placed into a mesh vapour sorption balance pan and loaded into an Intrinsic dynamic vapour sorption balance by Surface Measurement Systems. The sample was subjected to a ramping profile from 40-90% relative humidity (RH) at 10% increments, maintaining the sample at each step until a stable weight had been achieved (dm/dt 0.004%, minimum step length 30 minutes, maximum step length 500 minutes) at 25 °C. After completion of the sorption cycle, the sample was dried using the same procedure to 0% RH and then a second sorption cycle back to 40% RH. Two cycles were performed. The weight change during the sorption/desorption cycles were plotted, allowing for the hygroscopic nature of the sample to be determined. XRPD analysis was then carried out on any solid retained.

Variable Humidity X-Ray Powder Diffraction (VH-XRPD)

VH-XRPD analysis was carried out on a Philips X'Pert Pro Multipurpose diffractometer equipped with a humidity chamber. The samples were scanned between 4 and 35.99°2θ using Cu K radiation (αλ=1.54060 Å; $\alpha_2$=1.54443 Å; β=1.39225 Å; $\alpha_1$: $\alpha_2$ ratio=0.5) running in Bragg-Brentano geometry (step size 0.008°2θ) using 40 kV/40 mA generator settings. Measurements were performed at 50%, 60%, 70%, 80%, 90%. The sample was held at 90% for an hour and 30 minutes. Measurements were taken at 30-minute intervals.

Solvents and reagents were purchased and used as received from commercial vendors unless otherwise specified.

Example 1: Synthesis and Characterisation of Form 1: Crystalline Form of N-(3-(4-(3-(diisobutylamino)propyl)piperazin-1-yl)propyl)-1H-benzo[d]imidazol-2-amine Sesqui-Succinate Salt 514.6 mg of N-(3-(4-(3-(diisobutylamino)propyl)piperazin-1-yl)propyl)-1H-benzo[d]imidazol-2-amine was weighed out in a 20 mL scintillation vial. 10 mL of methyl ethyl ketone (99% pure) was added to the vial which was stirred at 40 °C using a temperature-controlled block, a stirrer plate, and magnetic needle. No clear solution was observed so further 5 mL of MEK was added to aid dissolution at 40 °C. A clear solution was obtained; the clear solution at 40 °C was polish-filtered using PTFE filter (0.45 microns) and a syringe. The filtered solution was added back to a clean 20 mL scintillation vial and re-heated to 40 °C. 142.5 mg of succinic acid (1 mole equivalent) was added to the vial. A clear solution was initially observed. After stirring at 40 °C for 30 minutes, crystallization of material was observed. The experiment was temperature cycled between 40 °C and 5 °C in 3-hour cycles for 20 hours. At 5 °C, the slurry was filtered using Buchner flask and funnel using grade 1 Whatman filter paper (pore size=11 m) under vacuum. The wet cake was washed with 2.5 mL of chilled (5 °C) MEK and dried under reduced pressure at 40 °C for 2 hours. The dried isolated solid was analysed by XRPD, TG/DTA and HPLC. The filtered mother liquor was analysed for concentration by HPLC.

An isolated yield of 78.5% was achieved, with an HPLC yield of 93.5% determined based on the mother liquor concentration (see Table 1).

TABLE 1

| Results from Form 1 succinate salt preparation | | | | | | |
|---|---|---|---|---|---|---|
| Solvent system | Input Free Base (mg) | Yields (%) Theoretical | Yields (%) Isolated | Solid purity % Area | Losses to mL's (mg/mL) | Losses to wash (mg/mL) |
| Methyl ethyl ketone | 514 | 93.5 | 78.5 | 99.2 | 11.1 | 5.5 |

Figure 7:
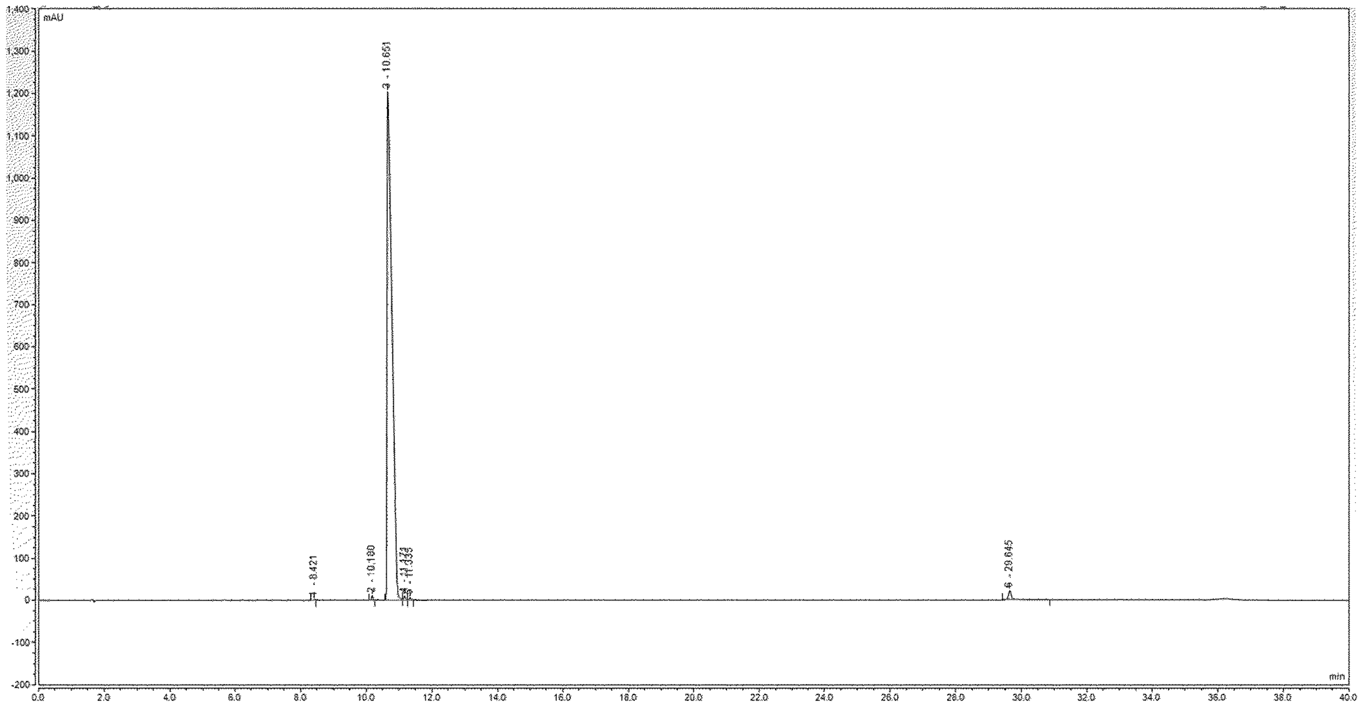
FIG. 7 shows the HPLC chromatogram of Form 1, crystalline form of N-(3-(4-(3-(diisobutylamino)propyl)piperazin-1-yl)propyl)-1H-benzo[d]imidazol-2-amine sesqui-succinate salt.

HPLC (method A) indicated a purity of 99.2%; rt=10.65 min (FIG. 7).

The XRPD 2θ diffractogram showed the material to be crystalline (FIG. 3) and comprised peaks at diffraction angles of 2θ=3.8°±0.2° (100%), 10.3°±0.2° (11.3%), 12.4°±0.2° (6.8%), 16.2°±0.2° (23.5%), 17.9°±0.2° (11.9%), 19.8°±0.2° (10.2%), 20.4°±0.2° (13.0%), 23.8°±0.2° (23.3%) and 26.7°±0.2° (9.8%) when irradiated with a CuKα light source.

Figure 8:
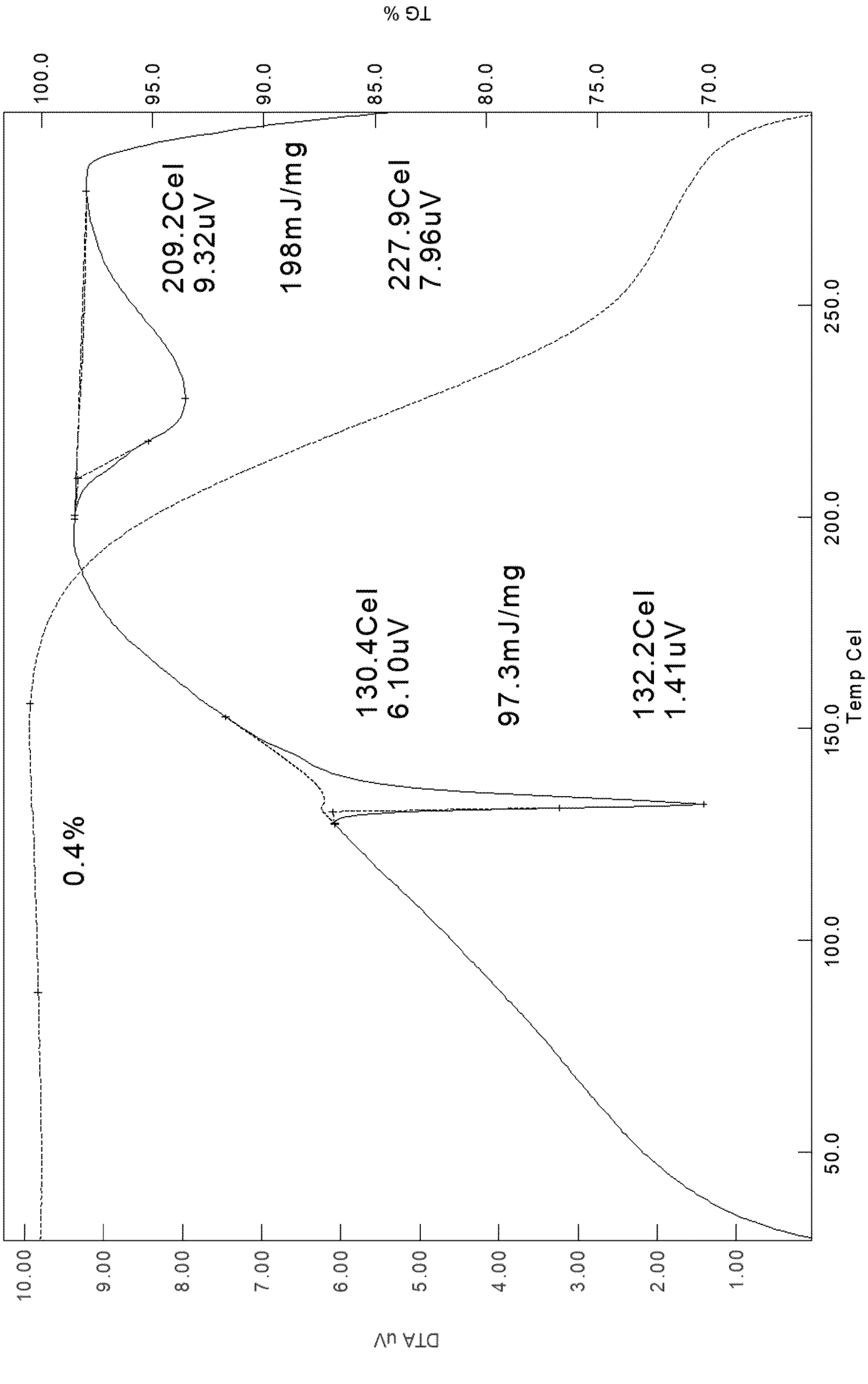
FIG. 8 shows the TG/DT thermogram of Form 1, crystalline form of N-(3-(4-(3-(diisobutylamino)propyl)piperazin-1-yl)propyl)-1H-benzo[d]imidazol-2-amine sesqui-succinate salt.

TG trace showed a weight loss of 0.4% from heating onset up to ca. 160 °C which is due to surface moisture. DT trace showed an endothermic event with an onset of ca. 130 °C (peak at 132 °C) which is due to a melt event. A broad endothermic event was also observed at onset ca. 209 °C (peak of ca. 228 °C) after the melt; this is associated with decomposition (FIG. 8). Another batch of N-(3-(4-(3-(diisobutylamino)propyl)piperazin-1-yl)propyl)-1H-benzo[d]imidazol-2-amine, sesqui-succinate salt was made and further characterized by HPLC, XRPD, DSC, GVS, FT-IR, NMR and VH-XRPD.

HPLC (method A) indicated a purity of 98.4%.

Figure 1:
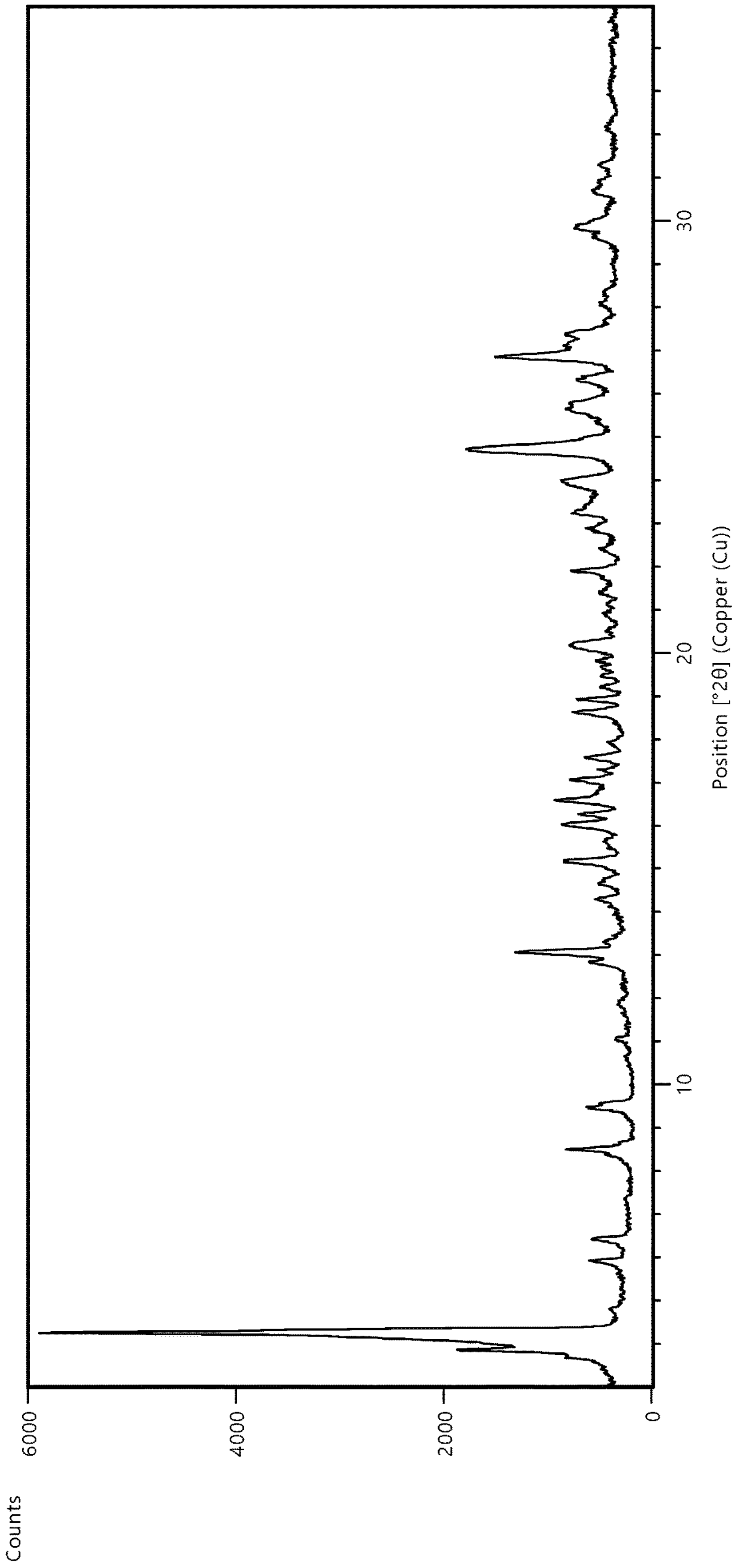
FIG. 1 shows the XRPD 2θ diffractogram of Form A, crystalline form of N-(3-(4-(3-(diisobutylamino)propyl)piperazin-1-yl)propyl)-1H-benzo[d]imidazol-2-amine di-sulphate salt.
Figure 2:
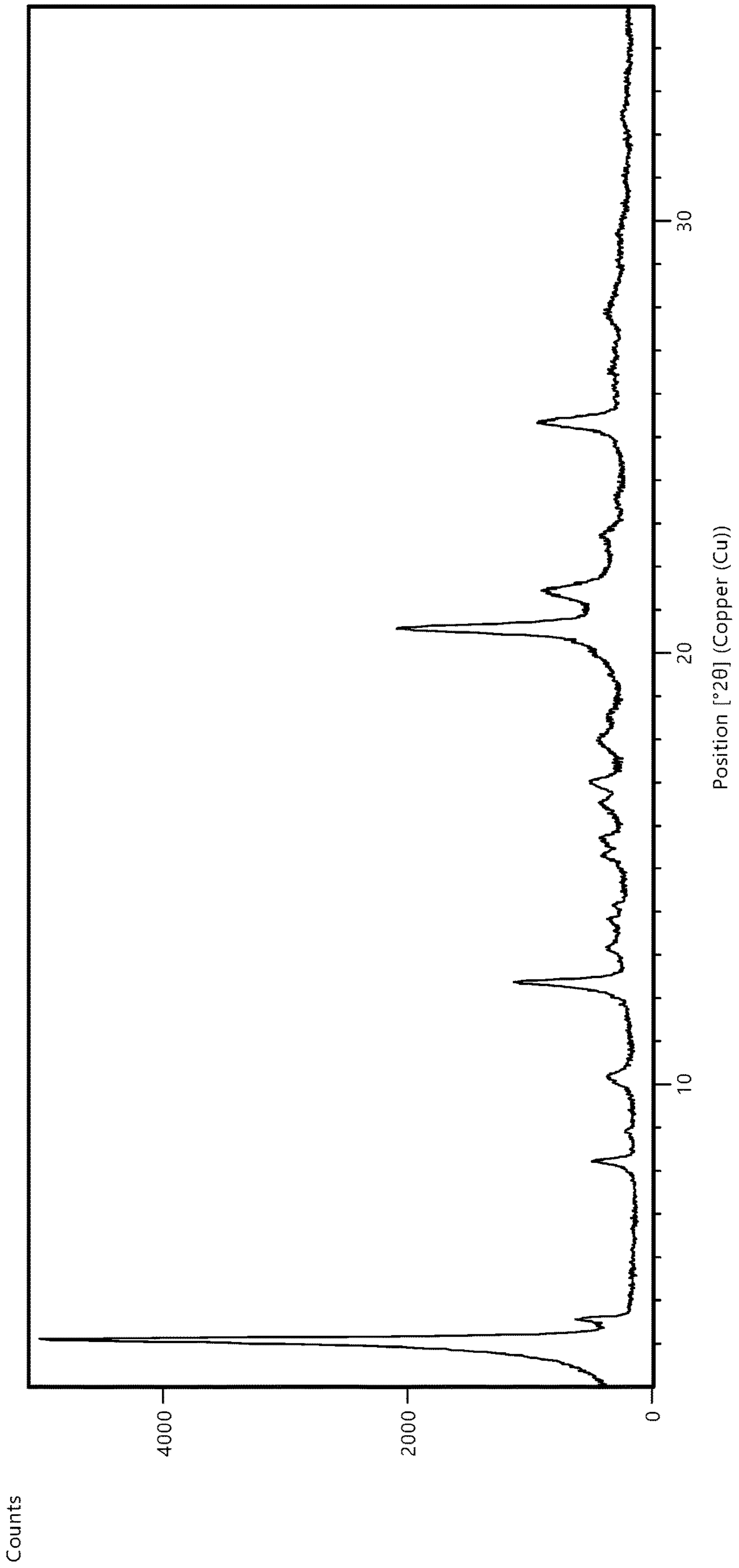
FIG. 2 shows the XRPD 2θ diffractogram of Form B, crystalline form of N-(3-(4-(3-(diisobutylamino)propyl)piperazin-1-yl)propyl)-1H-benzo[d]imidazol-2-amine di-sulphate salt.
Figure 3:
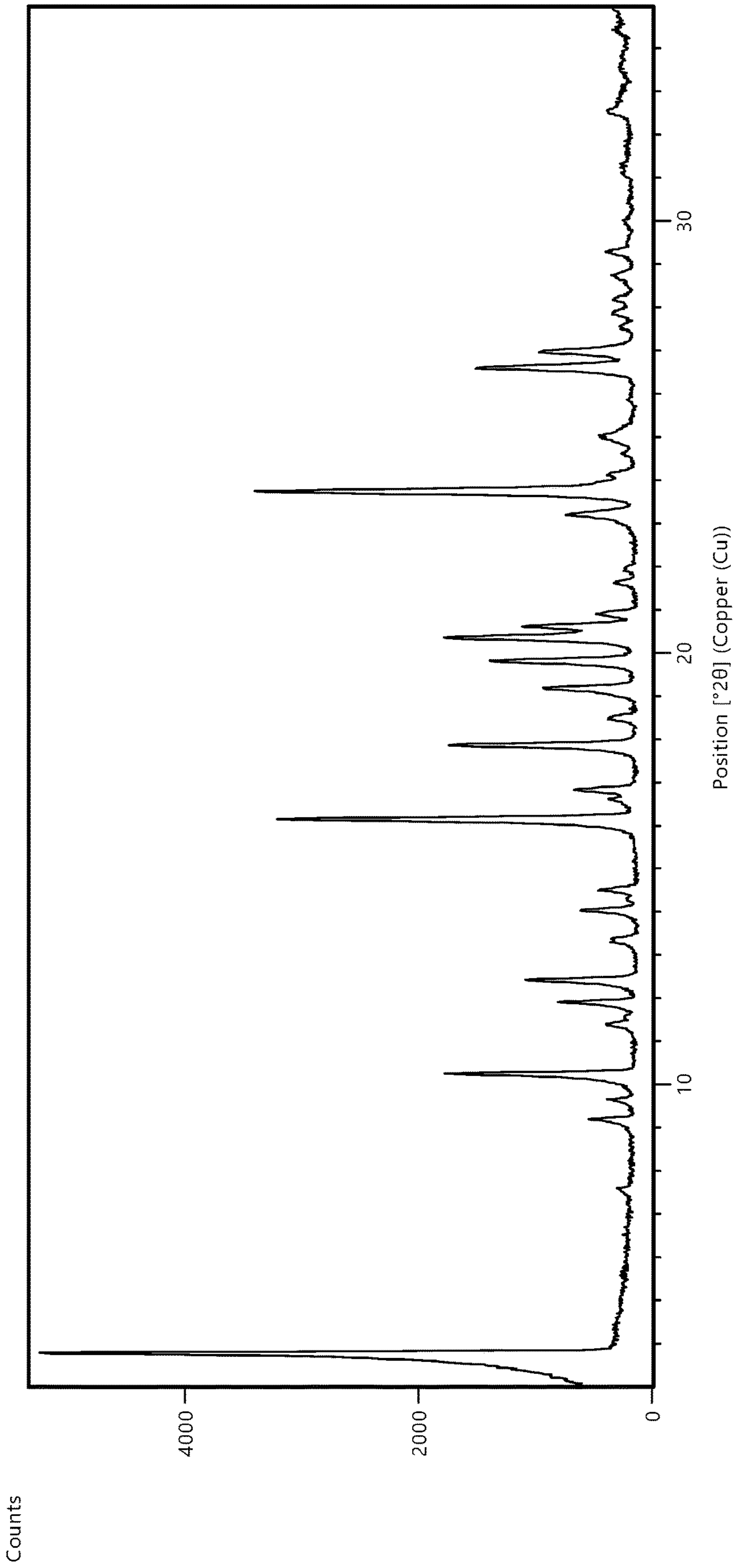
FIG. 3 shows the XRPD 2θ diffractogram of Form 1, crystalline form of N-(3-(4-(3-(diisobutylamino)propyl)piperazin-1-yl)propyl)-1H-benzo[d]imidazol-2-amine sesqui-succinate salt.
Figure 12:
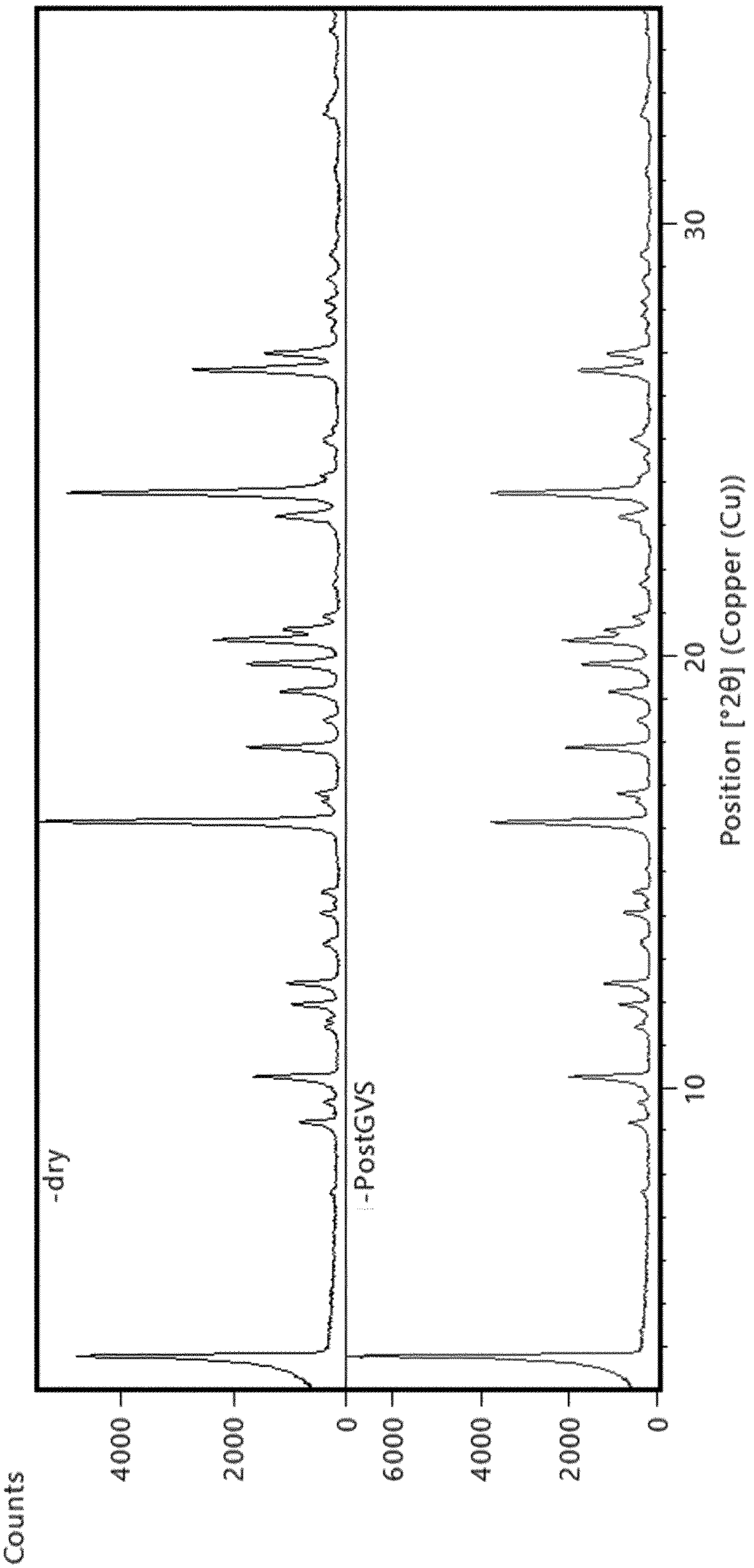
FIG. 12 shows the post-GVS XRPD 2θ diffractograms of Form 1, crystalline form of N-(3-(4-(3-(diisobutylamino)propyl)piperazin-1-yl)propyl)-1H-benzo[d]imidazol-2-amine sesqui-succinate salt.

XRPD 2θ diffractogram was identical to that of previously described batch (see FIG. 12 top graph in reference to FIG. 3).

Figure 9:
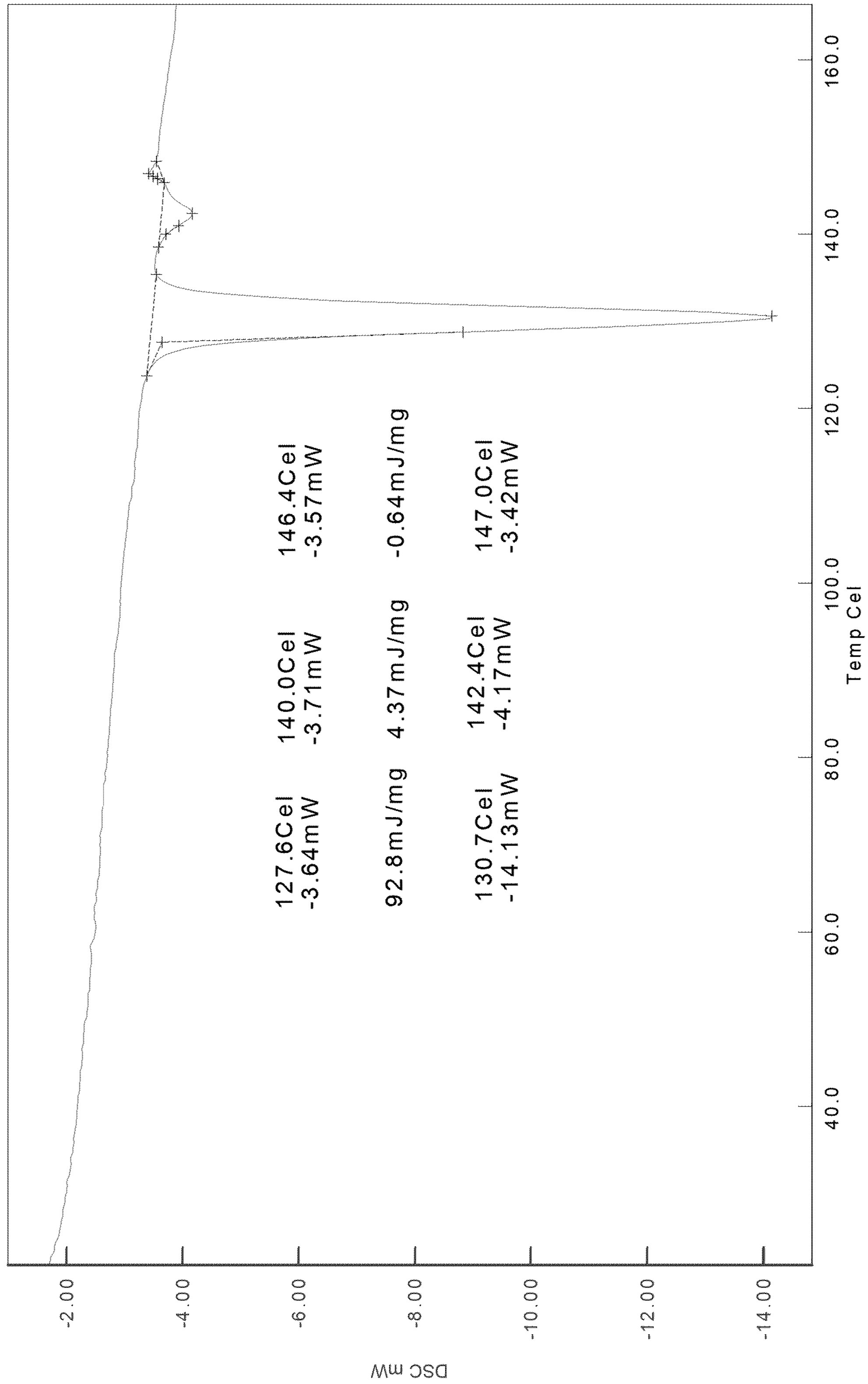
FIG. 9 shows the DSC thermogram of Form 1, crystalline form of N-(3-(4-(3-(diisobutylamino)propyl)piperazin-1-yl)propyl)-1H-benzo[d]imidazol-2-amine sesqui-succinate salt (First Heating Cycle).

DSC in the first heating cycle showed a sharp endothermic event with an onset of ca. 128 °C with a peak at 131 °C. This is followed by a small exothermic event with a peak at 142 °C and then a smaller exothermic event with peak at 147 °C (FIG. 9); DSC analysis in the first cooling and second heating cycle showed no significant events in the thermograms.

Figure 10:
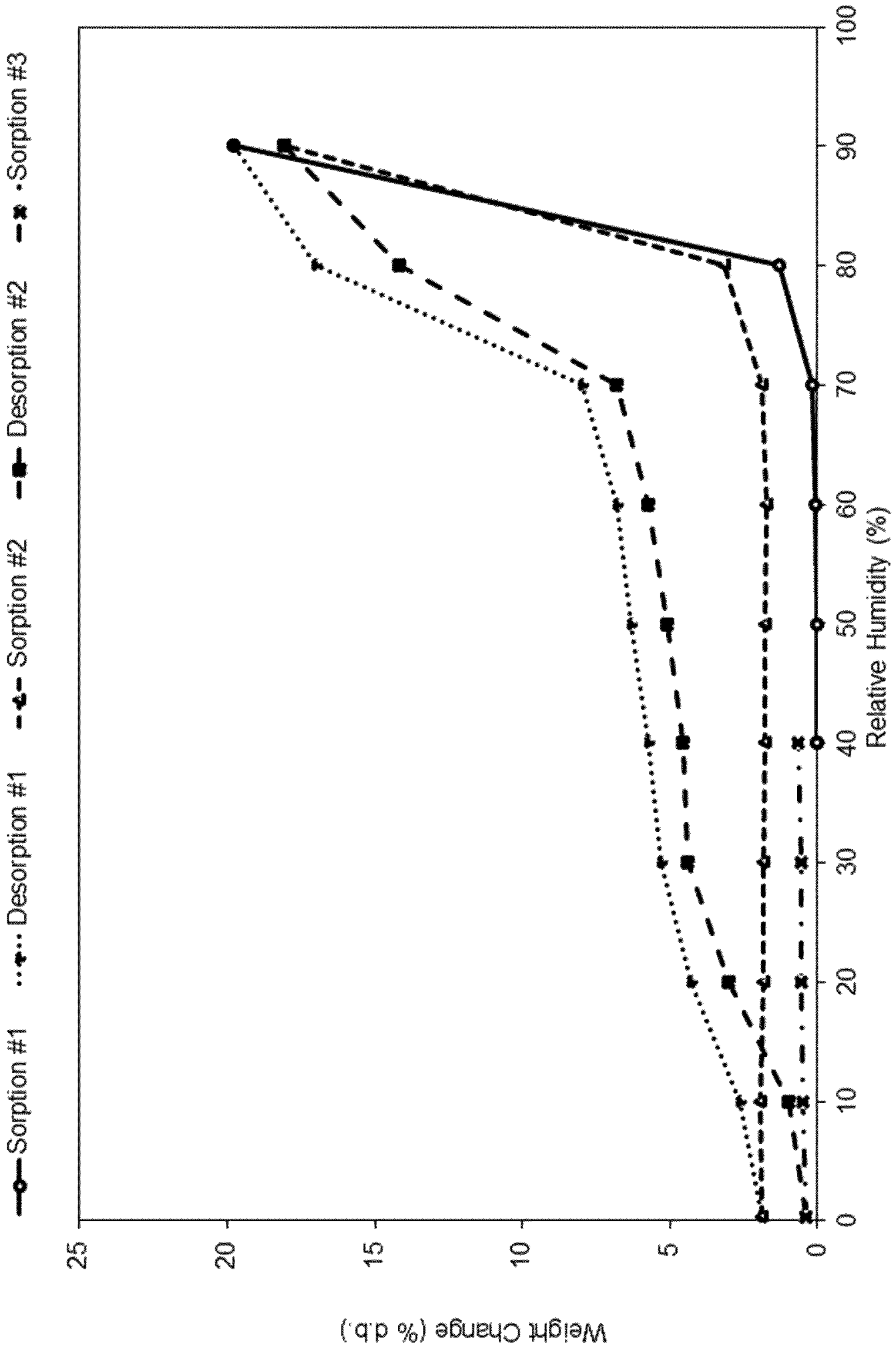
FIG. 10 shows the GVS Isotherm Plot of Form 1, crystalline form of N-(3-(4-(3-(diisobutylamino)propyl)piperazin-1-yl)propyl)-1H-benzo[d]imidazol-2-amine sesqui-succinate salt.
Figure 11:
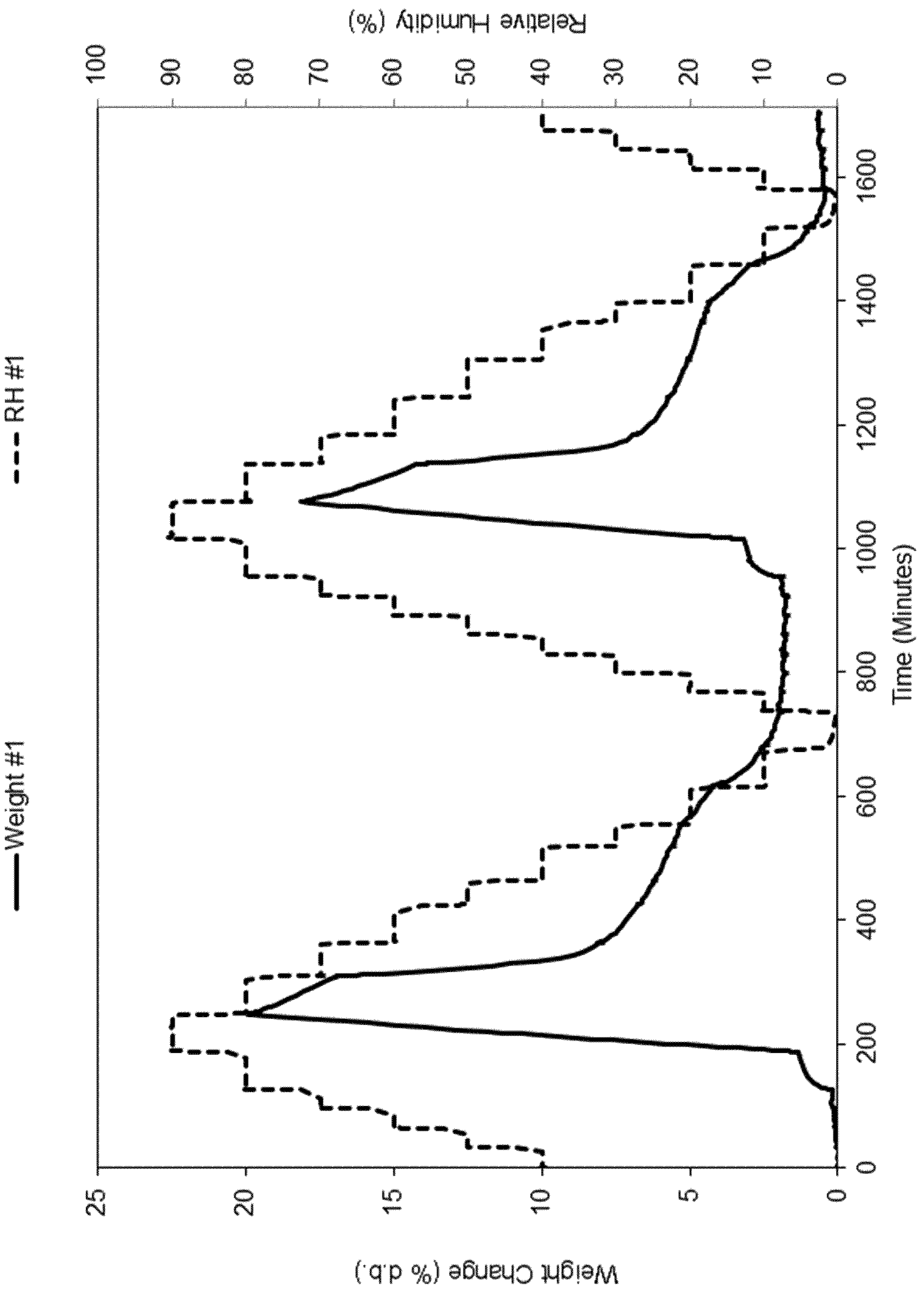
FIG. 11 shows the GVS Kinetic Plot of Form 1, crystalline form of N-(3-(4-(3-(diisobutylamino)propyl)piperazin-1-yl)propyl)-1H-benzo[d]imidazol-2-amine sesqui-succinate salt.

By GVS analysis, the material was found to take up ca. +0.1 wt. % at 70% RH which is followed by a sharp increase of ca. +18.9 wt. % (approximately 7.1 equiv. water) up to 90% RH. At this stage, it is likely that a channel hydrate may be formed. This is then lost readily down to 70% RH and gradually down to 0% RH (FIG. 10). The GVS kinetic plot can be found in FIG. 11 which showed the rapid increase in weight between 70 and 90% RH. Post-GVS XRPD analysis found the material to remain as the same crystalline form after exposure to GVS humidity conditions (FIG. 12: top: XRPD of material; bottom: XRPD of material post-GVS).

Figure 13:
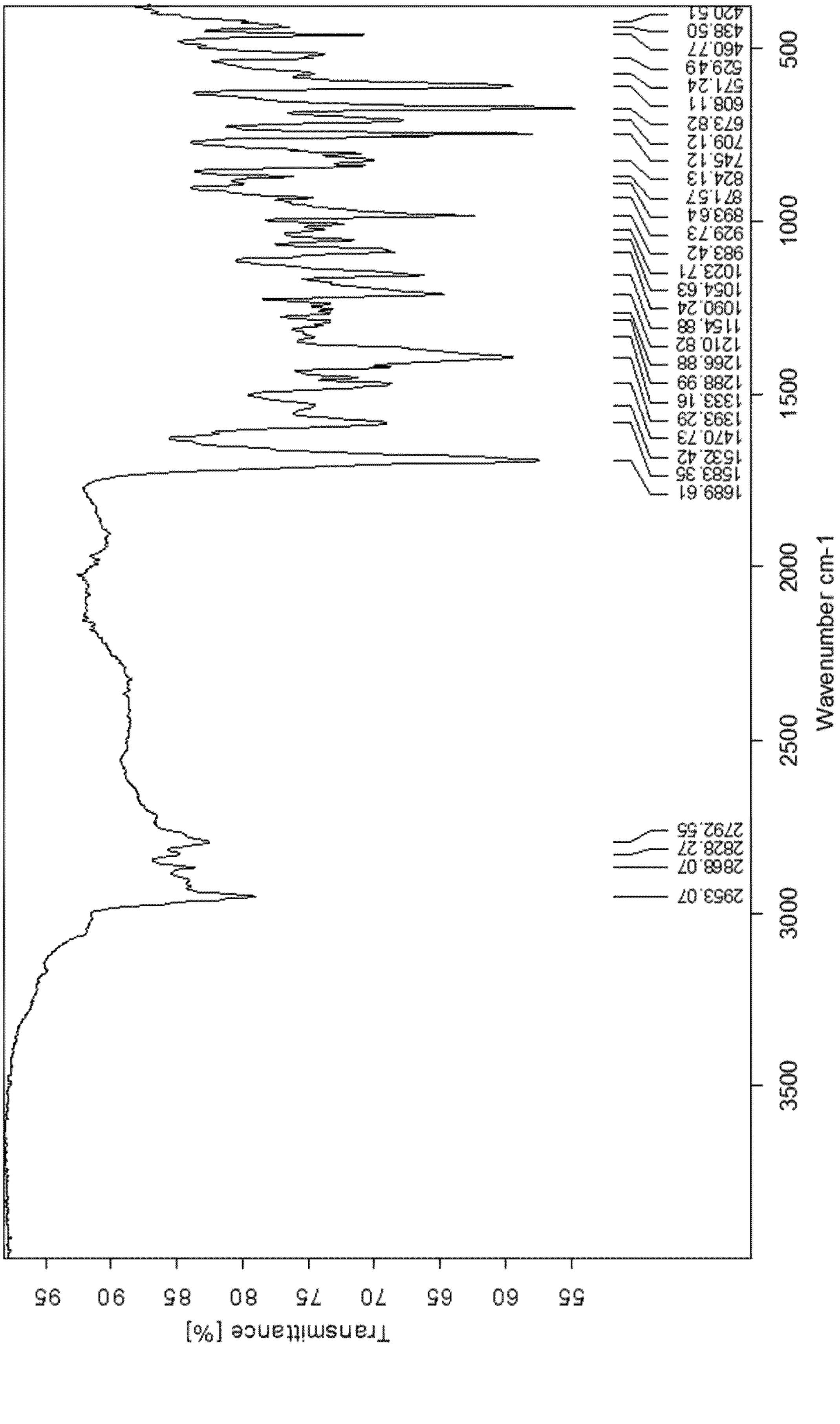
FIG. 13 shows the FT-IR spectrum of Form 1, crystalline form of N-(3-(4-(3-(diisobutylamino)propyl)piperazin-1-yl)propyl)-1H-benzo[d]imidazol-2-amine sesqui-succinate salt.

The FT-IR spectrum is presented in FIG. 13.

Figure 14:
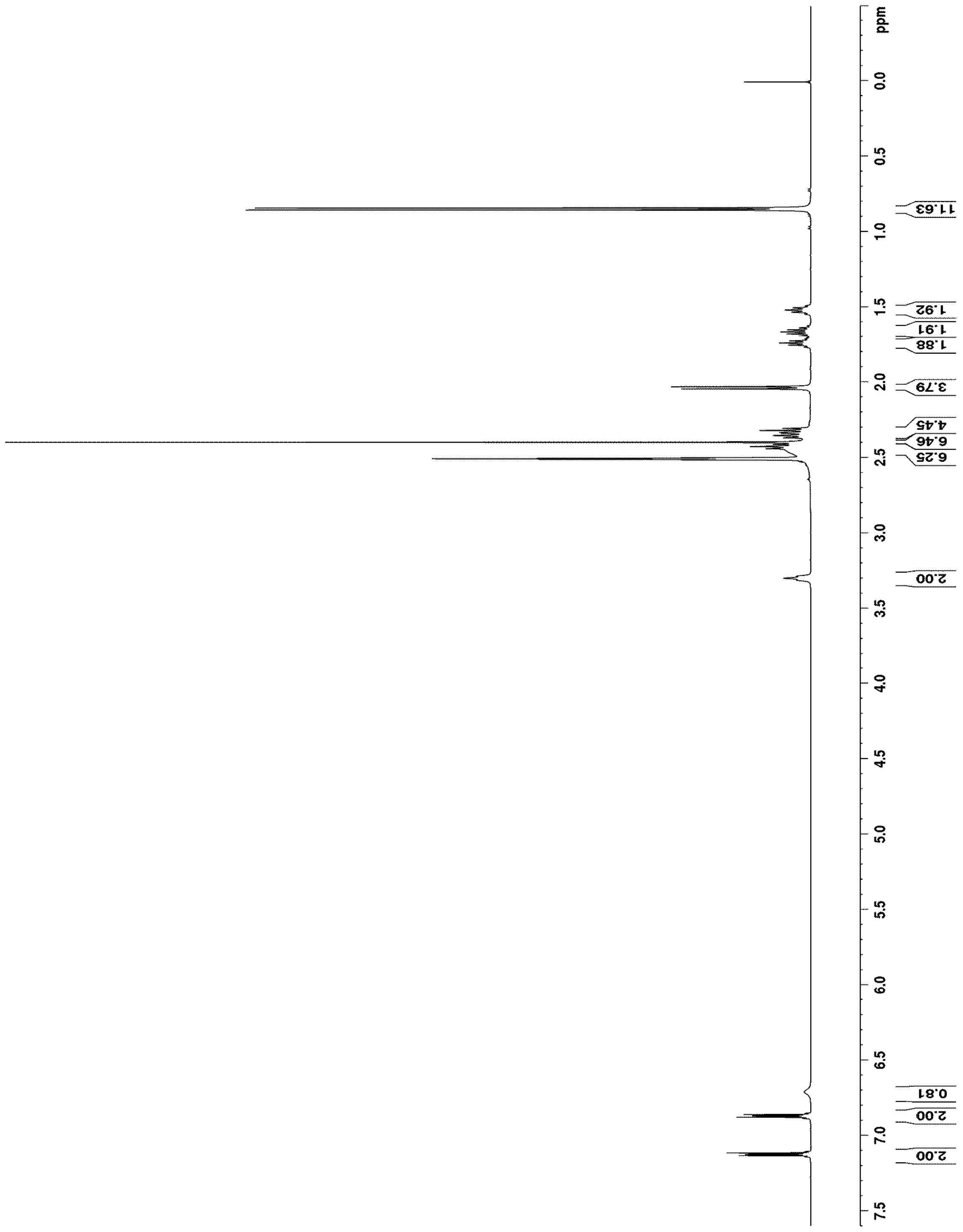
FIG. 14 shows the $^1$H-NMR spectrum of Form 1, crystalline, form of N-(3-(4-(3-(diisobutylamino)propyl)piperazin-1-yl)propyl)-1H-benzo[d]imidazol-2-amine sesqui-succinate salt (DMSO-$d_6$, 500.12 MHz).
Figure 15:
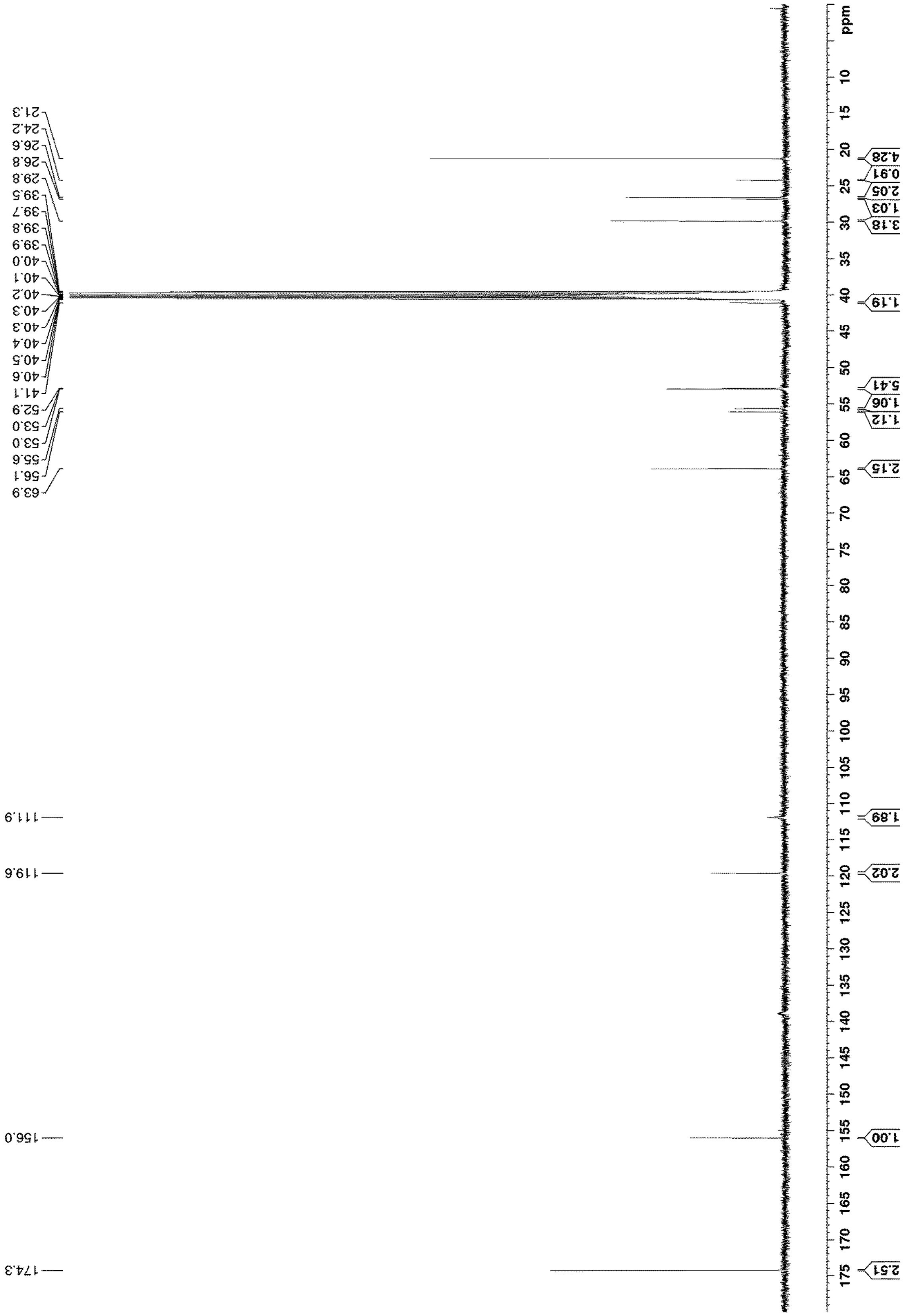
FIG. 15 shows the $^{13}$C Quant-NMR Spectrum of Form 1, crystalline form of N-(3-(4-(3-(diisobutylamino)propyl)piperazin-1-yl)propyl)-1H-benzo[d]imidazol-2-amine sesqui-succinate salt (DMSO-$d_6$, 500.12 MHz).

$^{1}H$ and quantitative $^{13}C$ NMR spectra in DMSO-$d_6$ are presented in FIG. 14 and FIG. 15 respectively.

$^{1}H$ NMR spectrum (500.12 MHz-DMSO-$d_6$): δ (ppm): 7.13 (2H dd J1=6 Hz, J2=3 Hz), 6.87 (2H dd J1=6 Hz, J2=3 Hz), 6.71 (1H br s), 3.30 (2H t J=7 Hz), 2.42 (6H m, 2.33 4H dt J1=16 Hz, J2=7 Hz), 2.04 (4H d J=7 Hz), 1.74 (2H quintet J=7 Hz), 1.67 (2H septet J=7 Hz), 1.52 (2H quintet J=7 Hz), 0.85 (12H d J=7 Hz) ppm.

Quantitative $^{13}C$ NMR spectrum (121.16 MHz-DMSO-$d_6$): δ (ppm): 174.3, 156.0, 119.5, 111.9, 63.9 56.1, 55.6, 53.0 (d), 29.8, 26.8, 26.6, 24.2, 21.3. Quantitative $^{13}C$ NMR confirmed the stoichiometry and successful formation of a sesqui-succinate salt.

VH-XRPD up to 90% RH of the sesqui-succinate Form 1 was found to remain the same crystalline form with no change to crystallinity or form after exposure to 90% RH for up to 1 hour and 30 minutes.

7-Day Stability Tests 7-day stability tests were carried out as follows: 15 mg of salt was weighed into ×3 2 mL vials. The vials were then placed at 40 °C/75% RH, 80 °C and under ambient light; after 1 week, the solids were analysed by XRPD and HPLC purity (method A).

Figure 16:
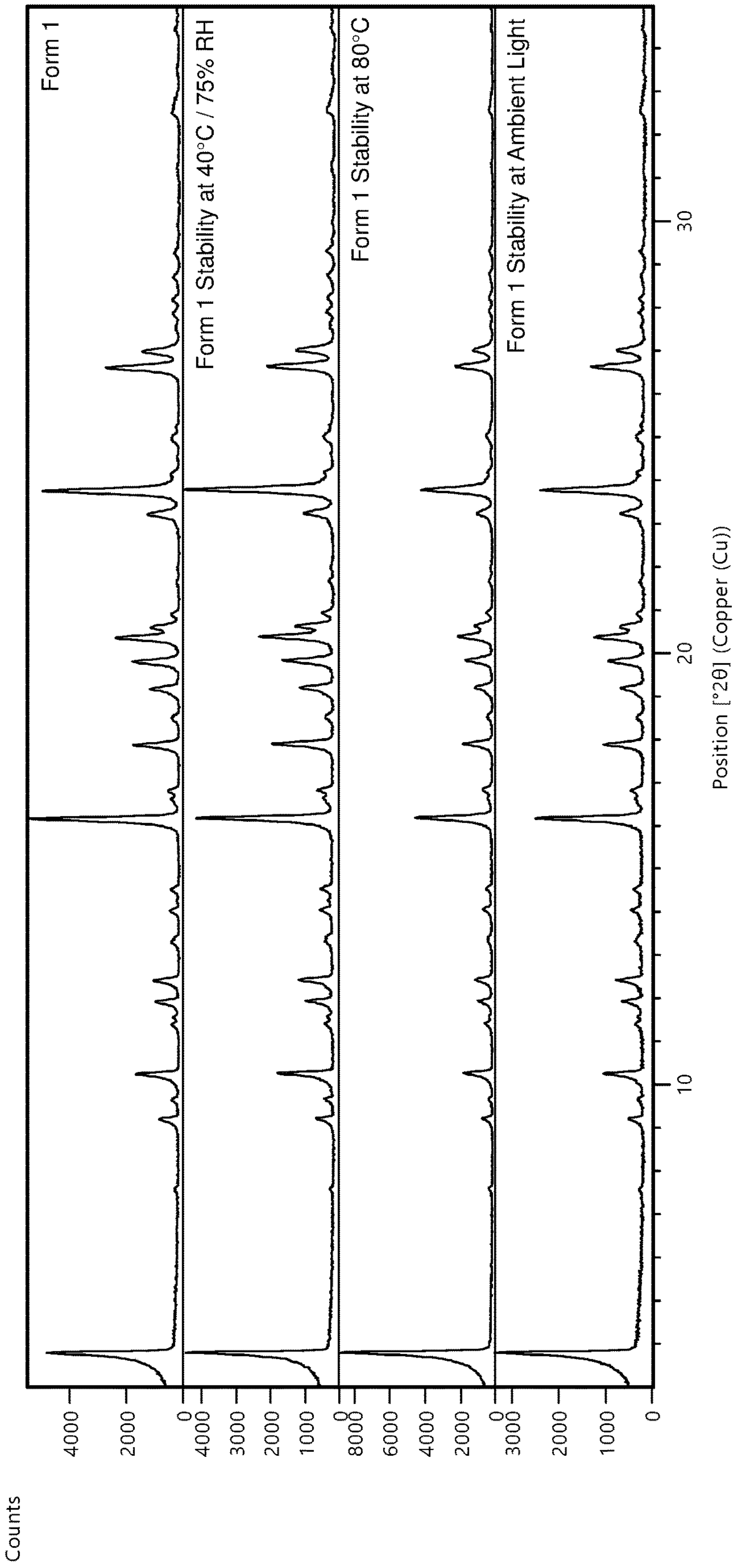
FIG. 16 shows the XRPD 29 diffractograms of Form 1, crystalline form of N-(3-(4-(3-(diisobutylamino)propyl)piperazin-1-yl)propyl)-1H-benzo[d]imidazol-2-amine sesqui-succinate salt from 7-day stability tests.

XRPD analysis of solids recovered after 7-day stability tests (at 40 °C/75% RH, 80 °C and ambient light) showed no change to crystallinity or form after exposure to these conditions (FIG. 16).

HPLC analysis (method A) of solids recovered from the 7-day stability test showed no change in purity at each stability condition. The values are reported in Table 2.

TABLE 2

| HPLC Purity Values of Sesqui-Succinate Form 1-7 Day Stability Tests | |
|---|---|
| Condition | Purity (%) |
| 40° C./75% RH | 98.5 |
| 80° C. | 98.3 |
| Ambient Light | 98.4 |

Solubility Experiments

A solubility assessment in unbuffered water showed the material to be highly soluble with a value of >500 mg/mL. A pH measurement was taken to give a value of 5.28.

Approximately 20 mg of N-(3-(4-(3-(diisobutylamino)propyl)piperazin-1-yl)propyl)-1H-benzo[d]imidazol-2-amine, sesqui-succinate salt Form 1 was weighed into 3×2 mL vials. 100 μL of the appropriate buffer was added to form a slurry. Results are listed in Table 3.

TABLE 3

| Sesqui-Succinate Form 1 Solubility Values | |
|---|---|
| pH Buffer | Solubility (mg/mL) |
| 1.2 HCl | >213 |
| 4.5 citrate | >176 |
| 6.8 phosphate | >182 |

Synthesis Scale-Ups

Figure 17:
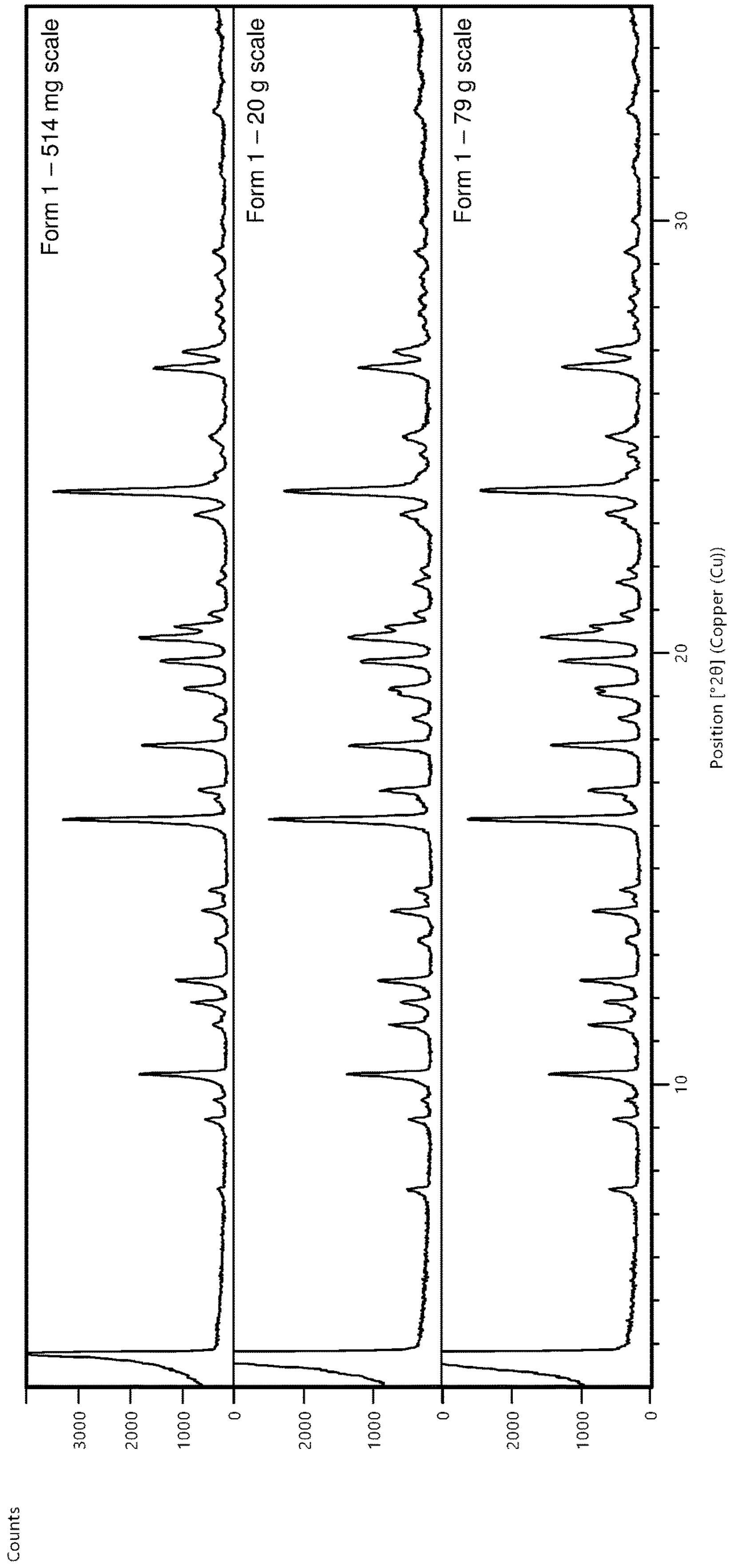
FIG. 17 shows overlays of XRPD 29 diffractograms of batches of Form 1, crystalline form of N-(3-(4-(3-(diisobutylamino)propyl)piperazin-1-yl)propyl)-1H-benzo[d]imidazol-2-amine sesqui-succinate salt.

The same experimental conditions were used for the synthesis of two further batches of this sesqui-succinate salt Form 1 starting from 20 g and 79 g of free base. Purities of said batches checked by HPLC (method A) were ≥99% with yields of 69% and 73% respectively. Overlays of XRPD 2θ diffractograms of all batches (514 mg, 20 g and 79 g scales) are presented in FIG. 17.

N-(3-(4-(3-(diisobutylamino)propyl)piperazin-1-yl)propyl)-1H-benzo[d]imidazol-2-amine, sesqui-succinate salt Form 1 was obtained reproducibly on multigram scale with a one-pot salt formation/crystallization in good yields. The sesqui-succinate salt Form 1 is very stable (purity and polymorphic form), highly crystalline, highly soluble, not hygroscopic up to 90% relative humidity, stable under stressed conditions. Therefore, this product is a suitable API and is especially of interest for solid formulations.

Example 2: Synthesis and Characterisation of Form 2: Crystalline Form of N-(3-(4-(3-(diisobutylamino)propyl)piperazin-1-yl)propyl)-1H-benzo[d]imidazol-2-amine Tris-Succinate Salt 10 mg of N-(3-(4-(3-(diisobutylamino)propyl)piperazin-1-yl)propyl)-1H-benzo[d]imidazol-2-amine was weighed into a 1.5 mL vial and the minimum amount of ethanol was added to achieve complete dissolution of the free base. 2 eq. of succinic acid was added using a 0.5 M stock solution (596.41 mg succinic acid dissolved in 10 mL ethanol). The vial was temperature cycled between ambient and 40 °C (4 hour cycles) with agitation for 6 days. Precipitation was observed and the solids were isolated by centrifugation filtration and then dried at 40 °C under vacuum for ca. 24 hours. The solid was analysed by HPLC, XRPD, TG/DT, DSC, DVS, FT-IR, NMR and VH-XRPD.

HPLC (method A) indicated a purity of 99.9%.

Figure 4:
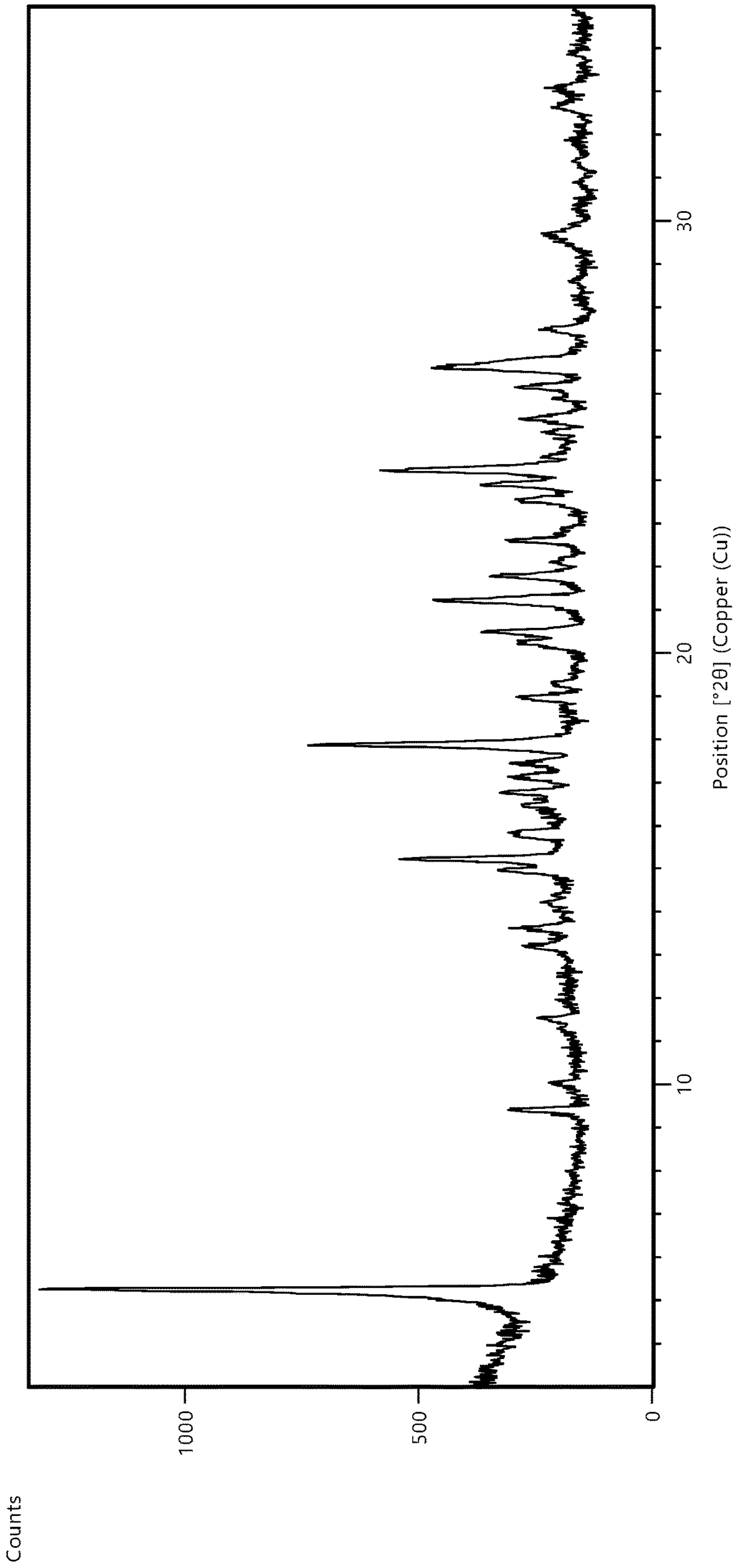
FIG. 4 shows the XRPD 2θ diffractogram of Form 2, crystalline form of N-(3-(4-(3-(diisobutylamino)propyl)piperazin-1-yl)propyl)-1H-benzo[d]imidazol-2-amine tris-succinate salt.
Figure 5:
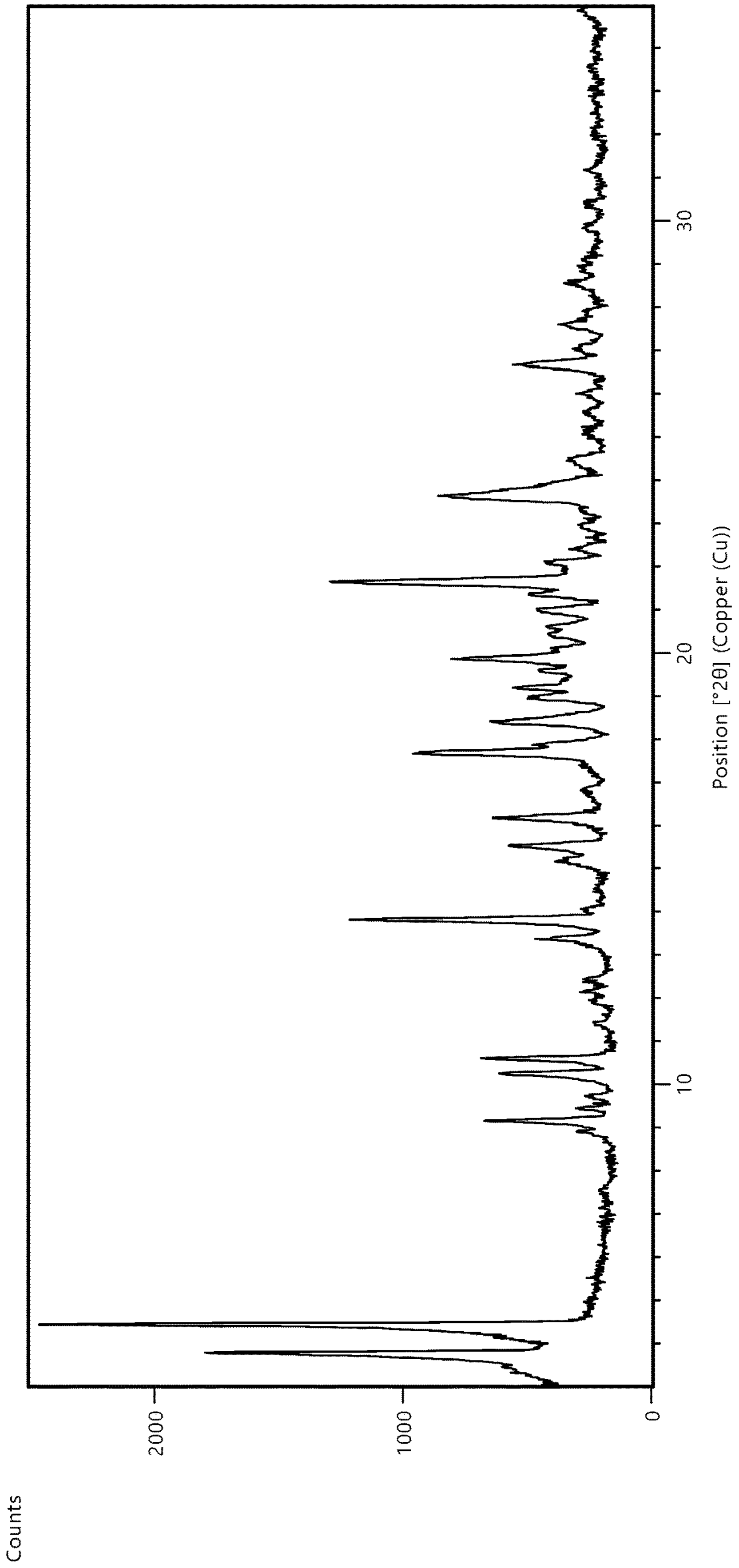
FIG. 5 shows the XRPD 2θ diffractogram of a crystalline form of N-(3-(4-(3-(diisobutylamino)propyl)piperazin-1-yl)propyl)-1H-benzo[d]imidazol-2-amine sequi-succinate salt hemi-hydrate (0.5 eq. of water).
Figure 6:
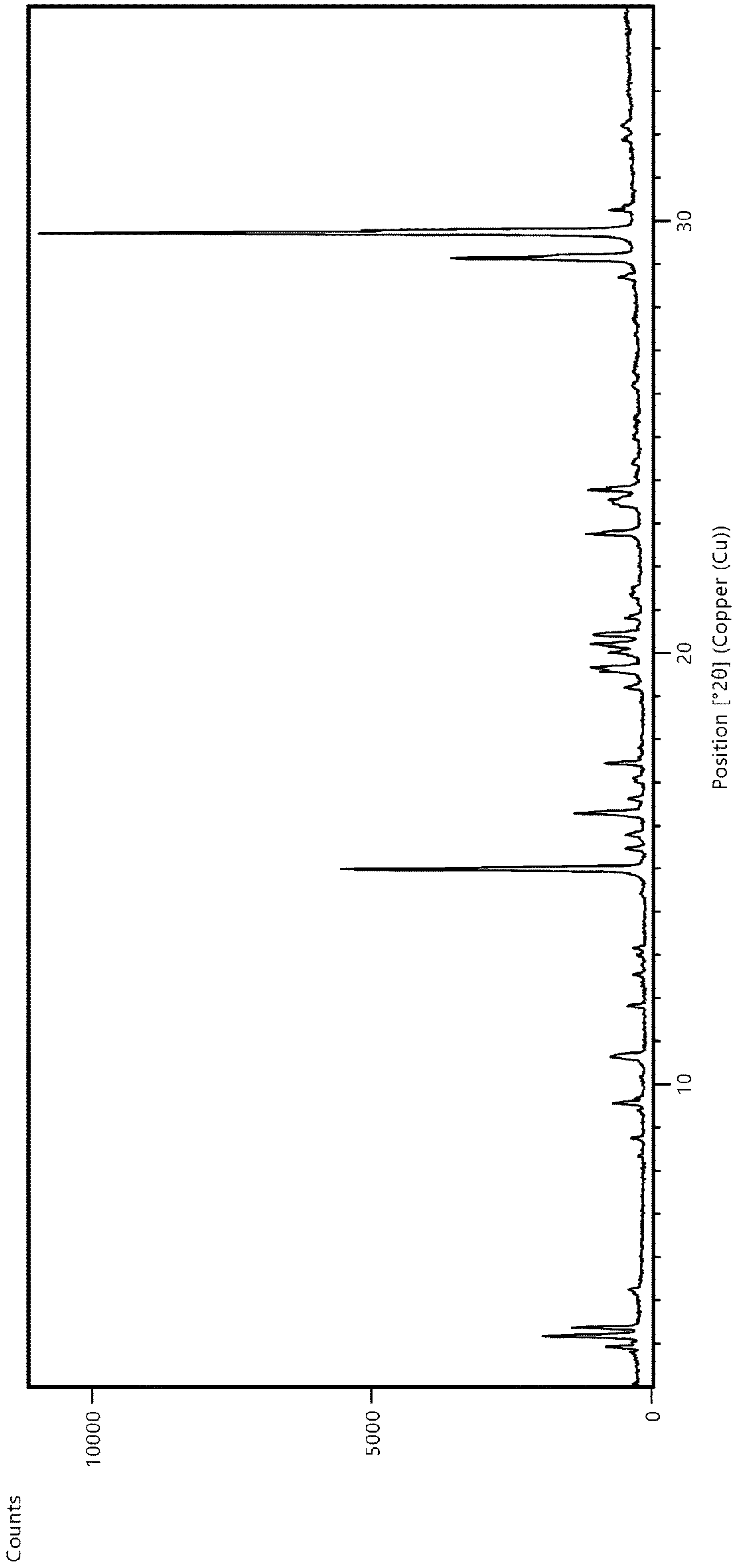
FIG. 6 shows the XRPD 2θ diffractogram of a crystalline form of N-(3-(4-(3-(diisobutylamino)propyl)piperazin-1-yl)propyl)-1H-benzo[d]imidazol-2-amine sesqui-succinate salt mono-hydrate (1.1 eq. of water).

The XRPD 2θ diffractogram showed the material to be crystalline (see FIG. 4) and comprised peaks at diffraction angles of 2θ=5.3°±0.2° (100%), 15.0°±0.2° (26.7%), 15.3°±0.2° (57.4%), 16.8°±0.2° (25.3%), 17.9°±0.2° (92.3%), 20.5°±0.2° (30.1%), 21.2°±0.2° (25.5%), 23.9°±0.2° (24.2%), 24.3°±0.2° (65.3%) and 26.6°±0.2° (31.5%) when irradiated with a CuKα light source.

Figure 18:
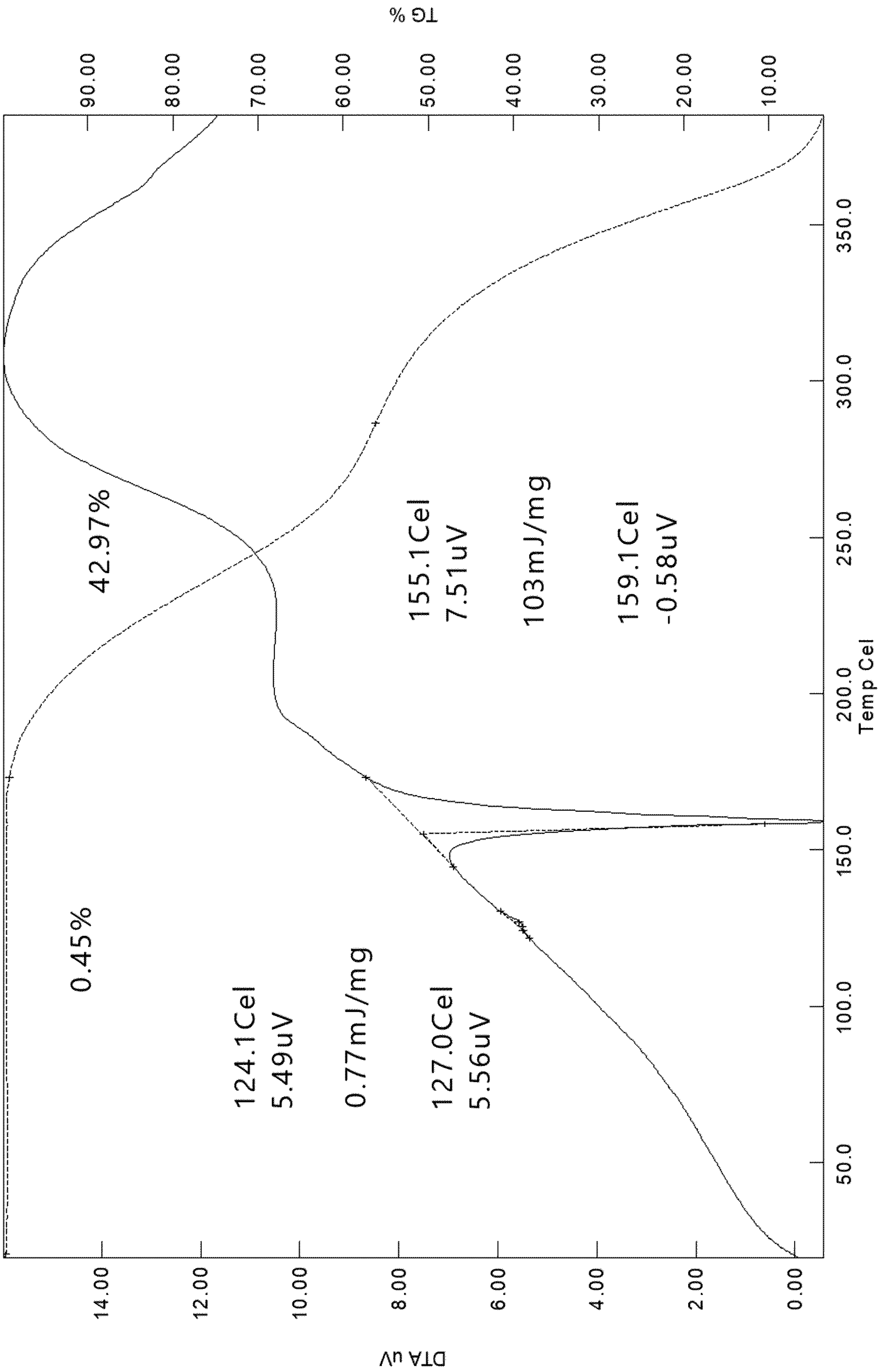
FIG. 18 shows the TG/DT thermogram of Form 2, crystalline form of N-(3-(4-(3-(diisobutylamino)propyl)piperazin-1-yl)propyl)-1H-benzo[d]imidazol-2-amine tris-succinate salt.

The TG trace from the TG/DT analysis (see FIG. 18) showed no mass loss up to 150 °C indicating the material did not contain residual solvents. A mass loss relating to salt dissociation was observed at temperatures above 150 °C. The DT trace showed an endothermic event relating to the coupled dissociation/melting of the salt form with an onset of ca. 155.1 °C (peak 159.1 °C).

Figure 19:
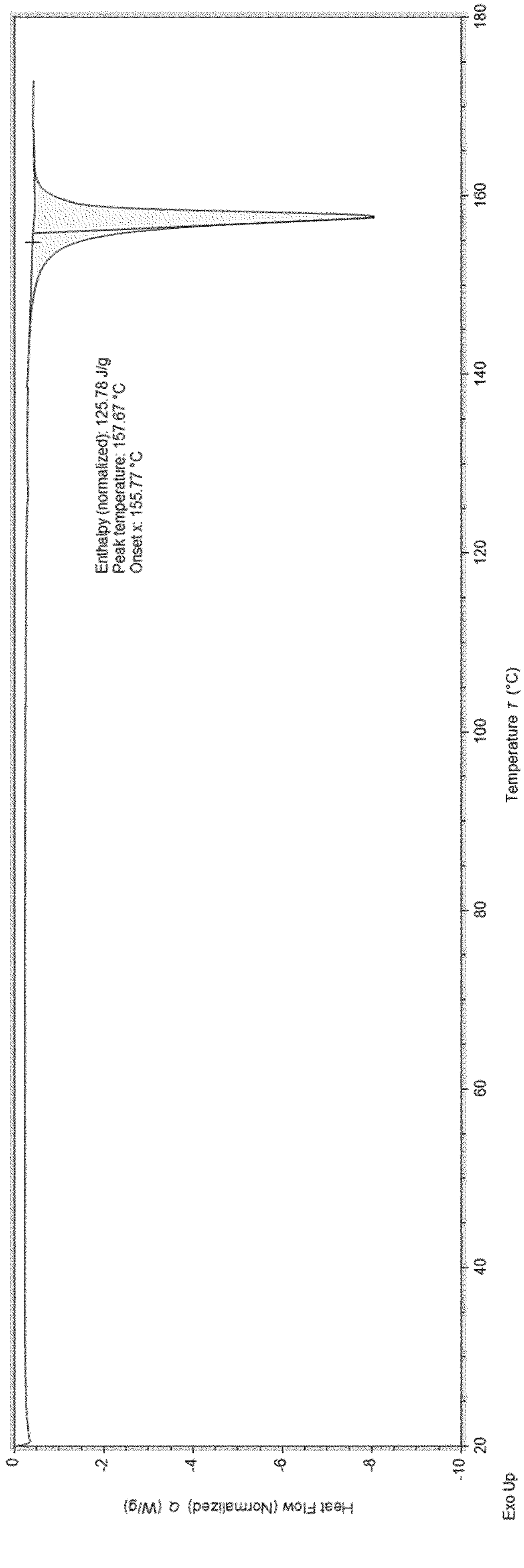
FIG. 19 shows the DSC thermogram of Form 2, crystalline form of N-(3-(4-(3-(diisobutylamino)propyl)piperazin-1-yl)propyl)-1H-benzo[d]imidazol-2-amine tris-succinate salt.

The DSC thermogram (see FIG. 19) showed tris-succinate Form 2 to melt with an onset of ca. 155.8 °C (peak 157.7 °C).

Figure 20:
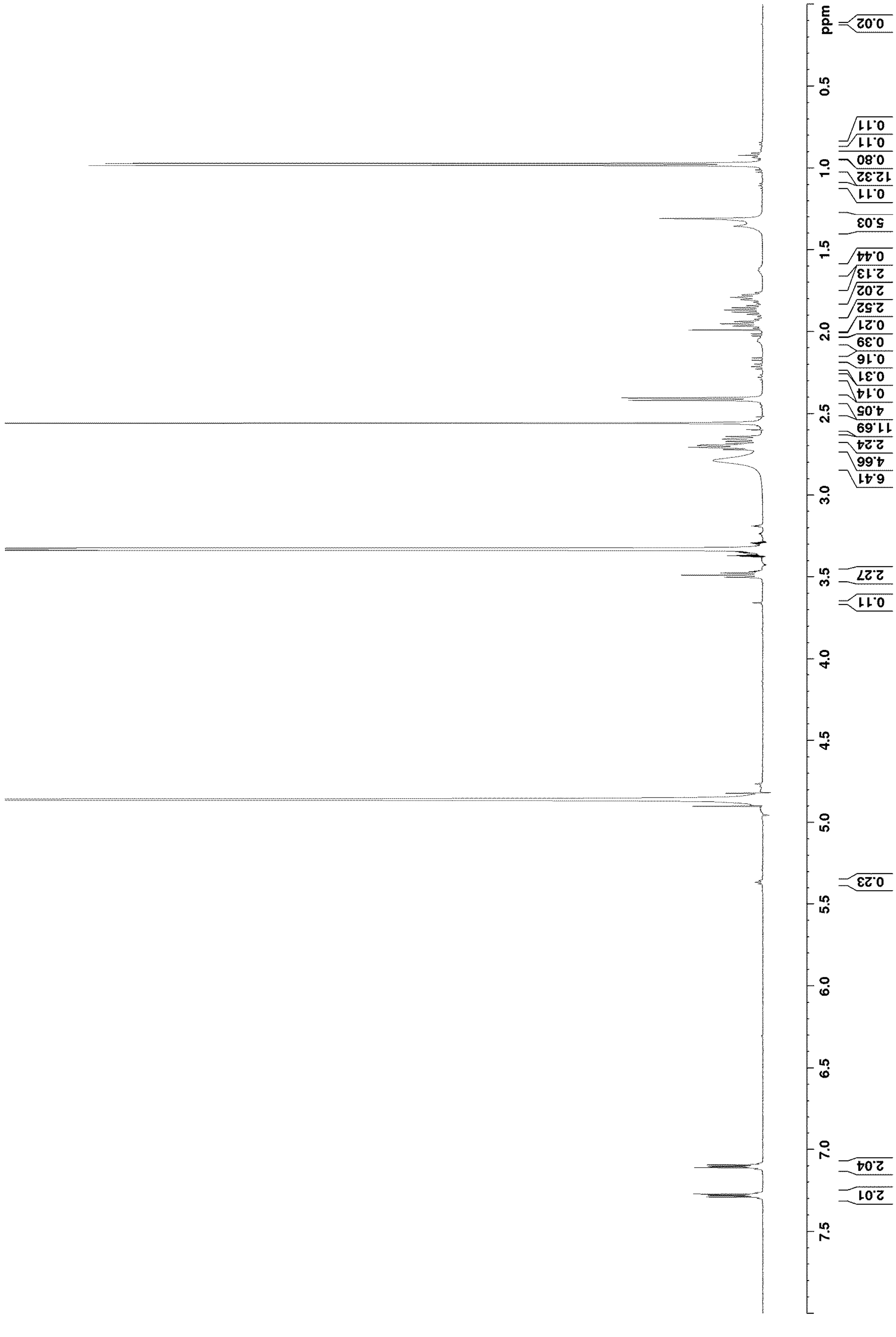
FIG. 20 shows the $^1$H-NMR spectrum of Form 2, crystalline form of N-(3-(4-(3-(diisobutylamino)propyl)piperazin-1-yl)propyl)-1H-benzo[d]imidazol-2-amine tris-succinate salt (MeOH-$d_4$, 500.12 MHz)

$^1$H NMR taken in MeOH-$d_4$ confirmed the salt to contain three equivalents of succinic acid (see FIG. 20).

$^1$H NMR spectrum (500.12 MHz-MeOH-$d_4$): δ (ppm): 7.28 (2H dd J1=6 Hz, J2=3 Hz), 7.10 (2H dd J1=6 Hz, J2=3 Hz), 3.48 (2H t J=7 Hz), 2.78 (6H br s), 2.67 (7H m), 2.56 (12H s), 2.41 (4H d J=7 Hz), 1.95 (2H quintet J=7 Hz), 1.87 (2H septet J=7 Hz), 1.79 (2H sextet J=7.4 Hz), 1.33 (5H br m), 0.97 (12H d J=6.7 Hz) ppm.

Figure 21:
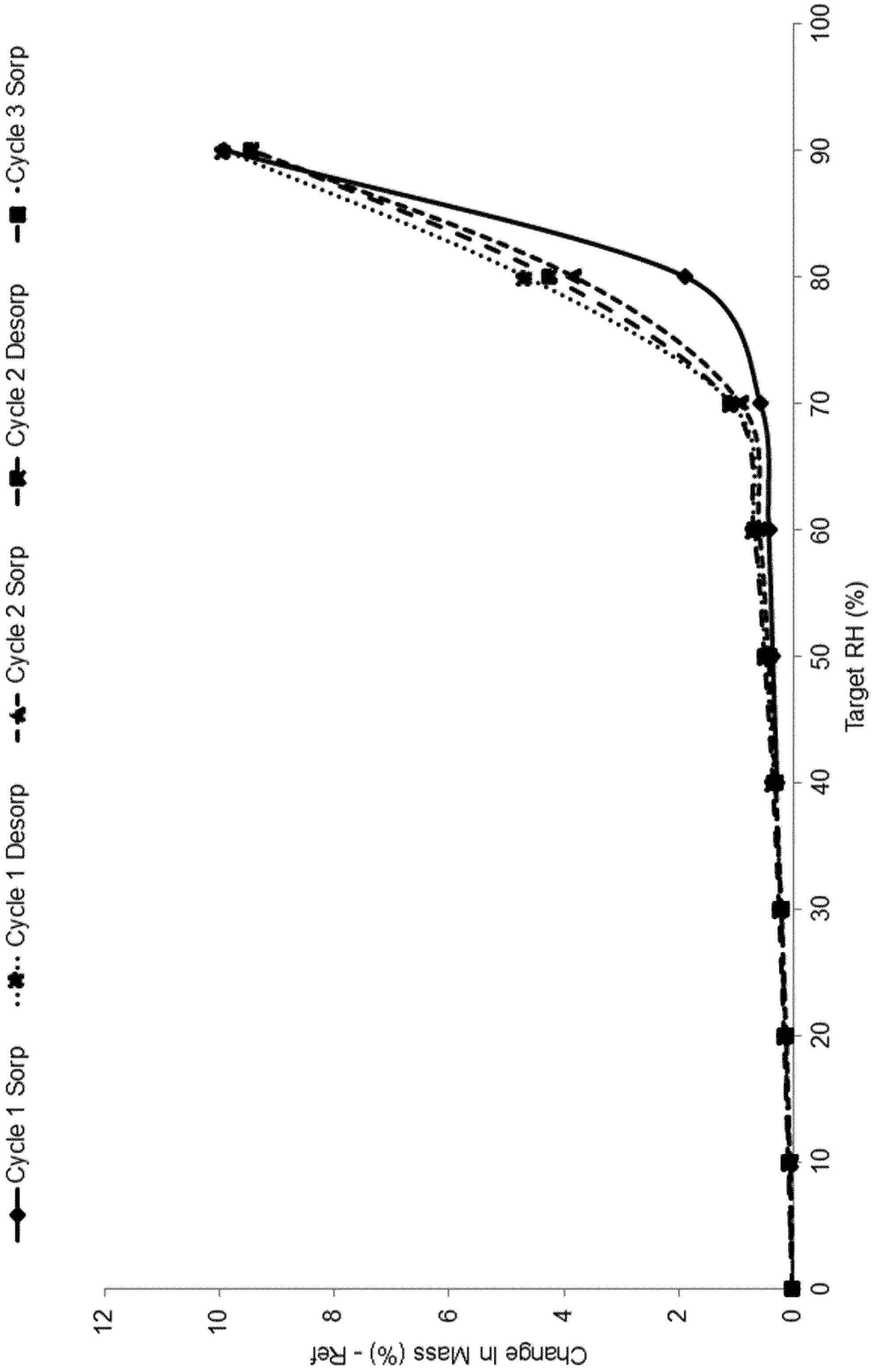
FIG. 21 shows the DVS Isotherm Plot of Form 2, crystalline form of N-(3-(4-(3-(diisobutylamino)propyl)piperazin-1-yl)propyl)-1H-benzo[d]imidazol-2-amine tris-succinate salt.
Figure 22:
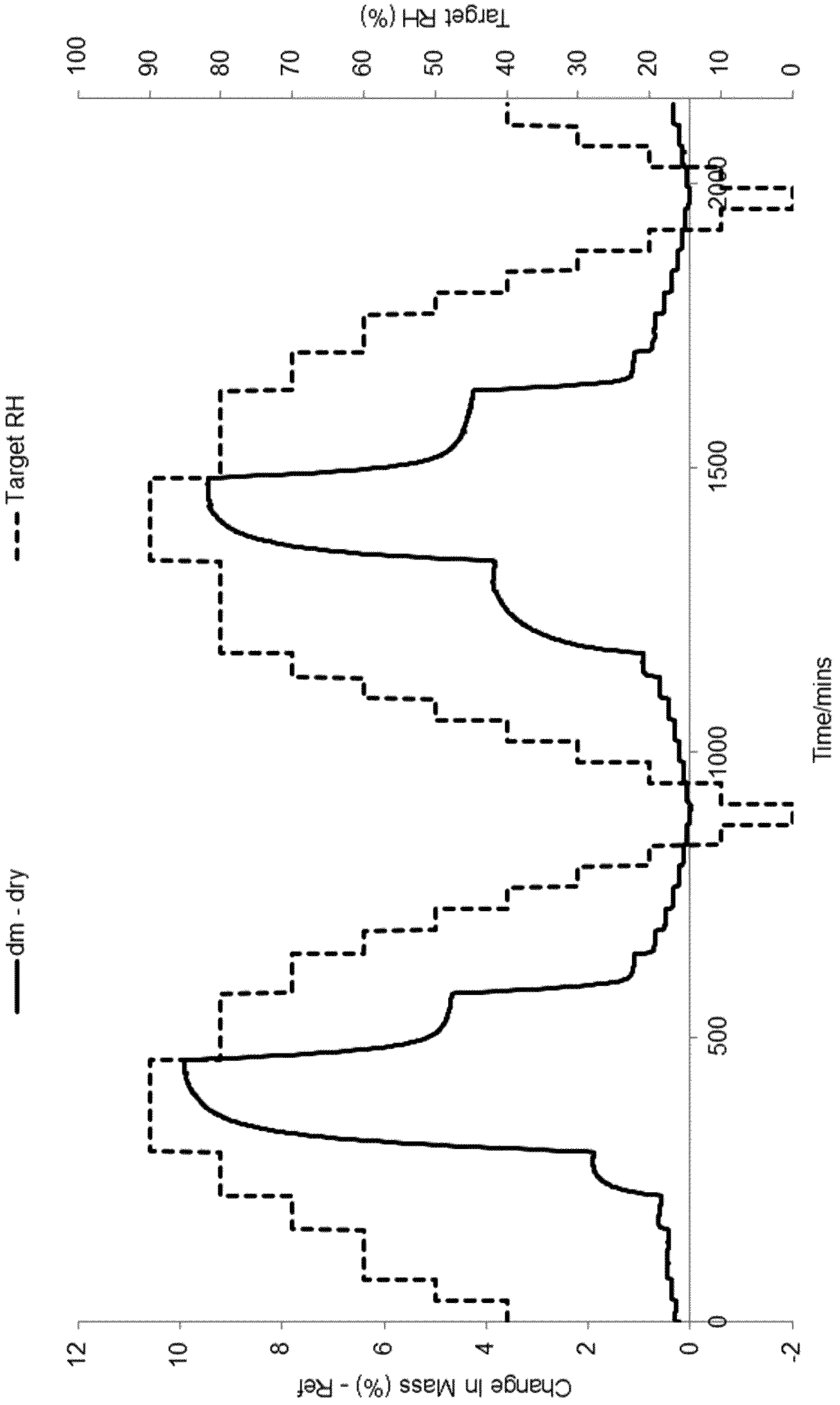
FIG. 22 shows the DVS Kinetic Plot of Form 2, crystalline form of N-(3-(4-(3-(diisobutylanino)propyl)piperazin-1-yl)propyl)-1H-benzo[d]imidazol-2-amine tris-succinate salt.

By DVS analysis, the material was found to take up ca. +0.1 wt. % at 70% RH which is followed by a sharp increase of ca. +9.92 wt. % (approximately 4.3 equiv. water) up to 90% RH. This is then lost readily down to 70% RH and gradually down to 0% RH (FIG. 21) The DVS isotherm plot was correlated to a type I isotherm indicating no change in structure throughout the DVS cycle, as confirmed by the DVS kinetic plot (FIG. 22) wherein no significant change in mass was noted. Post-DVS XRPD analysis showed the material to remain as tris-succinate salt Form 2.

7-day stability showed that Form 2 was stable under 50 °C, 80 °C and ambient light conditions.

Solubilities in different buffers are reported in Table 4.

TABLE 4

Tris-Succinate Form 2 solubility values

| pH Buffer | Solubility (mg/mL) |
|---|---|
| 1.2 HCl | >123.2 |
| 4.5 citrate | >92.4 |
| 6.8 phosphate | >95.7 |

N-(3-(4-(3-(diisobutylamino)propyl)piperazin-1-yl)propyl)-1H-benzo[d]imidazol-2-amine, tris-succinate salt Form 2 was obtained with a one-pot salt formation/crystallization in good yield. The tris-succinate salt Form 2 is very stable (purity and polymorphic form), highly crystalline, highly soluble, not hygroscopic up to 90% relative humidity, stable under stressed conditions. Therefore, this product is a suitable API and is especially of interest for solid formulations.

Example 3: Preparation and Stability of Capsules Containing N-(3-(4-(3-(diisobutylamino)propyl)piperazin-1-yl)propyl)-1H-benzo[d]imidazol-2-amine Sesqui-Succinate Salt Form 1

Preparation of Formulation Blends

Into a cylindrical Drum shell with a volume of 220 mL, 7.5 g of Avicel® PH101 was weighed then 15 g of N-(3-(4-(3-(diisobutylamino)propyl)piperazin-1-yl)propyl)-1H-benzo[d]imidazol-2-amine sesqui-succinate salt Form 1 and finally 7.5 g of Avicel PH101. Adding the Form 1 and Avicel® PH101 excipient in this manner improved the mixing of the two compounds. The final blend is a 50: 50 w/w Form 1: Avicel® PH101. The formulation was mixed using a TorPac ProMixer Powder Mixer/Blender by rotating the drum at a fixed speed of 55-65 rpm for 5 minute intervals with a reverse of direction every 60 seconds. After the 5-minute period a sub-sample was taken and a solution equivalent to 20 μg/mL of Form 1 in water prepared. This was analysed by UV against a standard of the same salt and concentration to determine the Form 1 content in the blend. Mixing was performed until a homogeneous blend was obtained. As the excipient was not water soluble the sample solutions were filtered through a 0.45 μm PTFE syringe filter prior to analysis. The standard was used to confirm that the membrane selected had no adverse effect on the recovery of the analyte. Once a uniform blend was obtained, 100 hard gelatin size 1 white/white capsules were filled. The uniformity of the filled capsules was assessed by weighing 10 filled capsules from each batch. The variation of the empty shells was deemed insignificant.

Stability Sample Preparation of Formulation Blends

The filled capsules were dispensed into HDPE screw top bottles, 10 per bottle and placed on storage. Four bottles were stored at each condition: RT and 40 °C/75% RH. Ten capsules were for the initial time point and were used to determine the weight uniformity. At each time point, 5 capsules were cut open and the contents dispensed into a 20 mL scintillation vial. The powder was then mixed with a spatula and sampled as required for analysis by HPLC (method B) and XRPD.

Blend Uniformity

Blend uniformity was established when 3 concurrent subsample concentrations agreed within 5%. The sesqui-succinate salt Form 1 required only 30 minutes of mixing to achieve homogeneous powders.

TABLE 5

Sesqui-Succinate Form 1 blending homogeneity values

| Time Point (minutes) | Sesqui-succinate Salt Form 1 Blend % Recovery | Absolute Diff |
|---|---|---|
| 5 | 74.6 | N/A |
| 10 | 81.5 | −7 |
| 15 | 101.4 | −20 |
| 20 | 99.2 | 2 |
| 25 | 97.7 | 1 |
| 30 | 98.9 | −1 |

In comparison, the di-sulfate salt Form B blend required up to 60 minutes as it was noted that small aggregates had formed on mixing. Applying excessive shear forces with di-sulfate salt Form B would be necessary to break up the aggregation and to speed up (i.e. reducing to 30 mn) the mixing process but would also likely adversely affect the crystallinity.

Capsule Uniformity: Weight of Filled Capsules

The powder formulation easily filled the capsules due to the free-flowing nature of the blend and a suitable capsule homogeneity was achieved.

TABLE 6 weight of capsules filled with sesqui-succinate salt Form 1 blend

| Replicate | Sesqui-succinate Salt Form 1 Blend (mg) |
|---|---|
| 1 | 267.63 |
| 2 | 269.95 |
| 3 | 266.81 |
| 4 | 273.64 |
| 5 | 263.59 |
| 6 | 271.26 |
| 7 | 260.86 |
| 8 | 271.63 |
| 9 | 264.88 |
| 10 | 262.92 |
| Average | 267.32 |
| Std Dev | 4.25 |
| % RSD | 1.59 |

HPLC Stability Assay

No change in purity was noted throughout the stability storage wherein N-(3-(4-(3-(diisobutylamino)propyl)piperazin-1-yl)propyl)-1H-benzo[d]imidazol-2-amine sesqui-succinate salt Form 1 was retained throughout a 4-week storage of the capsules at RT or 40 °C/75% RH

TABLE 7

HPLC purity of capsules filled with sesqui-succinate salt Form 1 blend

| | Condition | | | | | | |
|---|---|---|---|---|---|---|---|
| | | Room Temperature (RT) | | | 40° C./75% RH | | |
| | Initial | T = 1 week | T = 2 weeks | T = 4 weeks | T = 1 week | T = 2 weeks | T = 4 weeks |
| Purity | 99.3 | 99.4 | 99.4 | 99.3 | 99.3 | 99.4 | 99.3 |

XRPD Stability Analysis

Figure 23:
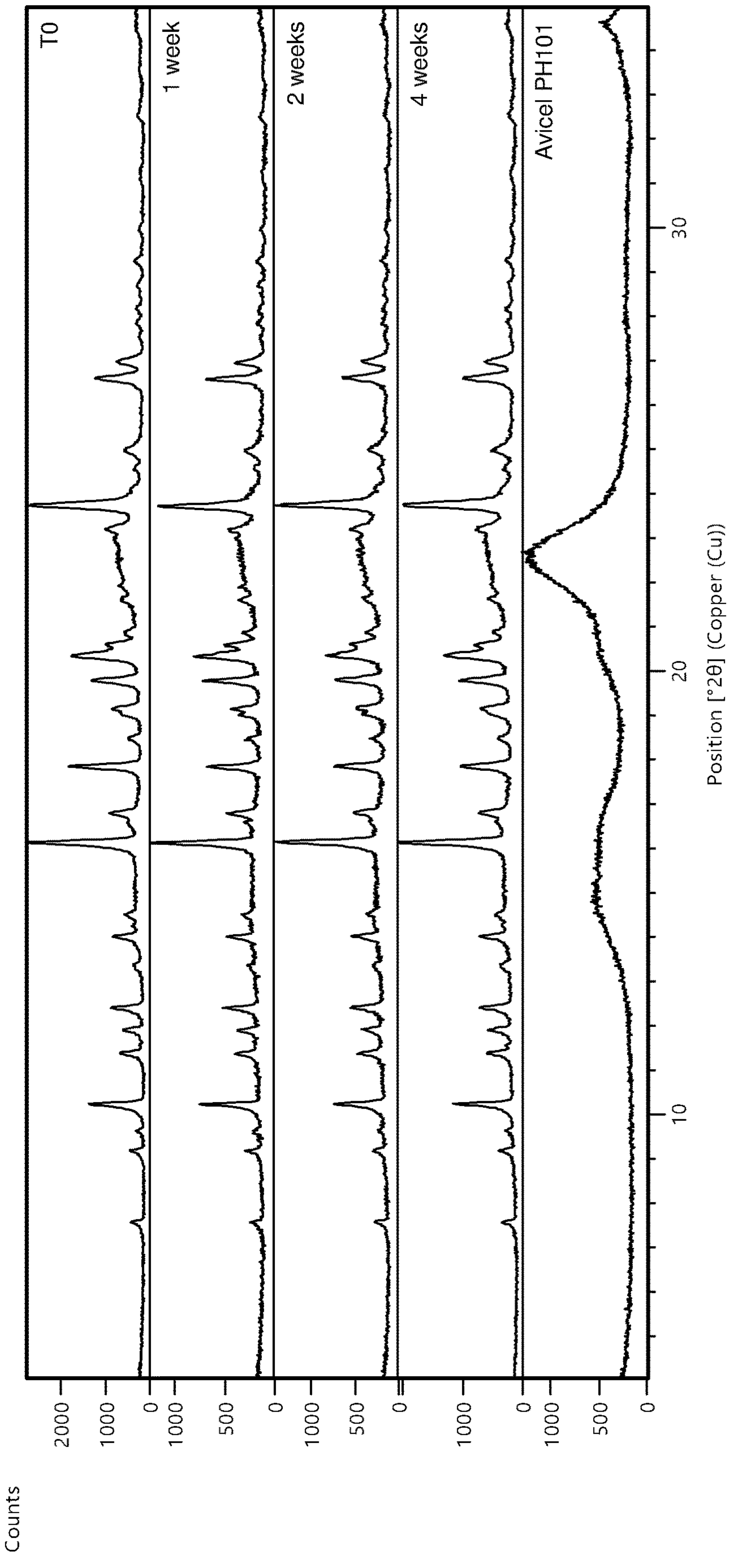
FIG. 23 shows the XRPD (4-35° 2θ) diffractograms of blends of N-(3-(4-(3-(diisobutylamino)propyl)piperazin-1-yl)propyl)-1H-benzo[d]imidazol-2-amine sesqui-succinate salt Form 1 with Avicel® PH101 formulated in hard gelatin capsules and stored at RT.
Figure 24:
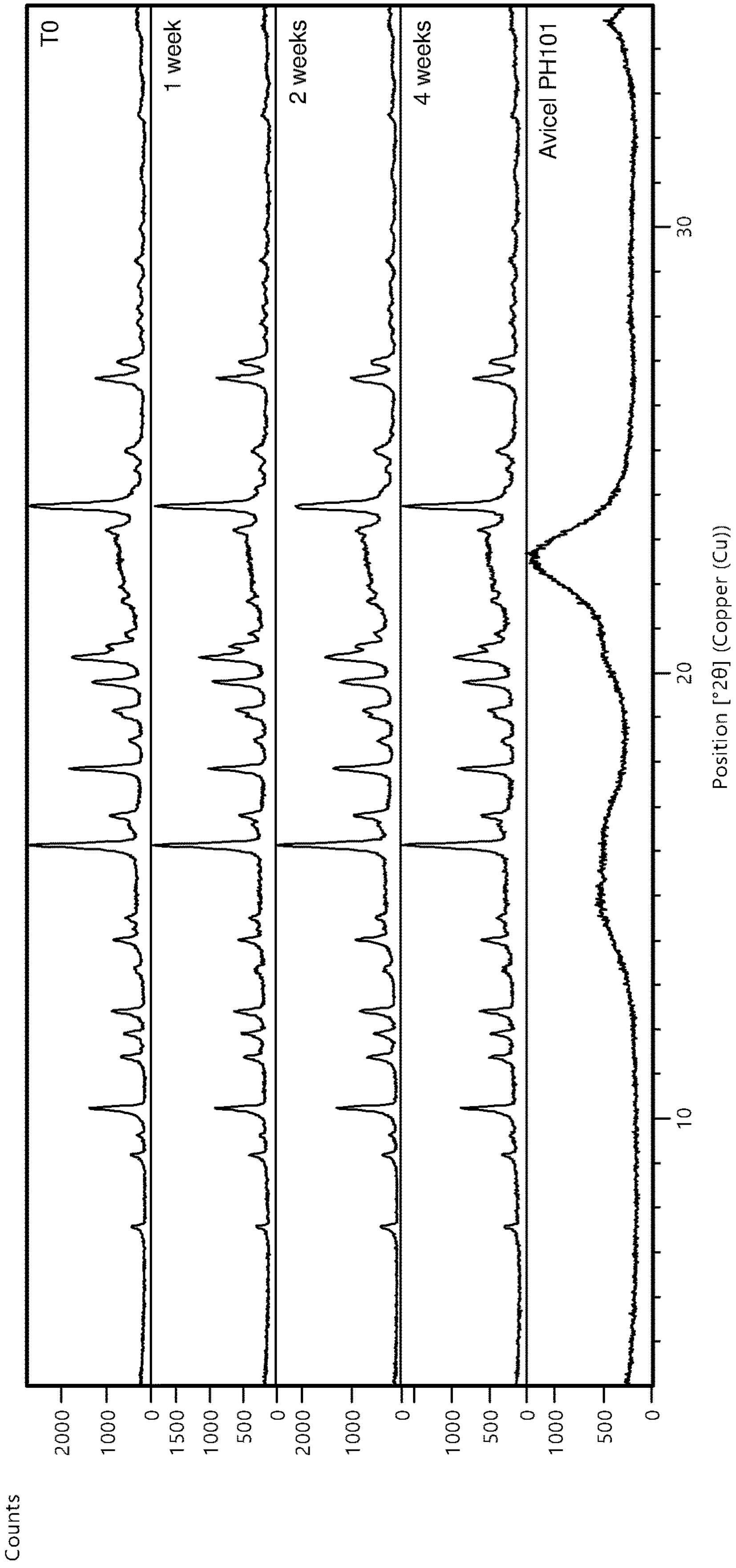
FIG. 24 shows the XRPD (4-35° 2θ) diffractograms of blends of N-(3-(4-(3-(diisobutylamino)propyl)piperazin-1-yl)propyl)-1H-benzo[d]imidazol-2-amine sesqui-succinate salt Form 1 with Avicel® PH101 formulated in hard gelatin capsules and stored at 40 °C/75% RH.

No change in crystalline form was noted throughout the stability storage wherein N-(3-(4-(3-(diisobutylamino)propyl)piperazin-1-yl)propyl)-1H-benzo[d]imidazol-2-amine sesqui-succinate salt Form 1 was retained throughout a 4-week storage of the capsules at RT or 40 °C/75% RH (see FIGS. 23 and 24).

N-(3-(4-(3-(diisobutylamino)propyl)piperazin-1-yl)propyl)-1H-benzo[d]imidazol-2-amine sesqui-succinate salt Form 1 was efficiently blended with a microcrystalline cellulose excipient, providing free-flowing powders which were easily dispensed in capsules, 4-week stability at RT and 40 °C/75% RH was achieved as purity and crystalline form of the API remained unchanged.

Biology Examples

Effect on Cortical Neurons Injured with $A\beta_{1-42}$

Culture of Cortical Neurons

Rat cortical neurons cultured with microglia were cultured as described by Callizot et al. in *J Neurosci Res.* 2013, 91: 706-716 with modifications to include microglial cells. Pregnant female rats (Rats Wistar; Janvier Labs France) of 15 days of gestation were killed, after a deep anesthesia with $CO_2$, by cervical dislocation. Then, fetuses were collected and immediately placed in ice-cold L15 Leibovitz medium with a 2% penicillin (10,000 U/ml) and streptomycin (10 mg/ml) solution (PS) and 1% bovine serum albumin (BSA). Cortexes were treated for 20 min at 37 °C with a trypsin-EDTA solution at a final concentration of 0.05% trypsin and 0.02% EDTA. The dissociation was stopped by addition of Dulbecco's modified Eagle's medium (DMEM) with 4.5 g/liter of glucose, containing DNAse I grade II (final concentration 0.5 mg/ml) and 10% fetal calf serum (FCS). Cells were mechanically dissociated by three forced passages through the tip of a 10-mL pipette. Cells were then centrifuged at 515×g for 10 min at 4 °C. The supernatant was discarded, and the pellet was resuspended in a defined culture medium consisting of Neurobasal medium with a 2% solution of B27 supplement, 2 mmol/liter of L-glutamine, 2% of PS solution, 10 ng/mL of brain-derived neurotrophic factor (BDNF), 2% of heat-inactivated horse serum, 2% of heat-inactivated FCS, 1 g/L of glucose, 1 mM of sodium pyruvate, and 100 M of non-essential amino acids. Viable cells were counted in a Neubauer cytometer, using the trypan blue exclusion test. The cells were seeded at a density of 45,000 per well in 96-well plates (for immunostaining) precoated with poly-L-lysine and cultured at 37 °C in an air (95%)-$CO_2$ (5%) incubator. The culture medium was changed every 2 days.

Test Compound and Human $A\beta_{1-42}$ Exposure

Cortical neurons were intoxicated with Aβ solutions (see below) after 11 days of culture. The $A\beta_{1-42}$ preparation was done following the procedure described by Callizot et al., 2013. Briefly, $A\beta_{1-42}$ peptide was dissolved in the defined culture medium mentioned above, at an initial concentration of 40 μM. This solution was gently agitated for 3 days at 37 °C in the dark and immediately used after being properly diluted in control medium to the concentrations used (5 μM of $A\beta_{1-42}$ preparation containing 0.5 μM of Aβ oligomers (APO) measured by WB). The control medium consisted in the defined culture medium (as described above). Test compound was dissolved in water and mixed in culture medium. The compound was co-administered with the $A\beta_{1-42}$ preparation to the primary cortical neurons cultured with microglia for 72 hours.

Immunostaining

After permeabilization with 0.1% of saponin, cells were blocked for 15 min with PBS containing 1% fetal calf serum. Then, cells were incubated for 2 hours with:

a) For MAP-2 neurons: a chicken polyclonal antibody (Ab) anti microtubule-associated-protein 2 (MAP-2), at a dilution of 1/1000 in PBS, with 1% fetal calf serum and 0.1% of saponin. This antibody binds specifically neurons and neurites, allowing study of neuronal cell survival and neurite network.

b) For AT100 Tau phosphorylation: a mouse monoclonal Ab anti-tau, phosphorylated on the sites Thr212 and Ser214 (AT100), at a dilution of 1/400 in PBS, with 1% fetal calf serum and 0.1% of saponin.

c) For OX-41 microglia: a rabbit polyclonal Ab anti-SIRP alpha/CD172a (OX-41), at a dilution of 1/400 in PBS, with 1% fetal calf serum and 0.1% of saponin. This Ab binds specifically microglia cells, which allow the evaluation of their activation.

These antibodies were revealed with Alexa Fluor 350 donkey anti-chicken IgG, Alexa Fluor 488 goat anti-mouse IgG, Alexa Fluor 568 goat anti-rabbit IgG at a dilution of 1/400 in PBS containing 1% FCS, 0.1% saponin, for 1 hour at room temperature.

For each condition, 30 pictures per well were automatically taken using ImageXpress (Molecular Devices) at 20× magnification. All images were generated using the same acquisition parameters. Analyses were automatically performed by using Custom Module Editor (Molecular Devices).

The following read-outs were investigated:

neuron survival: total number of neurons (MAP-2 staining)

neurite network (MAP-2 staining in mun)

phospho Tau inside neurons: area of colocalization of AT100 and MAP-2 ($\mu m^2$ of overlapping)

microglia activation: total area of microglial cells (OX41 staining in $\mu m^2$)

Extracellular Progranulin Quantification

Levels of PGRN in the culture medium were determined by ELISA (Progranulin (rat) ELISA lit, Adipogen, Coger) according to manufacturer's recommendations. Briefly, 100 µL of supernatant was added directly into well strips for 1 h at 37 °C. Then 100 µL of detection antibody was added for 1 h at 37 °C and 100 µL of HRP labeled streptavidin was added for 1 h at 37 °C. Finally, 100 µL of TMB substrate solution was added for 10 min at room temperature. Optical density (OD) was assessed by spectrophotometry at 450 nm wavelength with a Glomax apparatus (Promega). The activity of the peroxidase is proportional to the concentration of PGRN.

Statistical Analysis

Results are expressed in percentage of control. All values show the mean +/−SEM (standard error of the mean) from 4-6 wells per condition. Graphs and statistical analyses were performed on the different conditions (ANOVA followed by Dunnett's or Fisher's t test) using GraphPad Prism software version 7.04. *$p<0.05$ was considered significant.

Results

Figure 25:
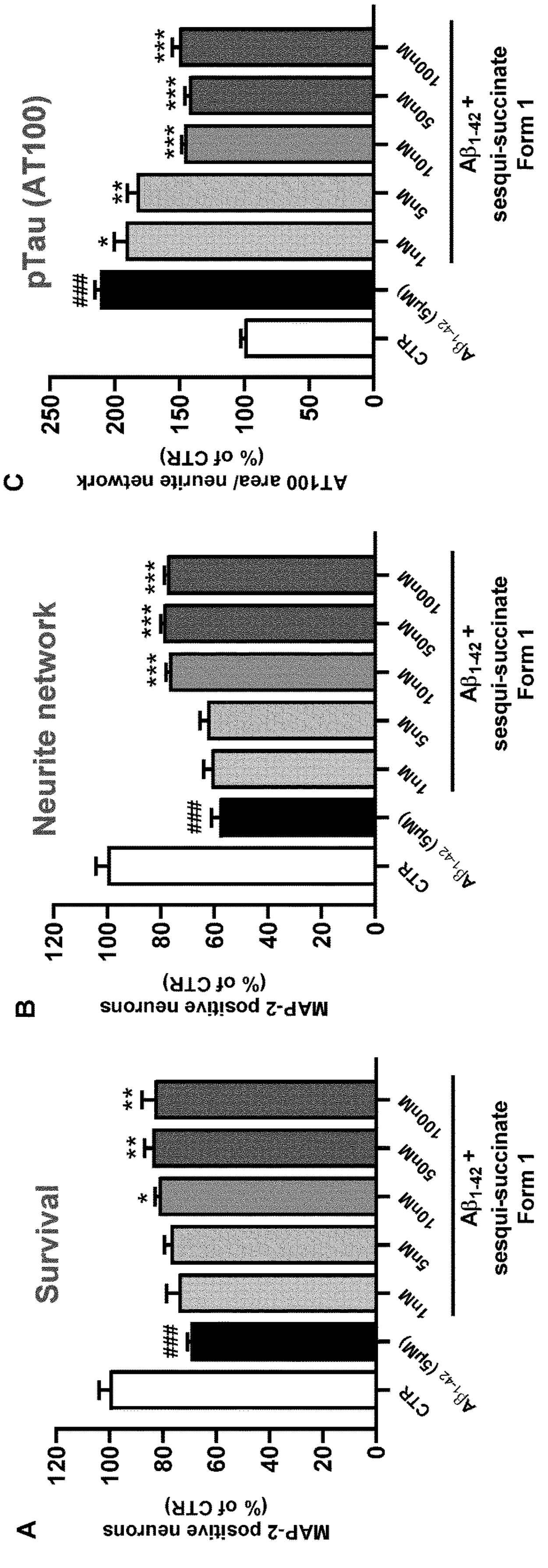
FIG. 25 shows the effects of N-(3-(4-(3-(diisobutylamino)propyl)piperazin-1-yl)propyl)-1H-benzo[d]imidazol-2-amine sesqui-succinate salt Form 1 on the survival (A), the neurite network (B) and on Tau phosphorylation (AT100) (C) in cortical neurons cultured with microglia after $A\beta_{1-42}$ injury for 72 h. Results are expressed in percentage of control (CTR) condition as mean±SEM (n=4-6). One-way ANOVA followed by Fisher's test. *;  or * indicate p<0.05; p<0.01 or p<0.001 vs $A\beta_{1-42}$ or ###vs CTR, p<0.05 was considered significant.

Neuronal survival: the intoxication with $A\beta_{1-42}$ significantly decreased the survival of cortical neurons, as compared to the control group (FIG. 25A). Sesqui-succinate Form 1 was neuroprotective at the highest doses (10 nM to 100 nM).

Neurite network: the total length of neurite network was significantly decreased after the Api-42 injury (FIG. 25B). The neurite network was significantly longer in presence of the highest doses of sesqui-succinate Form 1 (10 nM to 100 nM).

AT100: under application of $A\beta_{1-42}$, a significant increase of AT100 was observed in MAP-2 cortical neurons (FIG. 25C). Sesqui-succinate Form 1 significantly reduced the hyperphosphorylation of Tau at doses above 1 nM.

Activation of microglial cells: as expected, the intoxication with Api-42 triggered an activation of microglial cells as compared to the control group (FIG. 26A). At the investigated doses, sesqui-succinate salt Form 1 was able to decrease the activation of microglial cells.

Extracellular PGRN: in presence of A01-42, the level of PGRN in the supernatant was significantly lower when compared to that of the control group. The sesqui-succinate salt Form 1 significantly increased the levels of extracellular PGRN at the concentration of 10 nM (FIG. 26B).

In line with these results, it can be concluded that the sesqui-succinate salt Form 1 was able to a) be neuroprotective, b) preserve the neurite network, b) reduce the hyperphosphorylation of Tau, d) mitigate microglial activation and thus neuroinflammation and e) promote the release of progranulin neurotrophic factor in the supernatant of cultured cells. Therefore, the succinate salts of the invention are useful for the treatment of neurodegenerative diseases, in particular of tauopathies and Parkinson's disease.

Effect on Mesencephalic Neurons Injured with $MPP^+$ or Rotenone

Culture of Mesencephalic Neurons

Rat dopaminergic neurons were cultured as described by Visanji et al. in FASEB J. 2008, 22(7): 2488-2497 and Callizot et al., in PlosOne 2019: https://doi.org/10.1371/journal.pone.0215277. Briefly, pregnant female rat (Wistar) of 15 days of gestation were killed using a deep anesthesia with $CO_2$ chamber and a cervical dislocation. The midbrains obtained from 15-day-old rat embryos (Janvier, France) were dissected under a microscope. The embryonic midbrains were removed and placed in ice-cold medium of Leibovitz (L15) containing 2% of Penicillin-Streptomycin (PS) and 1% of BSA. The ventral portion of the mesencephalic flexure, a region of the developing brain rich in dopaminergic neurons, were used for the cell preparations. The midbrains were dissociated by trypsinization for 20 min at 37 °C (solution at a final concentration of 0.05% trypsin and 0.02% EDTA). The reaction was stopped by the addition of DMEM containing DNAase I grade II (0.5 mg/mL) and 10% of FCS. Cells were then mechanically dissociated by 3 passages through a 10 ml pipette. Cells were then centrifuged at 180×g for 10 min at +4 °C on a layer of BSA (3.5%) in L15 medium. The supernatant was discarded and the cell pellets were re-suspended in a defined culture medium consisting of Neurobasal supplemented with B27 (2%), L-glutamine (2 mM) and 2% of PS solution and 10 ng/mL of BDNF and 1 ng/mL of Glial-Derived Neurotrophic Factor (GDNF). Viable cells were counted in a Neubauer cytometer using the trypan blue exclusion test. The cells were seeded at a density of 40,000 cells/well in 96 well-plates (pre-coated with poly-L-lysine) and maintained in a humidified incubator at 37 °C in 5% $CO_2$/95% air atmosphere. Half of the medium was changed every 2 days with fresh medium.

For 96 wells plates, only 60 wells were used. The wells of first and last lines and columns were not used (to avoid any edge effect) and were filled with sterile water.

Test Compound and Mitochondrial Stress

Vehicle: culture medium (0.1% PBS).

Pre-treatment: On day 4, the sesqui-succinate salt Form 1 was solubilized in culture medium and added to the culture for 48 hours.

MPP+ injury: On day 6 and 48 hours after the incubation of the sesqui-succinate salt Form 1 or immediately after the incubation thereof, $MPP^+$ was added to a final concentration of 4 M, diluted in control medium still in presence of compound for 48 h.

Rotenone injury: On day 6 and 48 hours after the incubation of the sesqui-succinate salt Form 1 or immediately after the incubation thereof, rotenone was added to a final concentration of 10 nM, diluted in control medium still in presence of compound for 24 h.

Immunostaining

After injury (24 h or 48 h), the cell culture supernatant was removed, and the cells were fixed by a solution of 4% paraformaldehyde in PBS, pH=7.3 for 20 min at room temperature. Cells were washed twice in PBS. Cell membrane permeabilization and blocking of non-specific binding sites were performed with a solution of PBS containing 0.1% saponin and 1% FCS for 15 min at room temperature. Then, cells were then incubated with:

a) For Tyrosine Hydroxylase (TH): monoclonal anti-TH antibody produced in mouse at dilution of 1/10000 in PBS containing 1% FCS, 0.1% saponin, for 2 hours at room temperature.

b) For alpha synuclein (α-syn): polyclonal anti-α-syn antibody produced in rabbit at dilution of 1/200 in PBS containing 1% FCS, 0.1% saponin, for 2 hours at room temperature.

Primary antibodies were revealed with Alexa Fluor 488 goat anti-mouse IgG and with Alexa Fluor 568 goat anti-rabbit IgG, both at the dilution 1/400 in PBS containing 1% FCS, 0.1% saponin, for 1 hour at room temperature. Nucleus were labeled with Hoechst dye (1/1000).

For each condition, 20 pictures (representative of the whole well area) were automatically taken using ImageXpress® (Molecular Devices) at 10× magnification using the same acquisition parameters. From images, the analyses were automatically performed by MetaXpress® (Molecular Devices).

The following read-outs were investigated:

neuron survival: total number of TH neurons (TH staining), neurite network: total length of neurite network of TH positive neurons (in μm)

α-syn aggregation (area of overlapping between TH and α-syn staining in $\mu m^2$)

Statistical Analysis

Results are expressed in percentage of control. All values show the mean +/−SEM (standard error of the mean) from 4-6 wells per condition. Statistical analyses on the different conditions (ANOVA followed by Fisher's LSD test) and graphs were performed using GraphPad Prism software version 7.04. $p<0.05$ was considered significant.

Results

Effects of Sesqui-Succinate Form 1 on TH(+) Neurons Injured with $MPP^+$

Neuronal survival: the intoxication with $MPP^+$ significantly decreased the survival of dopaminergic (TH positive) neurons, as compared to the control group. Sesqui-succinate Form 1 was neuroprotective at the 50 nM dose (FIG. 27A).

Neurite network: the total length of neurite network was significantly decreased after the $MPP^+$ injury. The integrity of the neurite network was significantly improved with a 50 nM dose of sesqui-succinate Form 1 (FIG. 27B).

α-syn aggregation: under application of $MPP^+$, a significant increase of α-syn aggregation was observed in the dopaminergic neurons. This aggregation was significantly reduced after pre-incubation of sesqui-succinate Form 1 at all tested concentrations. The coincubation with 50 or 100 nM sesqui-succinate Form 1, significantly reduced α-syn aggregation (FIG. 27C).

Effects of Sesqui-Succinate Form 1 on TH(+) Neurons Injured with Rotenone

Neuronal survival: the intoxication with rotenone induced a significant loss of the dopaminergic neurons, as compared to the control group. Sesqui-succinate Form 1 was significantly neuroprotective at doses of 10 and 50 nM when pre-incubated. However, it significantly increased neuronal survival at all concentrations when administered directly with rotenone (FIG. 28A).

Neurite network: the integrity of neurite network was significantly decreased after the rotenone injury. Both pre and co-treatment with sesqui-succinate Form 1 significantly improved the neurite network at all doses from 10 to 100 nM (FIG. 28B).

α-syn aggregation: rotenone significantly increased the aggregation of α-syn in dopaminergic neurons. This pathological aggregation was significantly reduced when sesqui-succinate Form 1 was pre-incubated or applied directly with rotenone (from 10 to 100 nM). Notably, the aggregation of α-syn was prevented when 100 nM sesqui-succinate Form 1 were co-administered (FIG. 28C).

The invention claimed is:

1. A process for making a crystalline form of N-(3-(4-(3-(diisobutylamino)propyl)piperazin-1-yl)propyl)-1H-benzo[d]imidazol-2-amine sesqui-succinate salt comprising the steps of:

step 1: dissolving N-(3-(4-(3-(diisobutylamino)propyl)piperazin-1-yl)propyl)-1H-benzo[d]imidazol-2-amine in an organic solvent;

step 2: heating the reaction medium to temperature B, wherein temperature B is defined as a temperature comprised between 30 and 50 °C;

step 3: adding a substantially equimolar amount of succinic acid;

step 4: stirring the reaction medium at temperature B for 0.25 to 4 hours;

step 5: temperature cycling the reaction medium between temperature A and temperature B in 2 to 4-hour cycles for 10 to 30 hours wherein temperature A is defined as a temperature comprised between 0 and 10 °C;

step 6: cooling down the reaction medium to temperature A;

step 7: filtering the reaction medium at temperature A;

step 8: washing the filter cake with said organic solvent at temperature A;

step 9: drying the filter cake at a temperature between 30 and 50 °C.

2. A crystalline form of a succinate salt of N-(3-(4-(3-(diisobutylamino)propyl)piperazin-1-yl)propyl)-1H-benzo[d]imidazol-2-amine having formula II:

Formula II

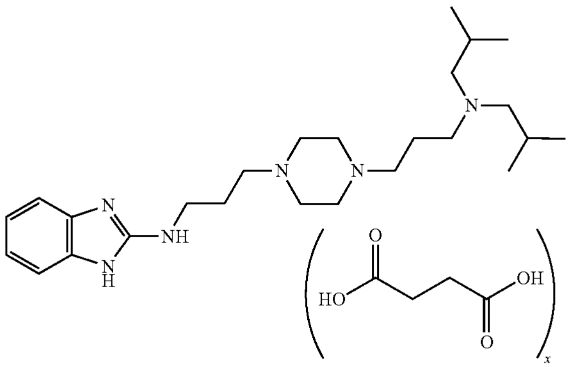

or a pharmaceutically acceptable solvate thereof, wherein x is 1.5 and the crystalline form has an X-ray powder diffraction (XRPD) pattern with peaks at diffraction angles of 2θ=3.8°±0.2°, 10.3°±0.2, 12.4°±0.2°, 16.2°±0.2°, 17.9°±0.2°, 19.8°±0.2°, 20.4°±0.2°, 23.8°±0.2° and 26.7°±0.2° when irradiated with a CuKα light source.

3. A crystalline form of a succinate salt of N-(3-(4-(3-(diisobutylamino)propyl)piperazin-1-yl)propyl)-1H-benzo[d]imidazol-2-amine having formula II:

Formula II

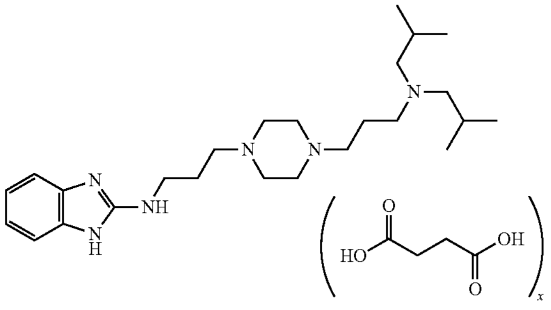

wherein x is 1.5 and the crystalline form has an X-ray powder diffraction (XRPD) pattern with peaks at diffraction angles of 2θ=3.8°±0.2°, 10.3°±0.2°, 12.4°±0.2°, 16.2°±0.2°±17.9°±0.2°, 19.8°±0.2°, 20.4°±0.2°, 23.8°±0.2° and 26.7°±0.2° when irradiated with a CuKα light source.

* * * * *